United States Patent
Jun et al.

(10) Patent No.: US 12,356,856 B2
(45) Date of Patent: Jul. 8, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Ji-Song Jun, Gyeonggi-do (KR); Hee-Ryong Kang, Gyeonggi-do (KR); Chi-Sik Kim, Gyeonggi-do (KR); Kyoung-Jin Park, Gyeonggi-do (KR); Jin-Man Kim, Gyeonggi-do (KR); Seung-Hyun Yoon, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 800 days.

(21) Appl. No.: 17/603,506

(22) PCT Filed: Apr. 9, 2020

(86) PCT No.: PCT/KR2020/004844
§ 371 (c)(1),
(2) Date: Oct. 13, 2021

(87) PCT Pub. No.: WO2020/218762
PCT Pub. Date: Oct. 29, 2020

(65) Prior Publication Data
US 2022/0181558 A1    Jun. 9, 2022

(30) Foreign Application Priority Data
Apr. 26, 2019 (KR) .................. 10-2019-0048820

(51) Int. Cl.
| | | |
|---|---|---|
| H01L 51/50 | (2006.01) | |
| C07D 251/24 | (2006.01) | |
| C07D 403/04 | (2006.01) | |
| C07D 403/10 | (2006.01) | |
| C07D 405/04 | (2006.01) | |
| C07D 487/04 | (2006.01) | |
| C09K 11/06 | (2006.01) | |
| H10K 85/60 | (2023.01) | |
| H10K 50/11 | (2023.01) | |
| H10K 101/00 | (2023.01) | |
| H10K 101/10 | (2023.01) | |

(52) U.S. Cl.
CPC ....... *H10K 85/6572* (2023.02); *C07D 251/24* (2013.01); *C07D 403/04* (2013.01); *C07D 403/10* (2013.01); *C07D 405/04* (2013.01); *C07D 487/04* (2013.01); *C09K 11/06* (2013.01); *H10K 85/624* (2023.02); *H10K 85/654* (2023.02); *H10K 85/6574* (2023.02); *C09K 2211/1018* (2013.01); *H10K 50/11* (2023.02); *H10K 2101/10* (2023.02); *H10K 2101/90* (2023.02)

(58) Field of Classification Search
None
See application file for complete search history.

(56) References Cited

U.S. PATENT DOCUMENTS

| | | | |
|---|---|---|---|
| 2016/0308138 A1 | 10/2016 | Kim et al. | |
| 2017/0047529 A1* | 2/2017 | Min | C07D 209/86 |
| 2017/0098784 A1 | 4/2017 | Kim et al. | |
| 2018/0294420 A1 | 10/2018 | Feldman et al. | |
| 2019/0181351 A1 | 6/2019 | Jang et al. | |

FOREIGN PATENT DOCUMENTS

| | | |
|---|---|---|
| KR | 20160122889 A | 10/2016 |
| KR | 20170073245 A | 6/2017 |
| KR | 20190010499 A | 1/2019 |
| WO | 2013157886 A1 | 10/2013 |

OTHER PUBLICATIONS

Notification of Preliminary Rejection from Korea Patent Office for Korean application No. 2019-0048820; Application Date: Apr. 26, 2019.

* cited by examiner

*Primary Examiner* — Gregory D Clark
(74) *Attorney, Agent, or Firm* — G. Creston Campbell

(57) ABSTRACT

The present disclosure relates to a plurality of host materials comprising a first host material comprising a compound represented by formula 1, and a second host material comprising a compound represented by formula 2, and an organic electroluminescent device comprising the same. By comprising a specific combination of compounds as a host material, it is possible to provide an organic electroluminescent device having high luminous efficiency and/or improved lifespan properties, compared to conventional organic electroluminescent devices.

9 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. In many applications such as TVs and lightings. OLED lifetime is insufficient, and high efficiency of OLEDs is still required. Typically, the higher the luminance of an OLED is, the shorter the lifetime an OLED has. Therefore, an OLED having high luminous efficiency and/or long lifespan characteristics is required for long time use and high resolution of a display.

In order to enhance luminous efficiency, driving voltage and/or lifespan, various materials or concepts for an organic layer of an organic electroluminescent device have been proposed. However, they were not satisfactory in practical use.

Korean Patent Application Laying-Open No. 2018-0013449 discloses an organic electroluminescent device using a plurality of host materials comprising a compound comprising carbazole, dibenzofuran, or dibenzothiopene and a compound comprising indolocarbazole. However, said reference does not specifically disclose an organic electroluminescent device using a specific combination of a plurality of host materials of the present disclosure. In addition, development of a host material for improving performances of an OLED is still required.

DISCLOSURE OF INVENTION

Technical Problem

The objective of the present disclosure is to provide an organic electroluminescent device having high luminous efficiency and/or improved lifespan properties by comprising a plurality of host materials including a specific combination of compounds.

Solution to Problem

The present inventors perceived that a host compound in a form like formula 1 cannot sufficiently improve the luminous efficiency and lifespan of the device even though the hole mobility is high due to high HOMO (highest occupied molecular orbital) level, and researched in order to solve this problem. As a result, the present inventors found that the luminous efficiency and lifespan of the device can be improved when combining host compounds of specific structures. More specifically, the present inventors found that the above objective can be achieved by using a plurality of host materials comprising a first host material comprising a compound represented by the following formula 1, and a second host material comprising a compound represented by the following formula 2:

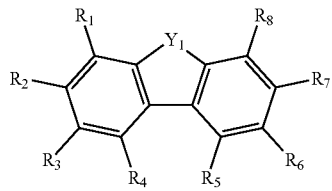

wherein $Y_1$ represents O, S, $CR_{11}R_{12}$, or $NR_{13}$;

$R_{11}$ and $R_{12}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl; or $R_1$ and $R_{12}$ may be linked to each other to form a spiro ring;

$R_1$ to $R_8$, and $R_{13}$ each independently represent -$L_1$-$(Ar_1)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl, with a proviso that one or more of $R_1$ to $R_8$, and $R_{13}$ is -$L_1$-$(Ar_1)_a$;

$L_1$ represents a single bond, a substituted or unsubstituted (C6-C30)arylene, or a substituted or unsubstituted (3- to 30-membered)heteroarylene, where if a plurality of $L_1$'s are present, each of $L_1$ may be the same or different;

$Ar_1$ each independently represents a substituted or unsubstituted nitrogen-containing (3- to 30-membered)heteroaryl, where if a plurality of $Ar_1$'s are present, each of $Ar_1$ may be the same or different;

a represents an integer of 1 to 4, where if a plurality of a's are present, each of a may be the same or different, and where if a is an integer of 2 or more, each of $Ar_1$ may be the same or different;

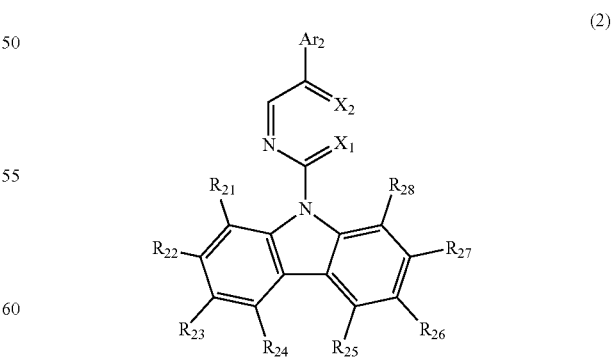

wherein $Ar_2$ each independently represent hydrogen, deuterium, a halogen, a cyano, a substituted or unsubstituted (C1-C30) alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl;

$X_1$ and $X_2$ each independently represent N or CH, with a proviso that one or more of $X_1$ and $X_2$ is N;

at least one of $R_{21}$ and $R_{22}$, $R_{22}$ and $R_{23}$, $R_{23}$ and $R_{24}$, $R_{25}$ and $R_{26}$, $R_{26}$ and $R_{27}$, and $R_{27}$ and $R_{28}$ are fused in each two * positions of the following formula to form a ring of the following formula;

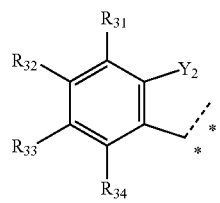

the remainders of $R_{21}$ to $R_{28}$ which do not form a ring and $R_{31}$ to $R_{34}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl, where if a plurality of $R_{31}$'s to $R_{34}$'s are present, each of $R_{31}$, each of $R_{32}$, each of $R_{33}$, and each of $R_{34}$ may be the same or different;

$Y_2$ represents O, S. $CR_{14}R_{15}$, or $NR_{16}$, where if a plurality of $Y_2$'s are present, each of $Y_2$ may be the same or different;

$R_{14}$ and $R_{15}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl; or $R_{14}$ and $R_{15}$ may be linked to each other to form a spiro ring; and $R_{16}$ represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl.

Advantageous Effects of Invention

By comprising a plurality of host materials according to the present disclosure, an organic electroluminescent device having high luminous efficiency and/or improved lifespan properties compared to conventional organic electroluminescent devices can be provided, and it is possible to produce a display device or a lighting device using the same.

MODE FOR THE INVENTION

Hereinafter, the present disclosure will be described in detail. However, the following description is intended to explain the invention, and is not meant in any way to restrict the scope of the invention.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. The at least two compounds may be comprised in the same layer or different layers through methods used in the art, and, for example, may be mixture-evaporated or co-evaporated, or may be individually evaporated.

The term "a plurality of host materials" in the present disclosure means a host material comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host materials of the present disclosure may be a combination of at least two host materials, and selectively may further comprise conventional materials comprised in an organic electroluminescent material. A plurality of host materials of the present disclosure may be comprised in any light-emitting layer constituting an organic electroluminescent device, and at least two compounds comprised in the plurality of host materials may be comprised together in one light-emitting layer or may respectively be comprised in different light-emitting layers, through methods used in the art. For example, the at least two compounds may be mixture-evaporated or co-evaporated, or may be individually evaporated.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, and more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl may include a phenyl, a 1-naphthyl, a 2-naphthyl, a 1-anthryl, a 2-anthryl, a 9-anthryl, a benzanthryl, a 1-phenanthryl, a 2-phenanthryl, a 3-phenanthryl, a 4-phenanthryl, a 9-phenanthryl, a naphthacenyl, a pyrenyl, a 1-chrysenyl, a 2-chrysenyl, a 3-chrysenyl, a 4-chrysenyl, a 5-chrysenyl, a 6-chrysenyl, a benzo[c]phenanthryl, a benzo[g]chrysenyl, a 1-triphenylenyl, a 2-triphenylenyl, a 3-triphenylenyl, a 4-triphenylenyl, a 1-fluorenyl, a 2-fluorenyl, a 3-fluorenyl, a 4-fluorenyl, a 9-fluorenyl, a benzofluorenyl, a dibenzofluorenyl, a 2-biphenylyl, a 3-biphenylyl, a 4-biphenylyl, an o-terphenyl, an m-terphenyl-4-yl, an m-terphenyl-3-yl, an m-terphenyl-2-yl, a p-terphenyl-4-yl, a p-terphenyl-3-yl, a p-terphenyl-2-yl, an m-quaterphenyl, a 3-fluoranthenyl, a 4-fluoranthenyl, an 8-fluoranthenyl, a 9-fluoranthenyl, a benzofluoranthenyl, an o-tolyl, an m-tolyl, a p-tolyl, a 2,3-xylyl, a 3,4-xylyl, a 2,5-xylyl, a mesityl, an o-cumenyl, an m-cumenyl, a p-cumenyl, a p-t-butylphenyl, a p-(2-phenylpropyl)phenyl, a 4'-methylbiphenylyl, a 4"-t-butyl-p-terphenyl-4-yl, a 9,9-dimethyl-1-fluorenyl, a 9,9-dimethyl-2-fluorenyl, a 9,9-dimethyl-3-fluorenyl, a 9,9-dimethyl-4-fluorenyl, a 9,9-diphenyl-1-fluorenyl, a 9,9-diphenyl-2-fluorenyl, a 9,9-diphenyl-3-fluorenyl, a 9,9-diphenyl-4-fluorenyl, etc.

The term "(3- to 30-membered)heteroaryl(ene)" is meant to be an aryl having 3 to 30 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzonaphthofuranyl, benzonaphthothiophenyl, diazadibenzofuranyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, benzoquinolyl, isoquinolyl, benzoisoquinolyl, cinnolinyl, quinazolinyl, benzoquinazolinyl, quinoxalinyl, benzoquinoxalinyl, naphthyridinyl, triazanaphthyl, benzothienopyrimidinyl, carbazolyl, benzocarbazolyl, dibenzocarbazolyl, phenoxazinyl, phenothiazinyl, phenanthridinyl, benzodioxolyl, and dihydroacridinyl. More specifically, the above heteroaryl may include a 1-pyrrolyl, a 2-pyrrolyl, a 3-pyrrolyl, a pyrazinyl, a 2-pyridinyl, a 2-pyrimidinyl, a 4-pyrimidinyl, a 5-pyrimidinyl, a 6-pyrimidinyl, a 1,2,3-triazin-4-yl, a 1,2,4-triazin-3-yl, a 1,3,5-triazin-2-yl, a 1-imidazolyl, a 2-imidazolyl, a 1-pyrazolyl, a 1-indolidinyl, a 2-indolidinyl, a 3-indolidinyl, a 5-indolidinyl, a 6-indolidinyl, a 7-indolidinyl, an 8-indolidinyl, a 2-imidazopyridinyl, a 3-imidazopyridinyl, a 5-imidazopyridinyl, a 6-imidazopyridinyl, a 7-imidazopyridinyl, an 8-imidazopyridinyl, a 3-pyridinyl, a 4-pyridinyl, a 1-indolyl, a 2-indolyl, a 3-indolyl, a 4-indolyl, a 5-indolyl, a 6-indolyl, a 7-indolyl, a 1-isoindolyl, a 2-isoindolyl, a 3-isoindolyl, a 4-isoindolyl, a 5-isoindolyl, a 6-isoindolyl, a 7-isoindolyl, a 2-furyl, a 3-furyl, a 2-benzofuranyl, a 3-benzofuranyl, a 4-benzofuranyl, a 5-benzofuranyl, a 6-benzofuranyl, a 7-benzofuranyl, a 1-isobenzofuranyl, a 3-isobenzofuranyl, a 4-isobenzofuranyl, a 5-isobenzofuranyl, a 6-isobenzofuranyl, a 7-isobenzofuranyl, a 2-quinolyl, a 3-quinolyl, a 4-quinolyl, a 5-quinolyl, a 6-quinolyl, a 7-quinolyl, an 8-quinolyl, a 1-isoquinolyl, a 3-isoquinolyl, a 4-isoquinolyl, a 5-isoquinolyl, a 6-isoquinolyl, a 7-isoquinolyl, an 8-isoquinolyl, a 2-quinoxalinyl, a 5-quinoxalinyl, a 6-quinoxalinyl, a 1-carbazolyl, a 2-carbazolyl, a 3-carbazolyl, a 4-carbazolyl, a 9-carbazolyl, an azacarbazolyl-1-yl, an azacarbazolyl-2-yl, an azacarbazolyl-3-yl, an azacarbazolyl-4-yl, an azacarbazolyl-5-yl, an azacarbazolyl-6-yl, an azacarbazolyl-7-yl, an azacarbazolyl-8-yl, an azacarbazolyl-9-yl, a 1-phenanthridinyl, a 2-phenanthridinyl, a 3-phenanthridinyl, a 4-phenanthridinyl, a 6-phenanthridinyl, a 7-phenanthridinyl, an 8-phenanthridinyl, a 9-phenanthridinyl, a 10-phenanthridinyl, a 1-acridinyl, a 2-acridinyl, a 3-acridinyl, a 4-acridinyl, a 9-acridinyl, a 2-oxazolyl, a 4-oxazolyl, a 5-oxazolyl, a 2-oxadiazolyl, a 5-oxadiazolyl, a 3-furazanyl, a 2-thienyl, a 3-thienyl, a 2-methylpyrrol-1-yl, a 2-methylpyrrol-3-yl, a 2-methylpyrrol-4-yl, a 2-methylpyrrol-5-yl, a 3-methylpyrrol-1-yl, a 3-methylpyrrol-2-yl, a 3-methylpyrrol-4-yl, a 3-methylpyrrol-5-yl, a 2-t-butylpyrrol-4-yl, a 3-(2-phenylpropyl)pyrrol-1-yl, a 2-methyl-1-indolyl, a 4-methyl-1-indolyl, a 2-methyl-3-indolyl, a 4-methyl-3-indolyl, a 2-t-butyl-1-indolyl, a 4-t-butyl-1-indolyl, a 2-t-butyl-3-indolyl, a 4-t-butyl-3-indolyl, a 1-dibenzofuranyl, a 2-dibenzofuranyl, a 3-dibenzofuranyl, a 4-dibenzofuranyl, a 1-dibenzothiophenyl, a 2-dibenzothiophenyl, a 3-dibenzothiophenyl, a 4-dibenzothiophenyl, a 1-silafluorenyl, a 2-silafluorenyl, a 3-silafluorenyl, a 4-silafluorenyl, a 1-germafluorenyl, a 2-germafluorenyl, a 3-germafluorenyl, and a 4-germafluorenyl. Furthermore, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted alkyl, the substituted cycloalkyl, the substituted cycloalkenyl, the substituted heterocycloalkyl, the substituted aryl(ene), and the substituted heteroaryl(ene) in the formulas of the present disclosure, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30) alkyl(s), a (3- to 30-membered)heteroaryl(s), and a tri(C6-C30)arylsilyl(s); a tri(C1-C30)alkylsilyl; a tri(C6-C30)arylsilyl; a di(C1-C30)alkyl(C6-C30)arylsilyl; a (C1-C30) alkyldi(C6-C30)arylsilyl; an amino; a mono- or di-(C1-C30) alkylamino; a mono- or di-(C6-C30)arylamino; a (C1-C30) alkyl(C6-C30)arylamino; a (C1-C30)alkylcarbonyl; a (C1-C30)alkoxycarbonyl; a (C6-C30)arylcarbonyl; a di(C6-C30) arylboronyl; a di(C1-C30)alkylboronyl; a (C1-C30)alkyl (C6-C30)arylboronyl; a (C6-C30)aryl(C1-C30)alkyl; and a (C1-C30)alkyl(C6-C30)aryl; preferably, at least one selected from the group consisting of a (C1-C6)alkyl, a substituted or unsubstituted (C6-C20)aryl, a substituted or unsubstituted (5- to 15-membered)heteroaryl, and an unsubstituted tri(C6-C12)arylsilyl; more preferably, at least one selected from the group consisting of a (C1-C6)alkyl; a (C6-C20)aryl unsubstituted or substituted with at least one of a (C1-C6)alkyl(s), a (5- to 15-membered)heteroaryl(s), and a tri(C6-C12)arylsilyl(s); a (5- to 15-membered)heteroaryl unsubstituted or substituted with a (C6-C12)aryl(s); and an unsubstituted tri(C6-C12)arylsilyl, and for example, at least one selected from the group consisting of a methyl, a phenyl, a biphenyl, a terphenyl, a dimethylfluorenyl, a phenyl substituted with a dibenzofuranyl, a phenyl substituted with a carbazolyl, a phenyl substituted with a triphenylsilyl, a carbazolyl, a dibenzofuranyl, a dibenzothiophenyl, a phenylpyridyl, a phenylcarbazolyl, and a triphenylsilyl.

In the formulas of the present disclosure, if a substituent is linked to an adjacent substituent to form a ring or two adjacent substituents are linked to each other to form a ring, the ring may be a substituted or unsubstituted, mono- or polycyclic, (3- to 30-membered) alicyclic or aromatic ring, or the combination thereof, in which the formed ring may contain at least one heteroatom selected from B, N, O, S, Si, and P, preferably at least one heteroatom selected from N, O, and S. According to one embodiment of the present disclosure, the number of the ring backbone atoms is 5 to 20. According to another embodiment of the present disclosure, the number of the ring backbone atoms is 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, heteroaryl or heteroarylene may, each independently, contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

Hereinafter, the compounds represented by formulas 1 and 2 will be described in more detail.

In formula 1, $Y_1$ represents O, S, $CR_{11}R_{12}$, or $NR_{13}$.

Herein, $R_{11}$ and $R_{12}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30) cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or $R_{11}$ and $R_{12}$ may be linked to each other to form a spiro ring. According to one embodiment of the present disclosure, $R_{11}$ and $R_{12}$ each independently represent a substituted or unsubstituted (C1-C6)alkyl, or $R_{11}$ and $R_{12}$ may be linked to each other to form a spiro ring. According to another embodiment of the present disclosure, $R_{11}$ and $R_{12}$ each independently represent an unsubstituted (C1-C6)alkyl, or $R_{11}$ and $R_{12}$ may be linked to each other to form a spiro ring. Specifically, $R_{11}$ and $R_{12}$ each independently may be methyl, etc., or $R_{11}$ and $R_{12}$ may be linked to each other to form a fluorene ring to form a spiro fluorene structure. $R_{11}$ and $R_{12}$ may be the same or different, and according to one embodiment of the present disclosure, $R_{11}$ and $R_{12}$ are the same.

In formula 1, $R_1$ to $R_8$, and $R_{13}$ each independently represent $-L_1-(Ar_1)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl, with a proviso that one or more of $R_1$ to $R_8$, and $R_{13}$ is $-L_1-(Ar_1)_a$.

According to one embodiment of the present disclosure, $R_1$ to $R_8$ each independently represent $-L_1-(Ar_1)_a$, hydrogen, a substituted or unsubstituted (C6-C15)aryl, or a substituted or unsubstituted (5- to 20-membered)heteroaryl. According to another embodiment of the present disclosure, $R_1$ to $R_8$ each independently represent $-L_1-(Ar_1)_a$, hydrogen, a (C6-C15)aryl unsubstituted or substituted with one or more (C1-C6)alkyl, or a (5- to 20-membered)heteroaryl unsubstituted or substituted with one or more (C6-C12)aryl. Specifically, $R_1$ to $R_8$ each independently may be $-L_1-(Ar_1)_a$, hydrogen, phenyl, biphenyl, dimethylfluorenyl, carbazolyl, dibenzofuranyl, dibenzothiophenyl, phenylcarbazolyl, phenylbenzocarbazolyl, etc.

According to one embodiment of the present disclosure, $R_{13}$ represents $-L_1-(Ar_1)_a$, a substituted or unsubstituted (C6-C15)aryl, or a substituted or unsubstituted (5- to 15-membered)heteroaryl. According to another embodiment of the present disclosure, $R_{13}$ represents $-L_1-(Ar_1)_a$, an unsubstituted (C6-C15)aryl, or a (5- to 15-membered)heteroaryl unsubstituted or substituted with one or more (C6-C12)aryl. Specifically, $R_{13}$ may be $-L_1-(Ar_1)_a$, phenyl, biphenyl, dibenzofuranyl, phenylcarbazolyl, etc.

In formula 1, $L_1$ each independently represents a single bond, a substituted or unsubstituted (C6-C30)arylene, or a substituted or unsubstituted (3- to 30-membered)heteroarylene, where if a plurality of $L_1$'s are present, each of $L_1$ may be the same or different. According to one embodiment of the present disclosure, $L_1$ each independently represents a single bond, a substituted or unsubstituted (C6-C15)arylene, or a substituted or unsubstituted (5- to 20-membered)heteroarylene. According to another embodiment of the present disclosure, $L_1$ each independently represents a single bond, an unsubstituted (C6-C15)arylene, or an unsubstituted (5- to 20-membered)heteroarylene. Specifically, $L_1$ each independently may be a single bond, a phenylene, a biphenylene, a benzocarbazolylene, etc.

In formula 1, $Ar_1$ each independently represents a substituted or unsubstituted nitrogen-containing (3- to 30-membered)heteroaryl, where if a plurality of $Ar_1$'s are present, each of $Ar_1$ may be the same or different. According to one embodiment of the present disclosure, $Ar_1$ each independently represents a substituted or unsubstituted nitrogen-containing (5- to 15-membered)heteroaryl. According to another embodiment of the present disclosure, $Ar_1$ each independently represents a nitrogen-containing (5- to 15-membered)heteroaryl unsubstituted or substituted with a (C6-C20)aryl(s) or a (5- to 15-membered)heteroaryl(s). Specifically, $Ar_1$ each independently may be a diphenyltriazinyl, a triazinyl substituted with a phenyl and a biphenyl, a triazinyl substituted with a phenyl and a dibenzofuranylphenyl, a triazinyl substituted with a phenyl and a carbazolylphenyl, a triazinyl substituted with a biphenyl and a carbazolylphenyl, a triazinyl substituted with a phenyl and a triphenylsilylphenyl, a triazinyl substituted with a phenyl and a dibenzofuranyl, a triazinyl substituted with a terphenyl and a dibenzofuranyl, a triazinyl substituted with a terphenyl and a dibenzothiophenyl, a triazinyl substituted with two dibenzofuranyls, a quinazolinyl substituted with a phenyl, a quinoxalinyl substituted with a phenyl, etc.

In formula 1, a represents an integer of 1 to 4, where if a is an integer of 2 or more, each of $Ar_1$ may be the same or different, and where if a plurality of a's are present, each of a may be the same or different.

According to one embodiment of the present disclosure, formula 1 may be represented by at least one of the following formulas 1-1 to 1-5.

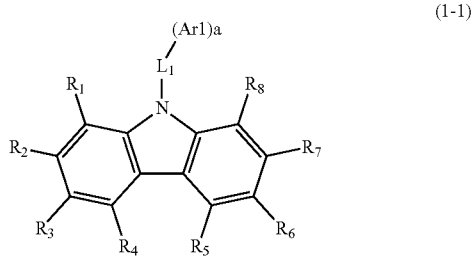

(1-1)

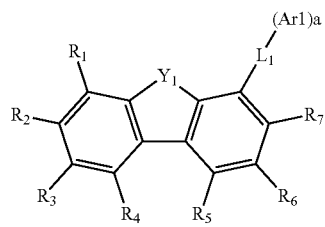

(1-2)

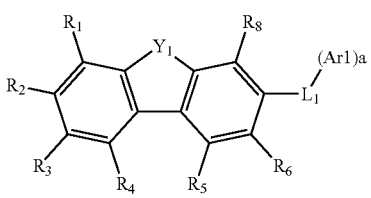

(1-3)

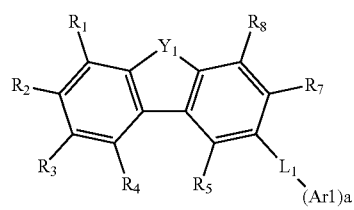

(1-4)

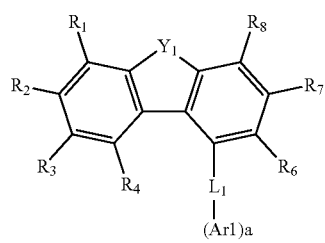

(1-5)

wherein $Y_1$ represents O, S, $CR_{11}R_{12}$, or $NR_{13}$;

$R_1$ to $R_8$, and $R_{13}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl; and $L_1$, $Ar_1$, a, $R_{11}$, and $R_{12}$ are as defined in formula 1.

According to one embodiment of the present disclosure, in formula 1, $Ar_1$ each independently may be a substituted or unsubstituted pyridyl, a substituted or unsubstituted pyrazinyl, a substituted or unsubstituted pyrimidinyl, a substituted or unsubstituted pyridazinyl, a substituted or unsubstituted triazinyl, a substituted or unsubstituted quinolyl, a substituted or unsubstituted isoquinolyl, a substituted or unsubstituted cinnolinyl, a substituted or unsubstituted quinazolinyl, a substituted or unsubstituted quinoxalinyl, or a substituted or unsubstituted naphthyridinyl, etc.

In formula 2, $Ar_2$ represents hydrogen, deuterium, a halogen, a cyano, a substituted or unsubstituted (C1-C30) alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl. According to one embodiment of the present disclosure, $Ar_2$ represents a substituted or unsubstituted (C6-C20)aryl, or a substituted or unsubstituted (5- to 15-membered)heteroaryl. According to another embodiment of the present disclosure, $Ar_2$ represents a (C6-C20)aryl unsubstituted or substituted with a (C1-C6)alkyl(s) or a (5- to 15-membered) heteroaryl(s): or a (5- to 15-membered)heteroaryl unsubstituted or substituted with one or more (C6-C12)aryl. Specifically, $Ar_2$ may be a phenyl, a naphthyl, a biphenyl, a terphenyl, a triphenylenyl, a phenyl substituted with a dimethylfluorenyl, a phenyl substituted with a phenylpyridyl, a phenyl substituted with a carbazolyl, a phenyl substituted with a dibenzofuranyl, a dimethylfluorenyl, a dibenzofuranyl, a dibenzothiophenyl, a carbazolyl substituted with a phenyl, etc.

In formula 2, $X_1$ and $X_2$ each independently represent N or CH, with a proviso that one or more of $X_1$ and $X_2$ is N.

In formula 2, at least one of $R_{21}$ and $R_{22}$, $R_{22}$ and $R_{23}$, $R_{23}$ and $R_{24}$, $R_{25}$ and $R_{26}$, $R_{26}$ and $R_{27}$, and $R_{27}$ and $R_{28}$ are fused in each two * positions of the following formula to form a ring of the following formula.

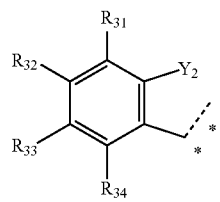

the remainders of $R_{21}$ to $R_{28}$ which do not form a ring and $R_{31}$ to $R_{34}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl, where if a plurality of $R_{31}$'s to $R_{34}$'s are present, each of $R_{31}$, each of $R_{32}$, each of $R_{33}$, and each of $R_{34}$ may be the same or different.

According to one embodiment of the present disclosure, the remainders of $R_{21}$ to $R_{28}$ which do not form a ring each independently represent hydrogen, a substituted or unsubstituted (C6-C15)aryl, or a substituted or unsubstituted (5- to 15-membered)heteroaryl. According to another embodiment of the present disclosure, the remainders of $R_{21}$ to $R_{28}$ which do not form a ring each independently represent hydrogen, an unsubstituted (C6-C15)aryl, or an unsubstituted (5- to 15-membered)heteroaryl. Specifically, the remainders of $R_{21}$ to $R_{28}$ which do not form a ring each independently may be hydrogen, a phenyl, a biphenyl, a dibenzofuranyl, etc.

According to one embodiment of the present disclosure, $R_{31}$ to $R_{34}$ each independently represent hydrogen, or a substituted or unsubstituted (C6-C12)aryl. According to another embodiment of the present disclosure, $R_{31}$ to $R_{34}$ each independently represent hydrogen, or an unsubstituted (C6-C12)aryl. Specifically, $R_{31}$ to $R_{34}$ each independently may be hydrogen, a phenyl, etc.

In formula 2, $Y_2$ represents O, S, $CR_{14}R_{15}$, or $NR_{16}$, where if a plurality of $Y_2$'s are present, each of $Y_2$ may be the same or different.

Herein, $R_{14}$ and $R_{15}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30) cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or $R_{14}$ and $R_{15}$ may be linked to each other to form a spiro ring. $R_{14}$ and $R_{15}$ may be the same or different. According to one embodiment of the present disclosure, $R_{14}$ and $R_{15}$ are the same.

In addition, $R_{16}$ represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl. According to one embodiment of the present disclosure, $R_{16}$ represents a substituted or unsubstituted (C6-C20)aryl, or a substituted or unsubstituted (5- to 15-membered)heteroaryl. According to another embodiment of the present disclosure, $R_{16}$ represents a (C6-C20)aryl unsubstituted or substituted with one or more (5- to 20-membered)heteroaryl, or a (5- to 15-membered)heteroaryl unsubstituted or substituted with one or more (C6-C12)aryl. Specifically, $R_{16}$ may be a phenyl, a biphenyl, a terphenyl, a naphthylphenyl, a phenyl substituted with a carbazolyl, a phenyl substituted with a dibenzofuranyl, a phenyl substituted with a phenylcarbazolyl, a dibenzofuranyl, a pyridyl substituted with a phenyl, a pyrimidinyl substituted with a phenyl, a diphenylpyrimidinyl, etc.

According to one embodiment of the present disclosure, formula 2 may be represented by at least one of the following formulas 2-1 to 2-6.

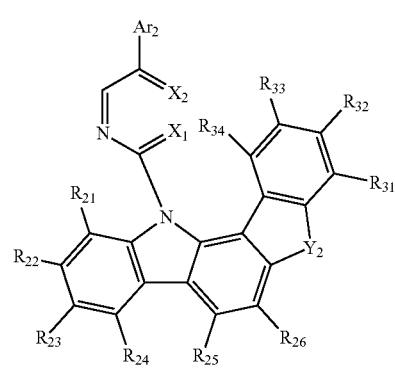

(2-1)

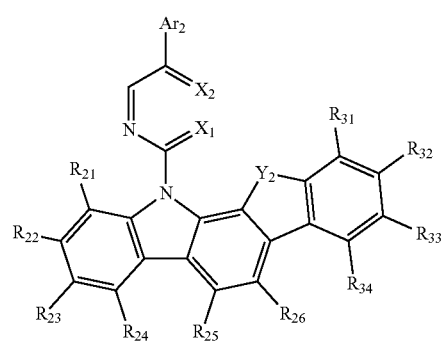

(2-2)

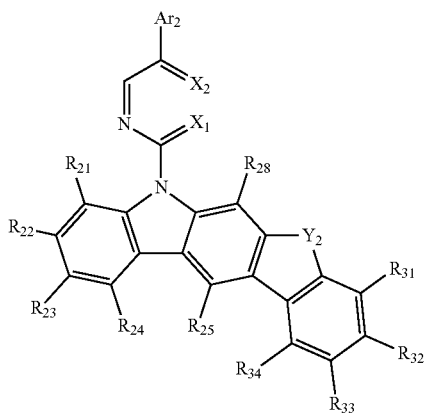

(2-3)

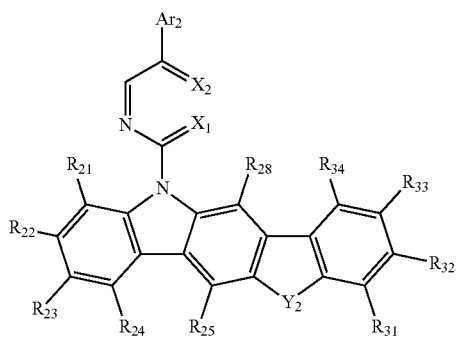

(2-4)

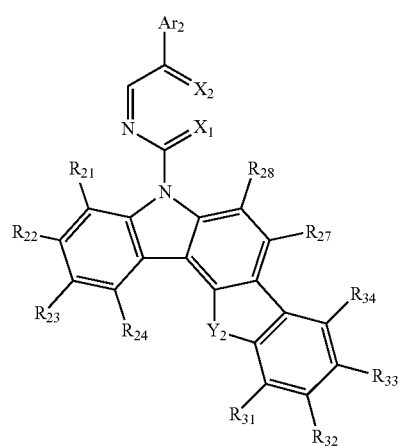

(2-5)

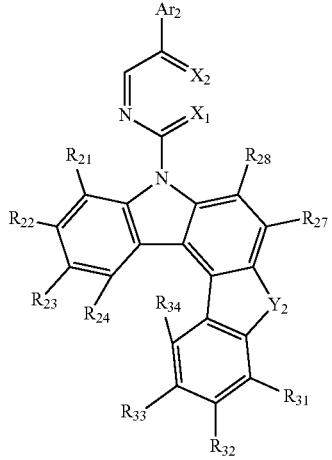

(2-6)

wherein $R_{21}$ to $R_{28}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl; and $Y_2$, $X_1$, $X_2$, $Ar_2$, and $R_{31}$ to $R_{34}$ are as defined in formula 2.

According to one embodiment of the present disclosure, in formula 2, $Ar_2$ each independently represents a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted triphenylenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrmidinyl, a substituted or unsubstituted fluorenyl, a substituted or unsubstituted benzofluorenyl, a substituted or unsubstituted diphenylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyldibenzofuranylamino, etc.

The compound represented by formula 1 includes the following compounds, but is not limited thereto.

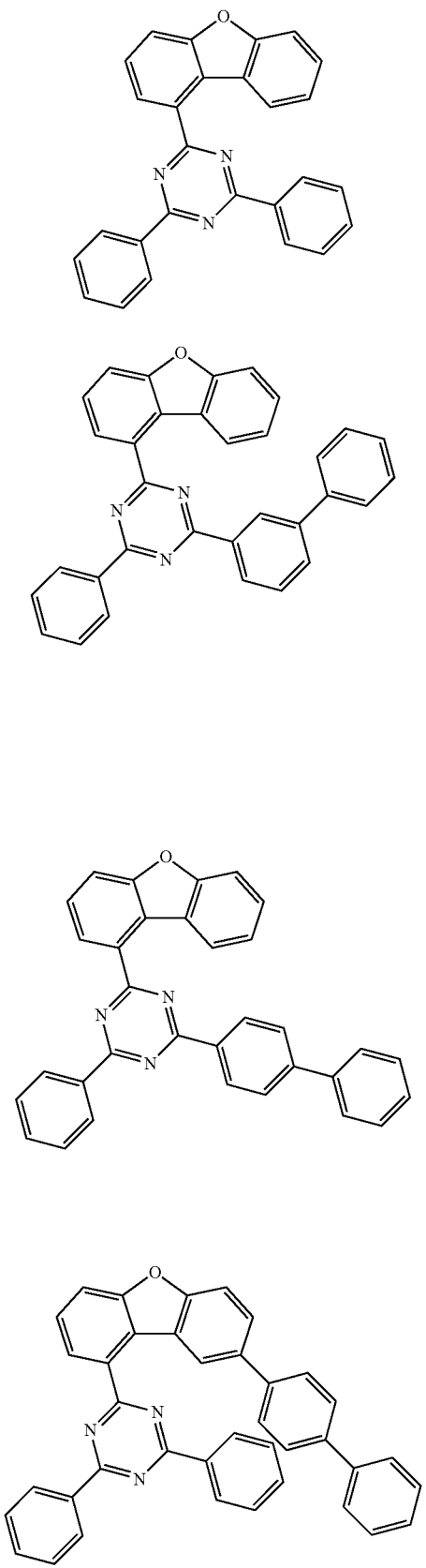
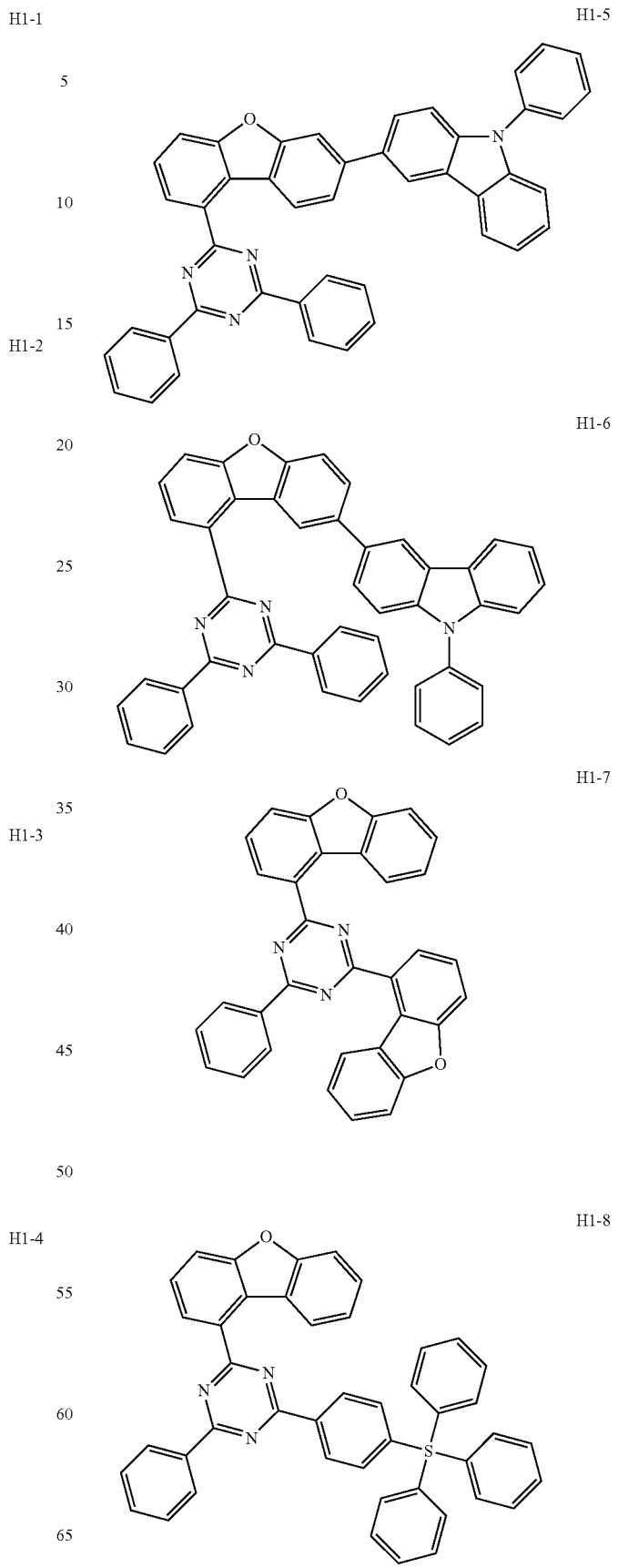

H1-9
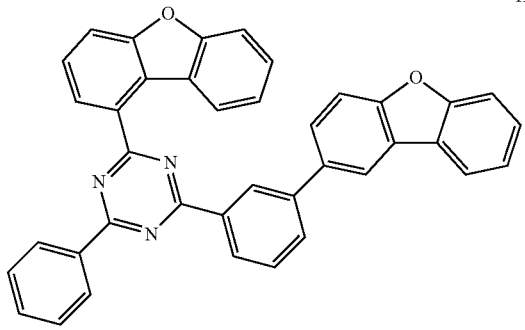
H1-10
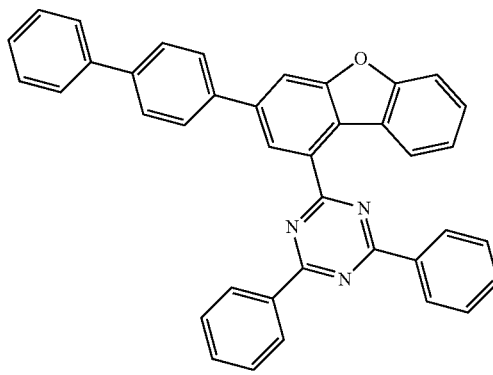
H1-11
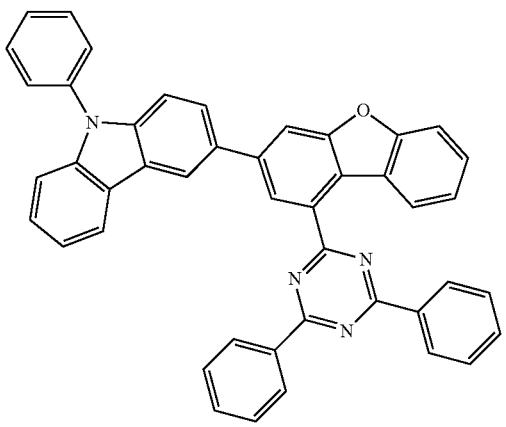
H1-12
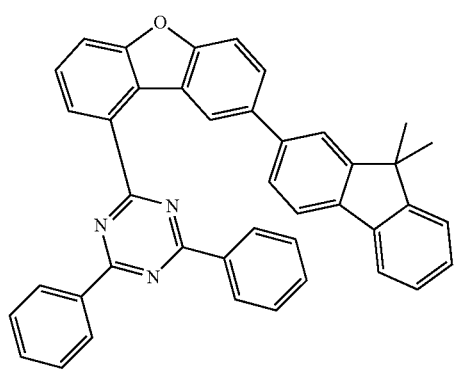
H1-13
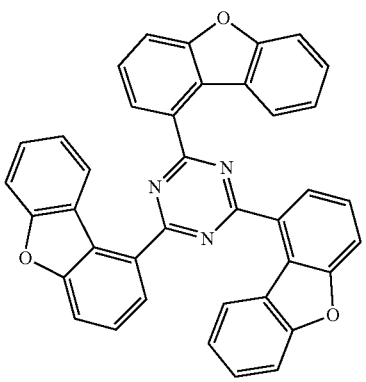
H1-14
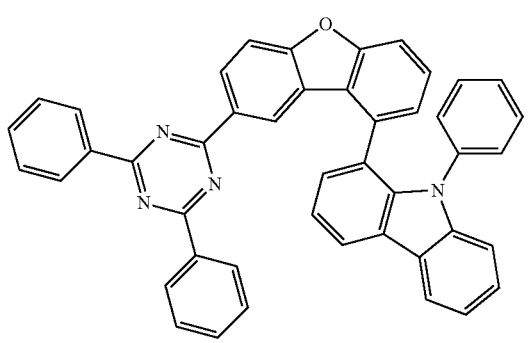
H1-15
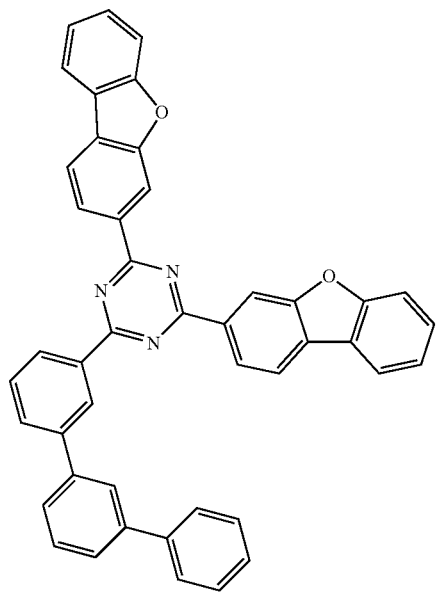

-continued
H1-16
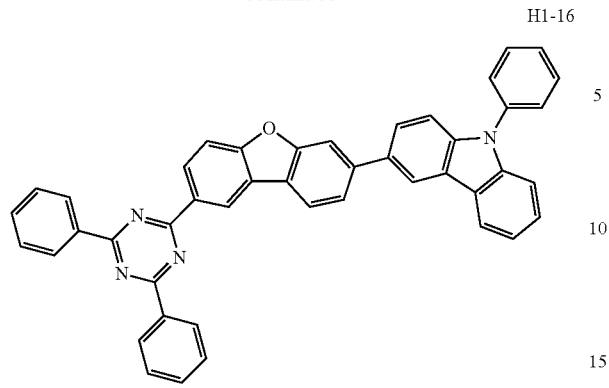
H1-17
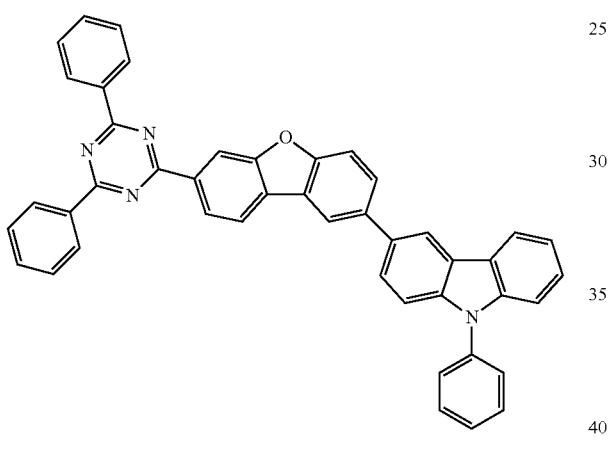
H1-18
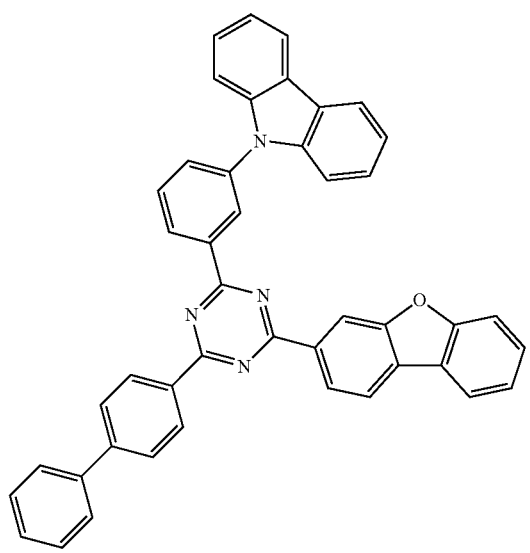
-continued
H1-19
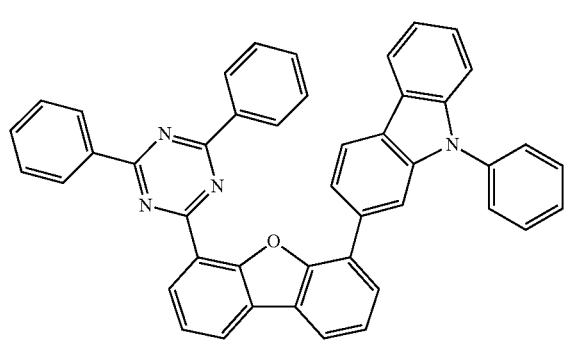
H1-20
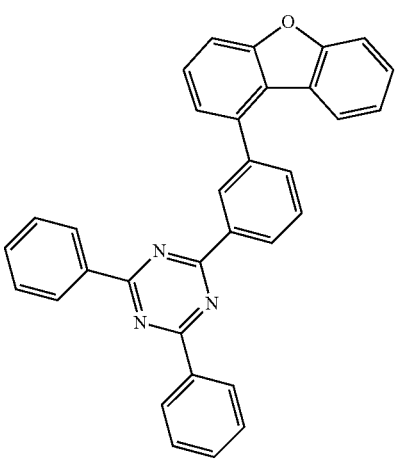
H1-21
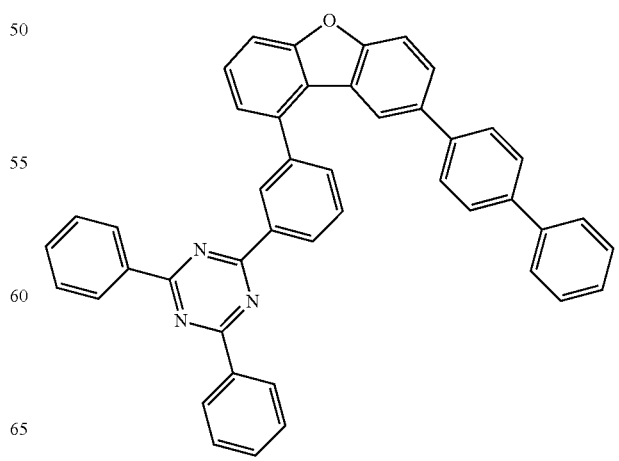

H1-22
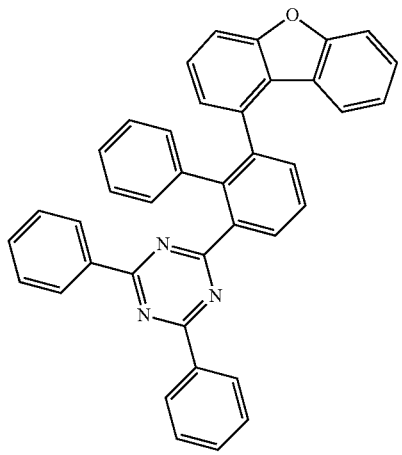
H1-23
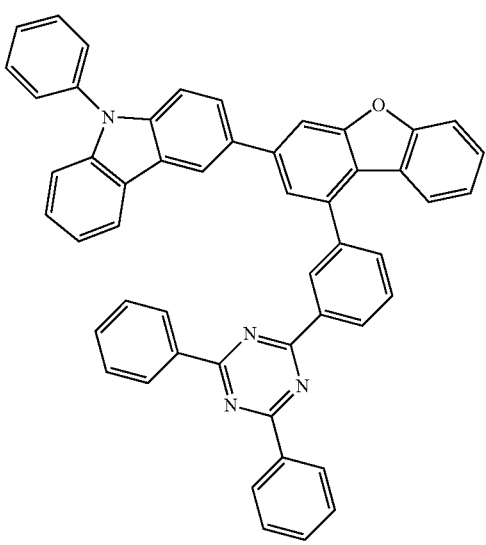
H1-24
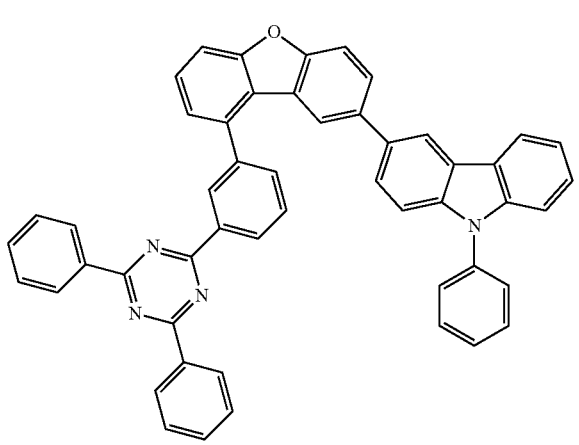
H1-25
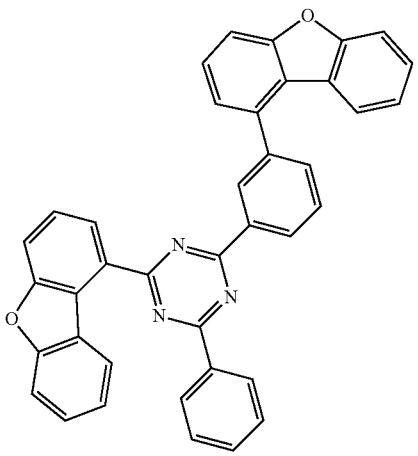
H1-26
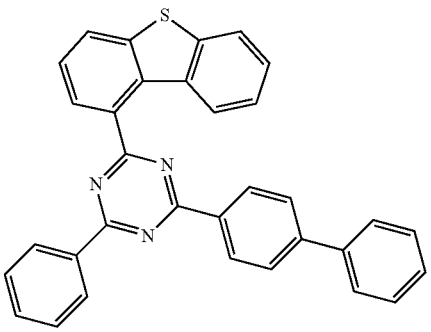
H1-27
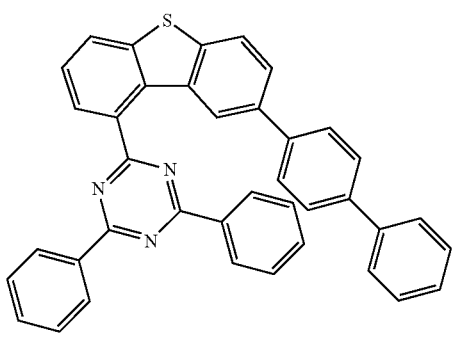

H1-28
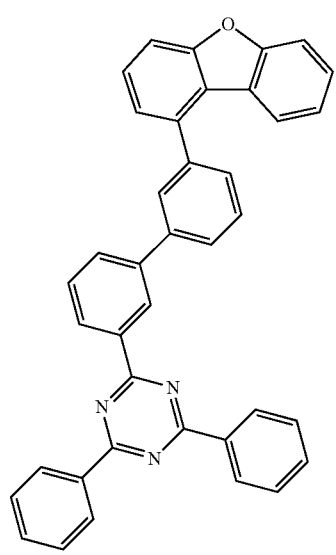
H1-29
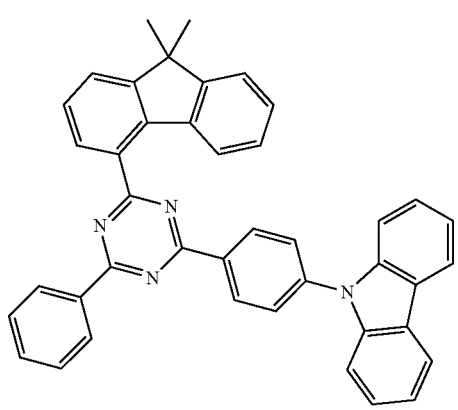
H1-30
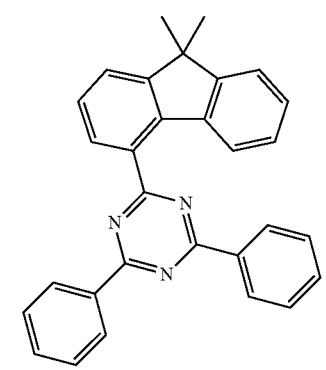
H1-31
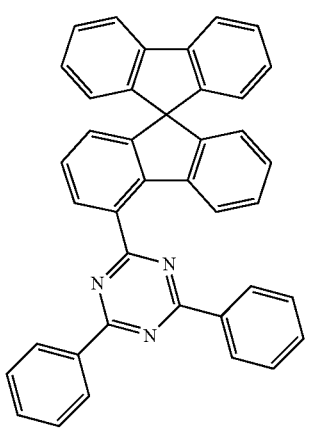
H1-32
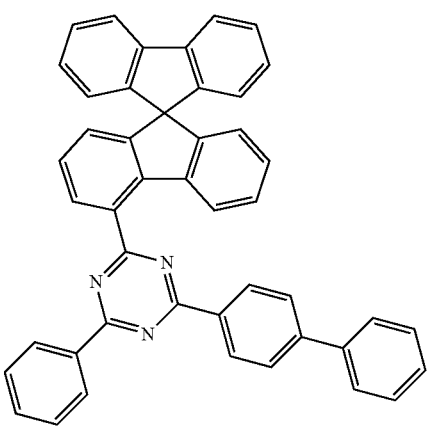
H1-33
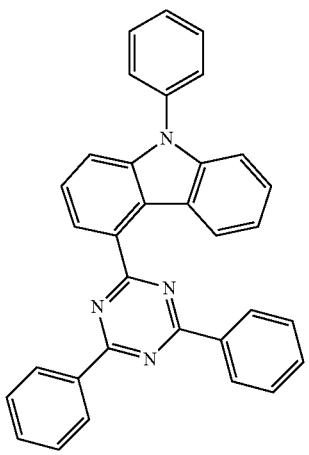

H1-34
H1-35
H1-36
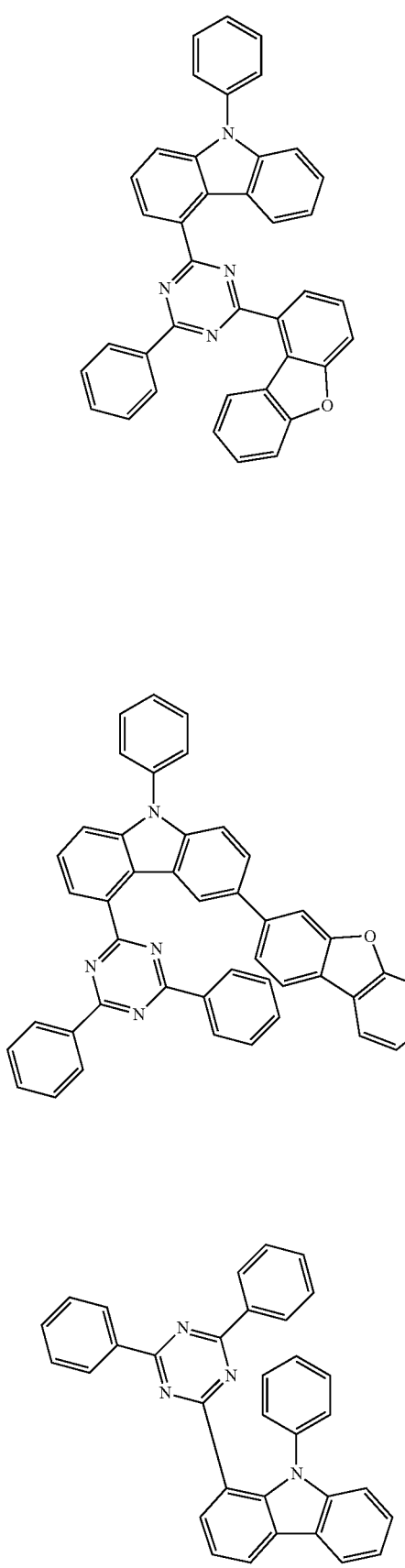
H1-37
H1-38
H1-39
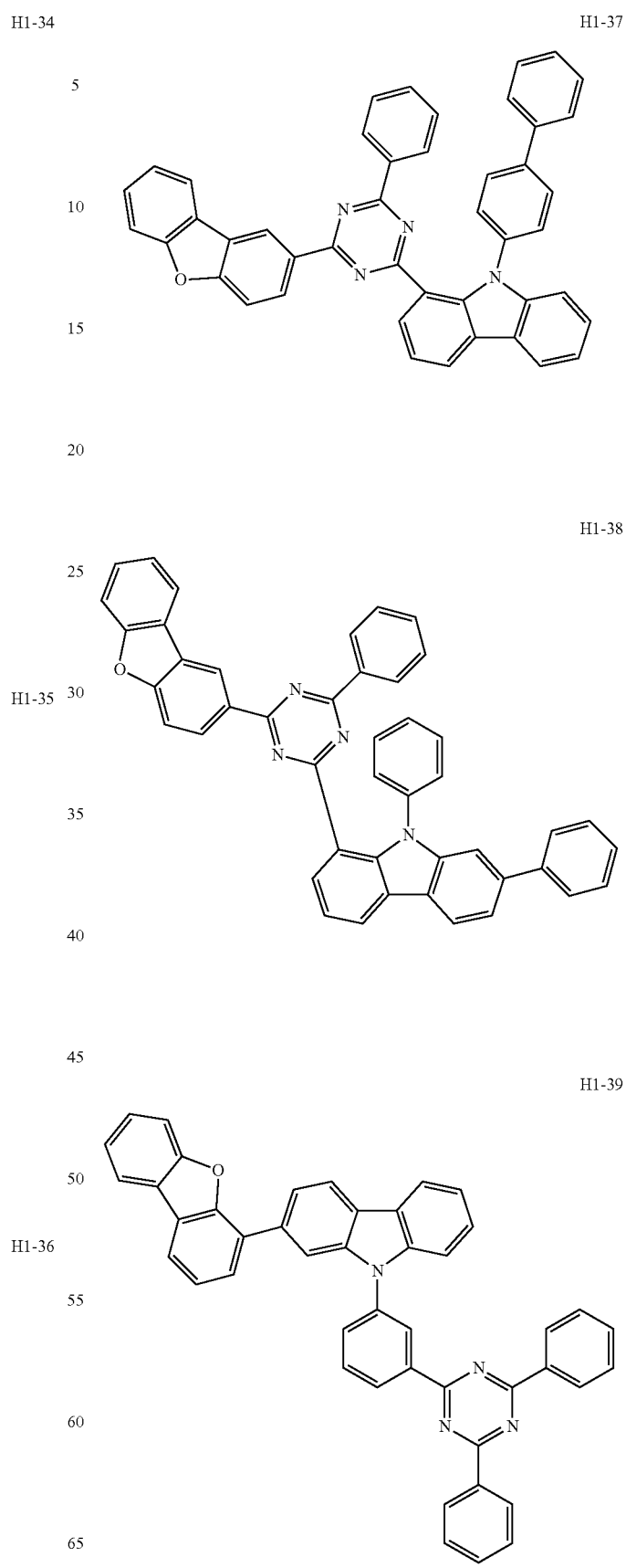

H1-40
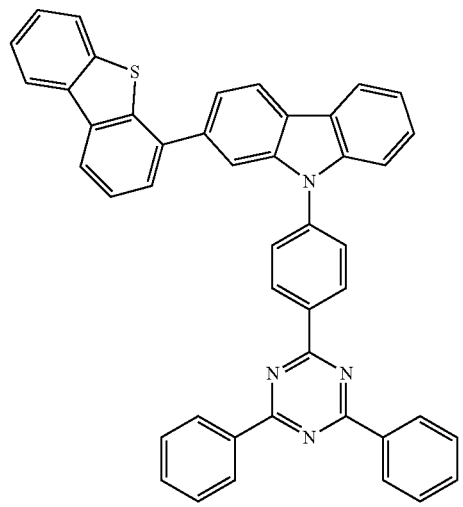
H1-41
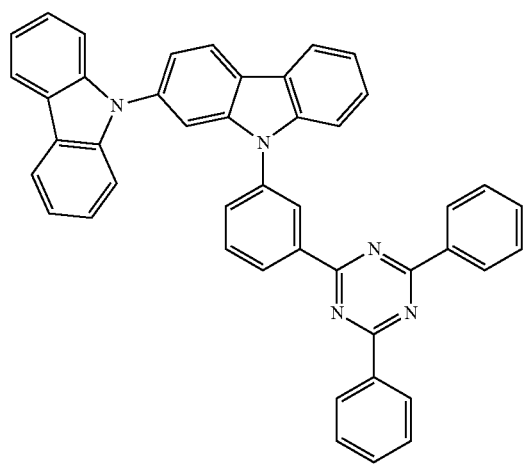
H1-42
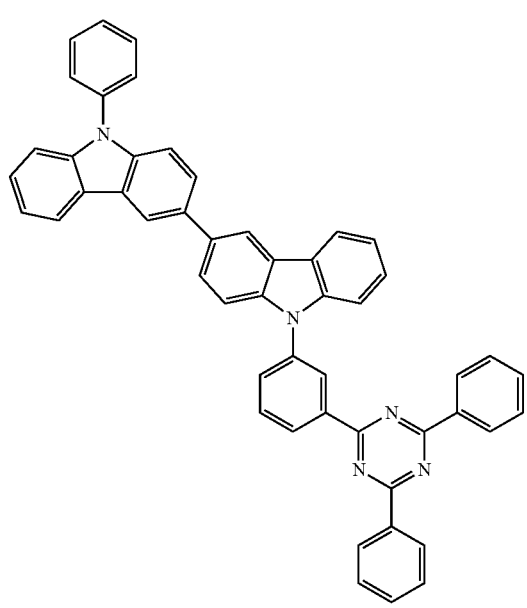
H1-43
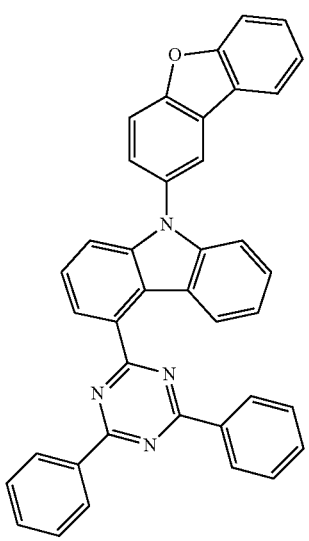
H1-44
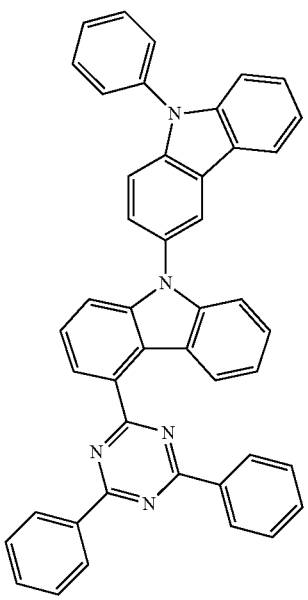
H1-45
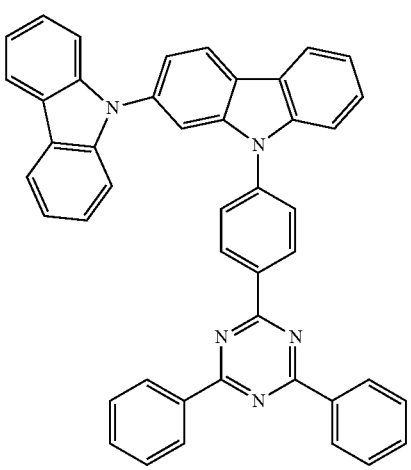

H1-46
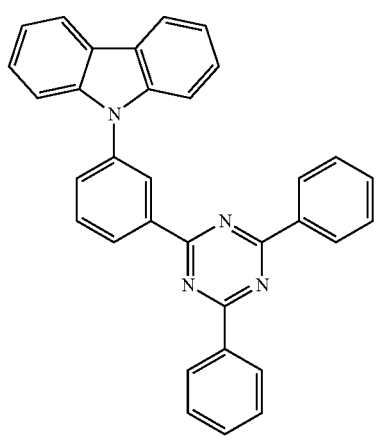
H1-47
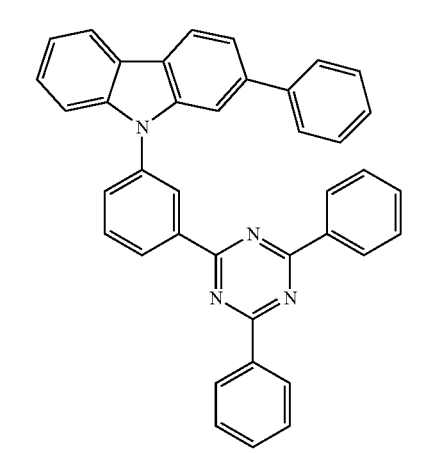
H1-48
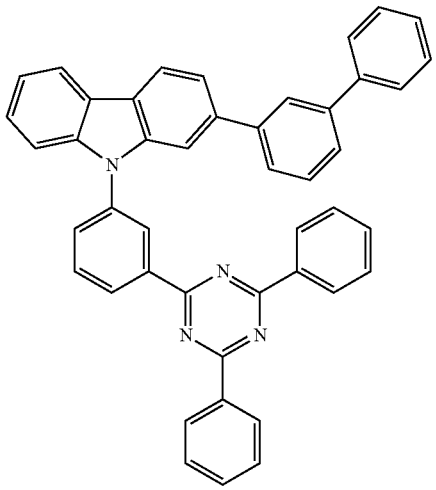
H1-49
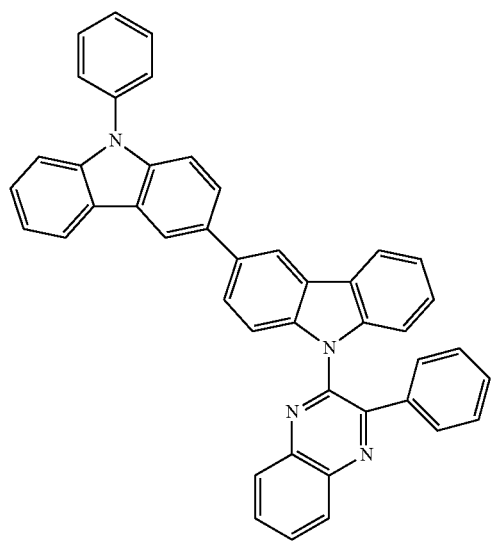
H1-50
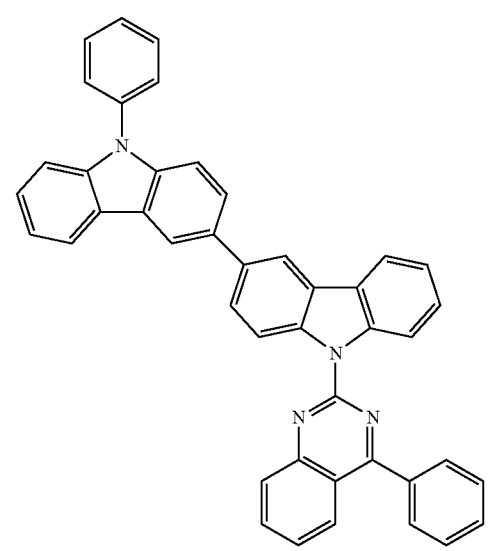
H1-51
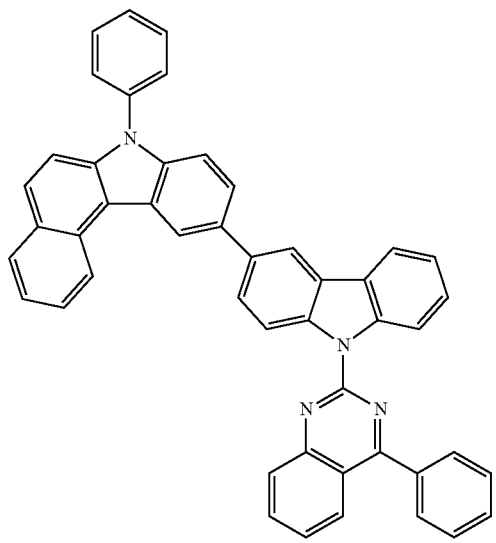

-continued
H1-52
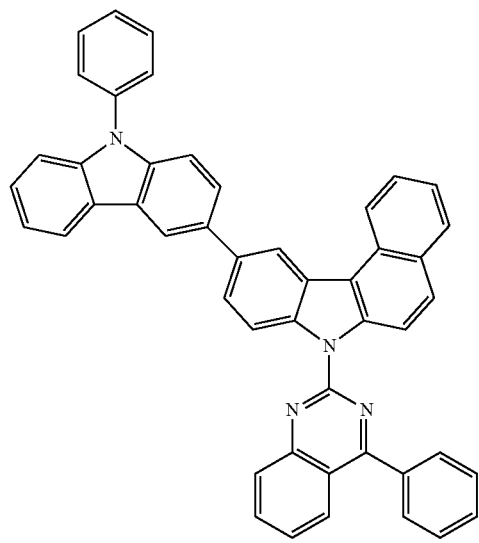
H1-55
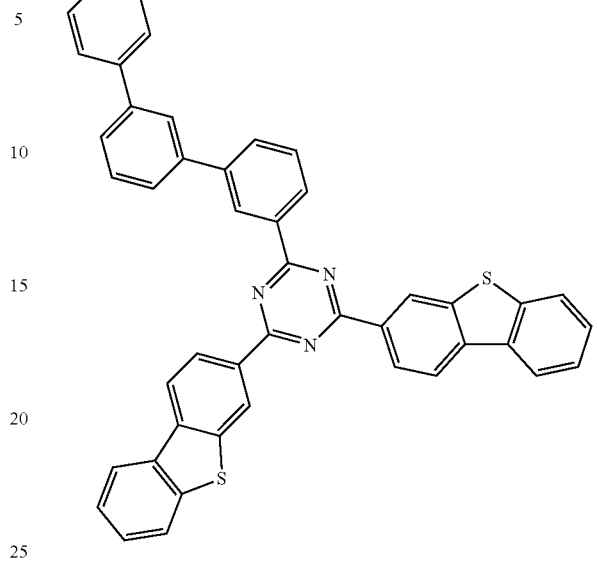
H1-53
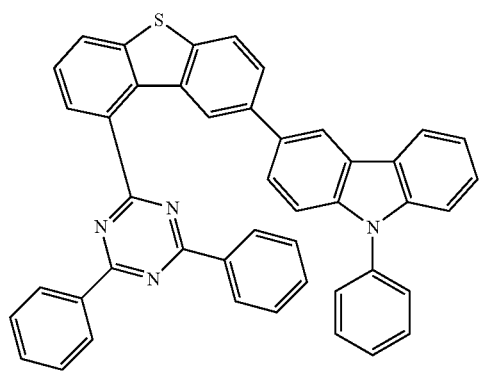
H1-54
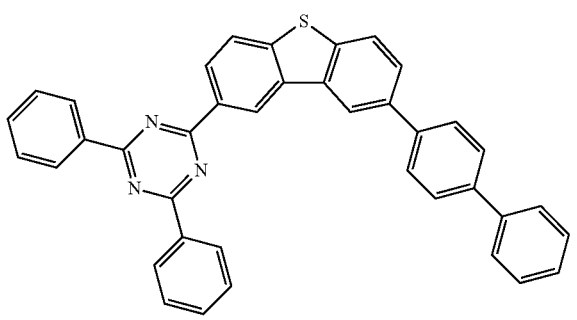
H1-56
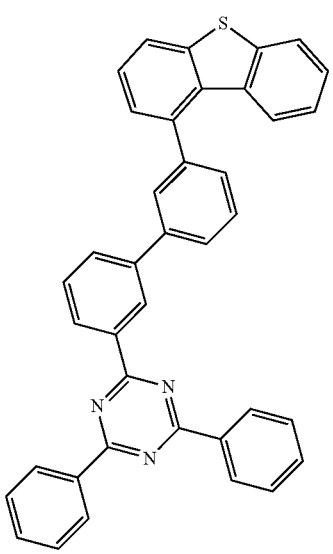

H1-57
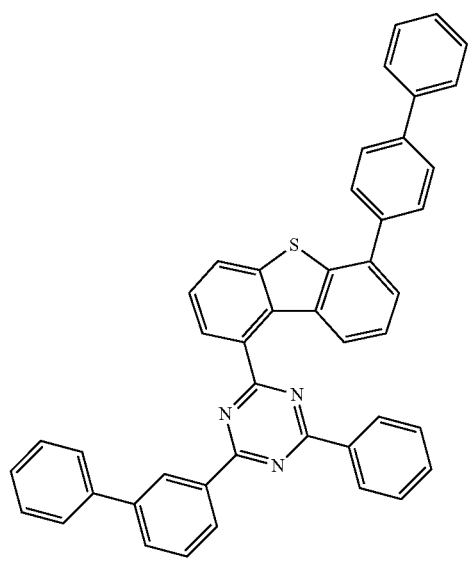
The compound represented by formula 2 includes the following compounds, but is not limited thereto.
H2-1
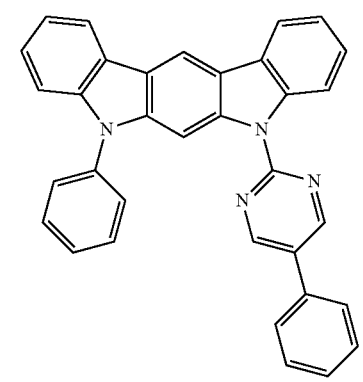
H2-2
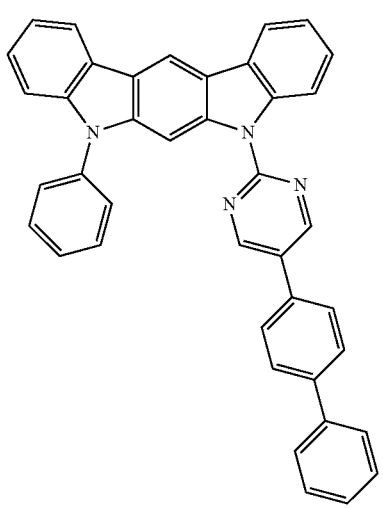
H2-3
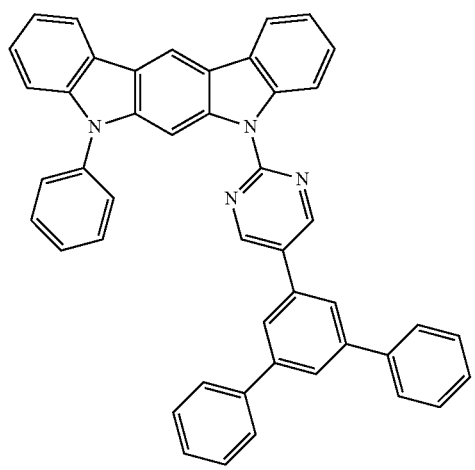
H2-4
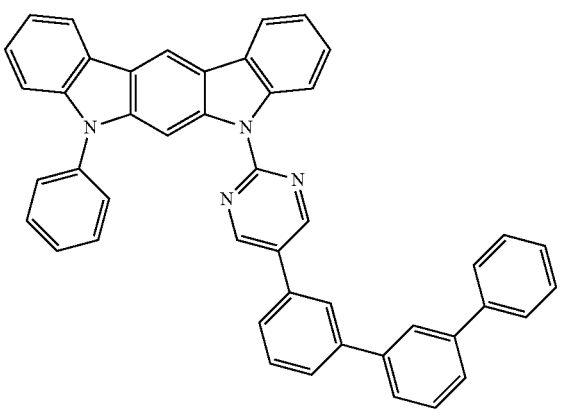
H2-5
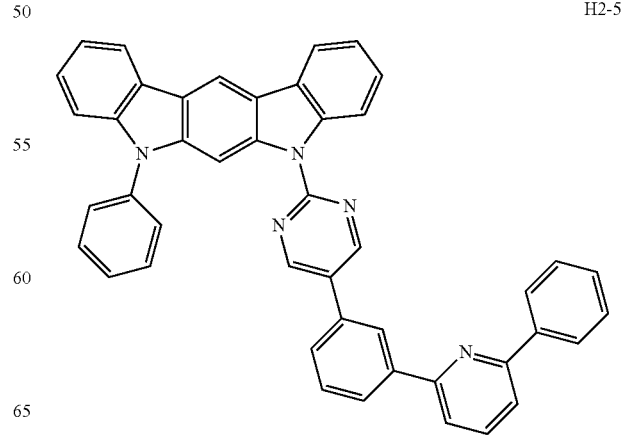

35
-continued
H2-6
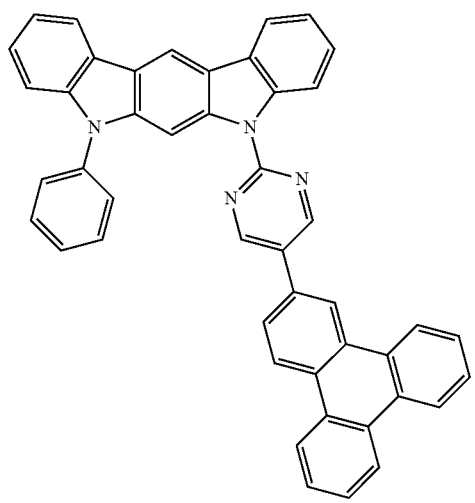
H2-7
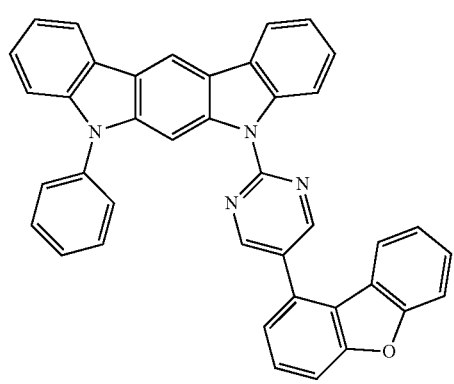
H2-8
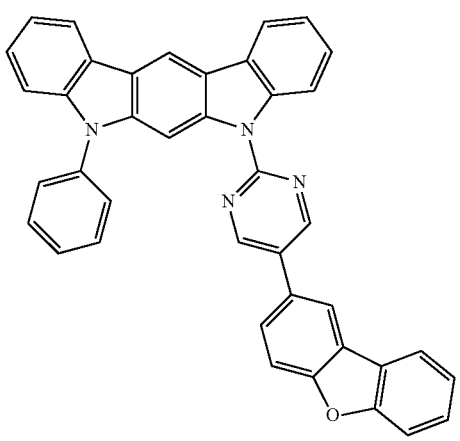
36
-continued
H2-9
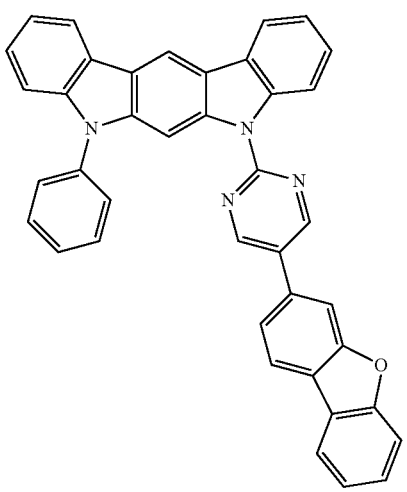
H2-10
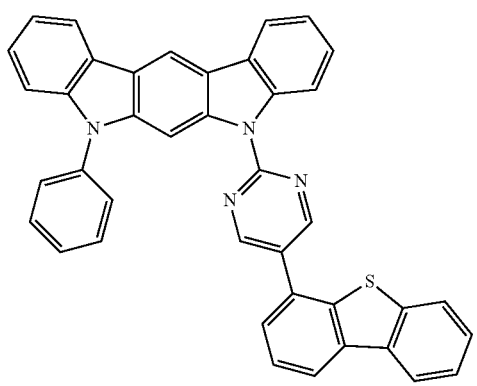
H2-11
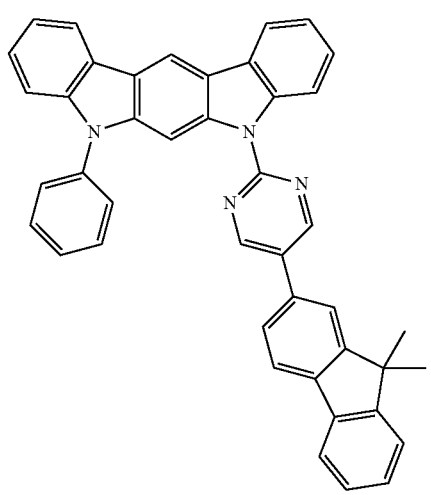

H2-12
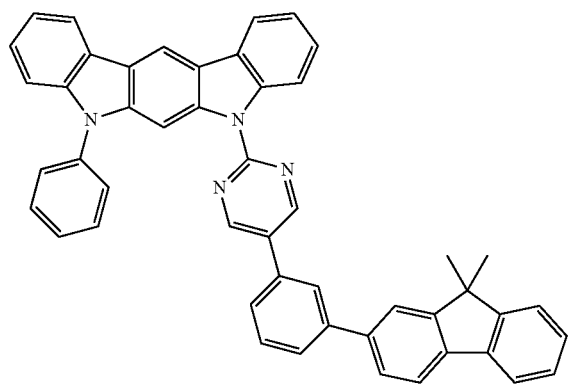
H2-13
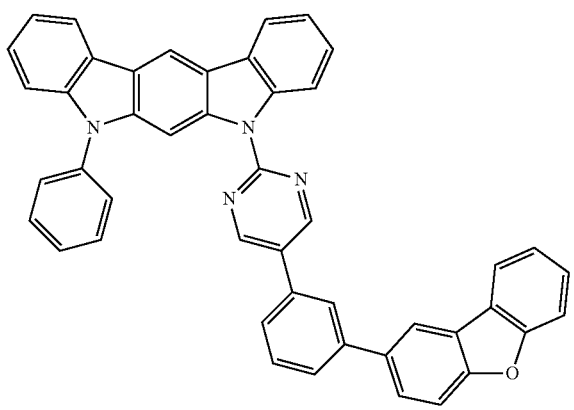
H2-14
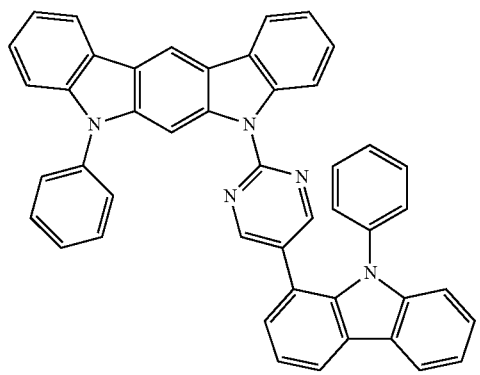
H2-15
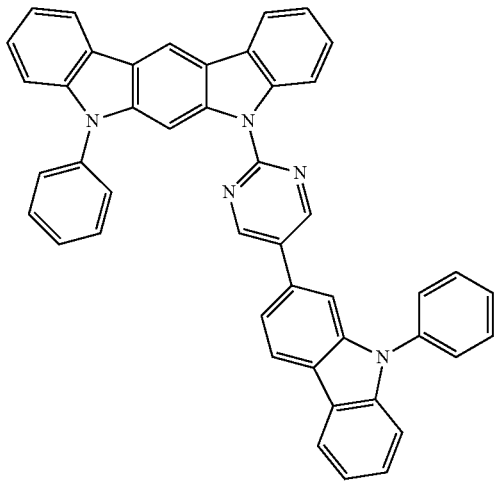
H2-16
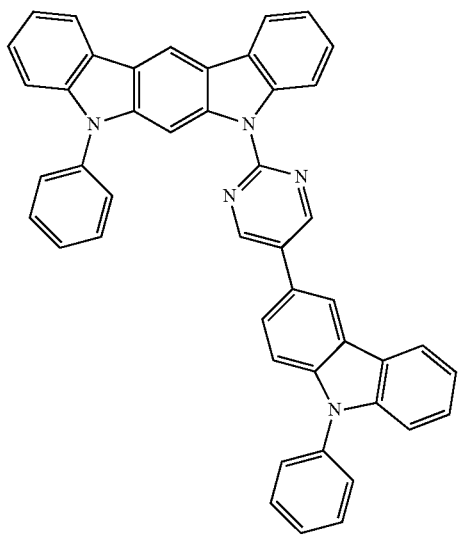
H2-17
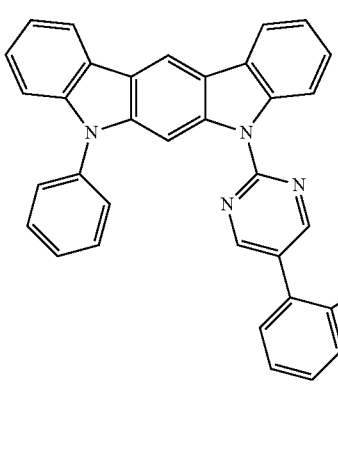

H2-18
H2-19
H2-20
H2-21
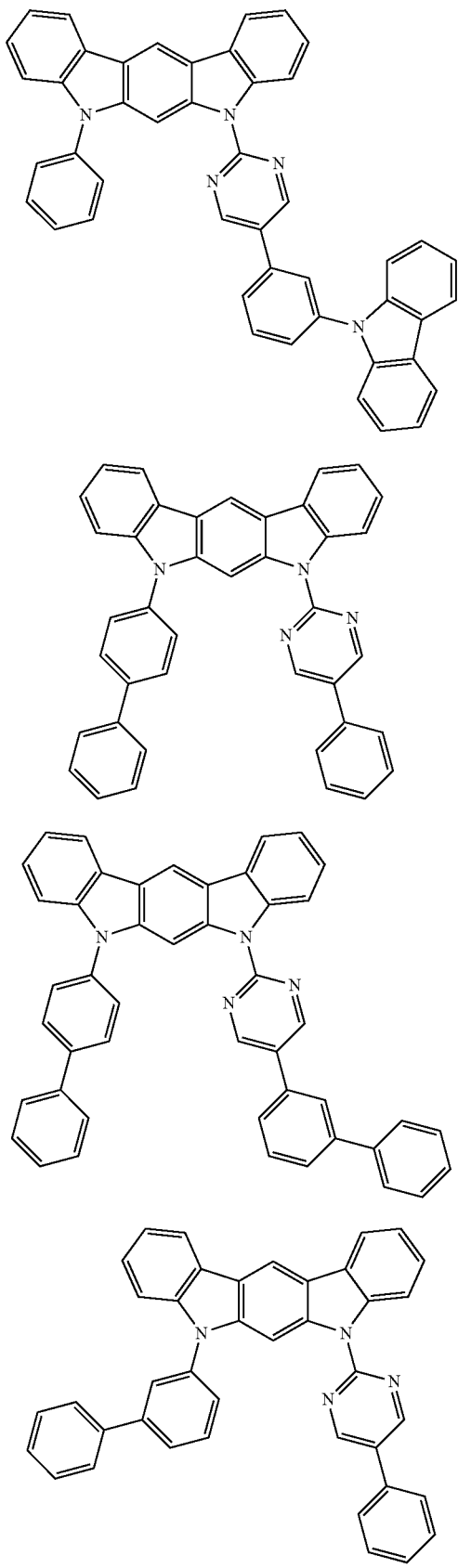
H2-22
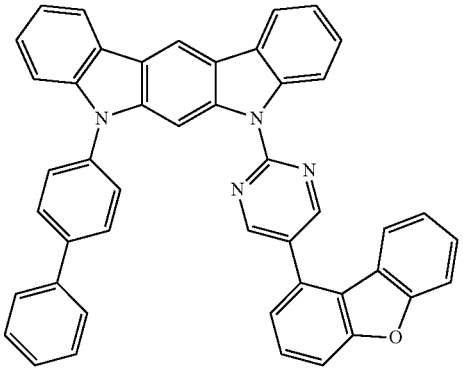
H2-23
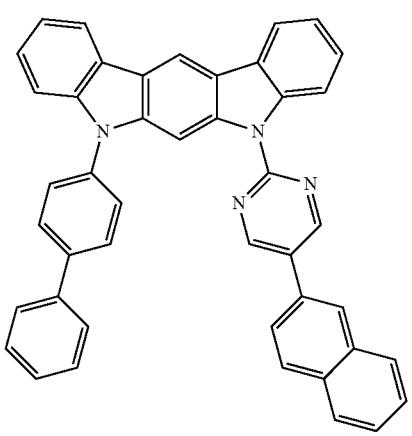
H2-24
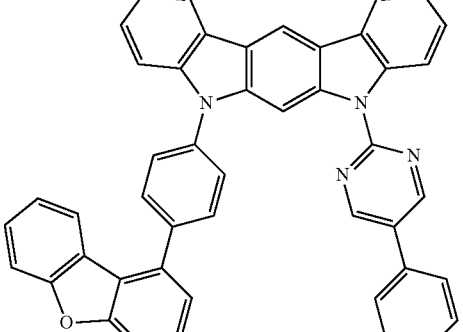
H2-25
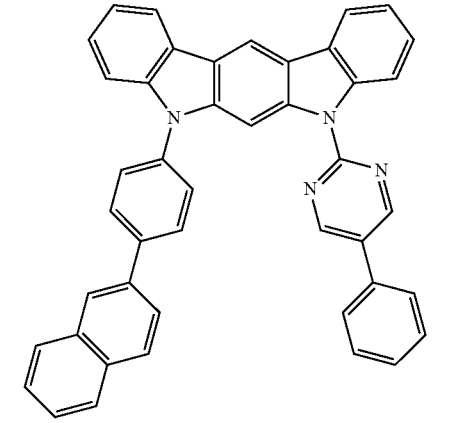

H2-26
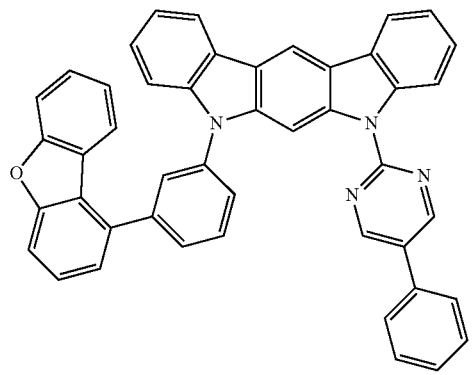
H2-27
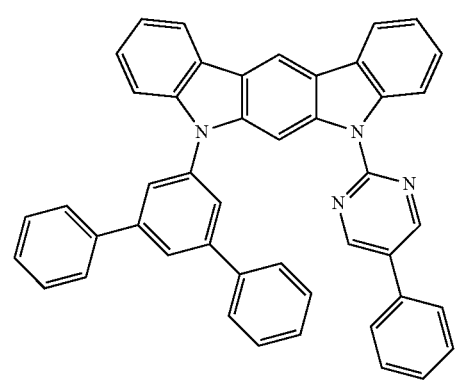
H2-28
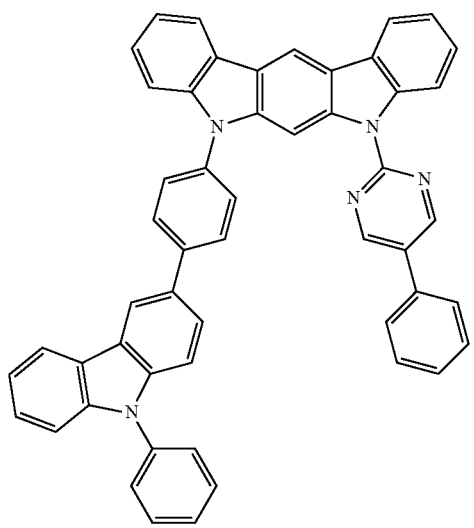
H2-29
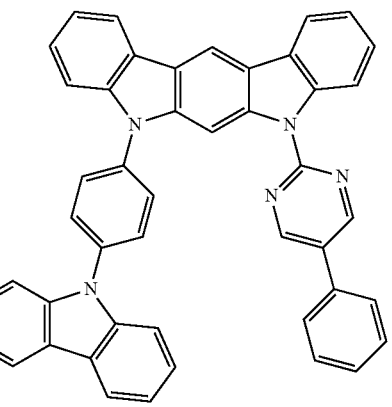
H2-30
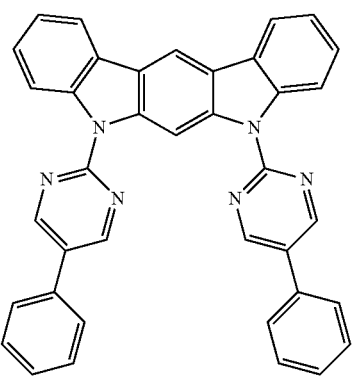
H2-31
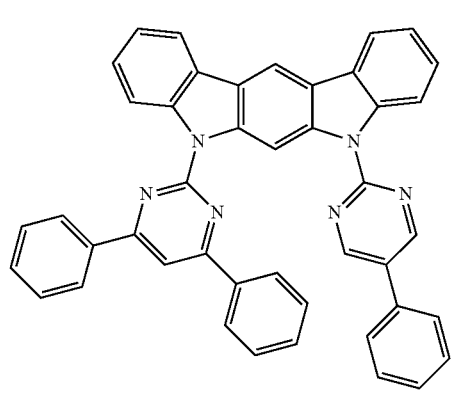
H2-32
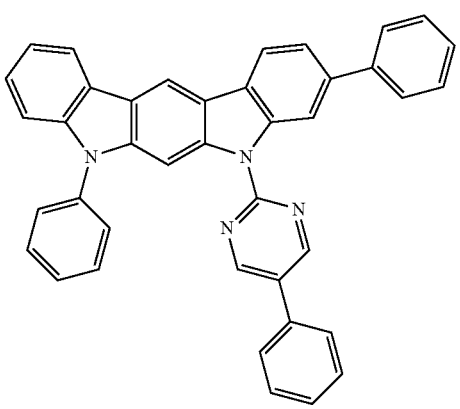

H2-33
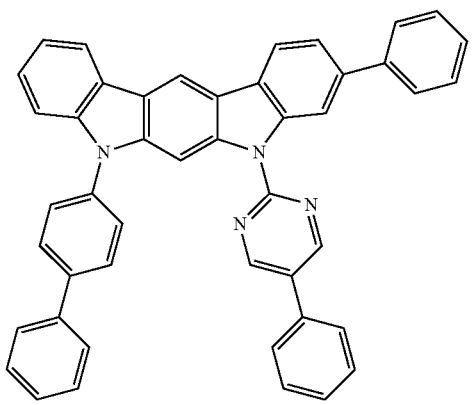
H2-34
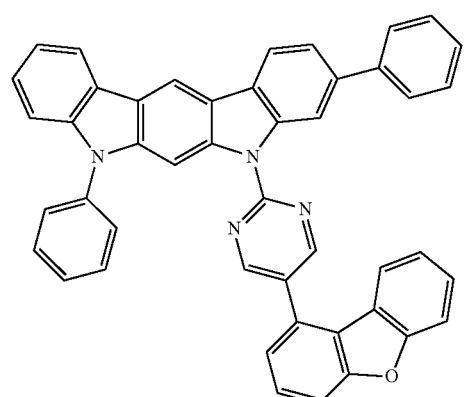
H2-35
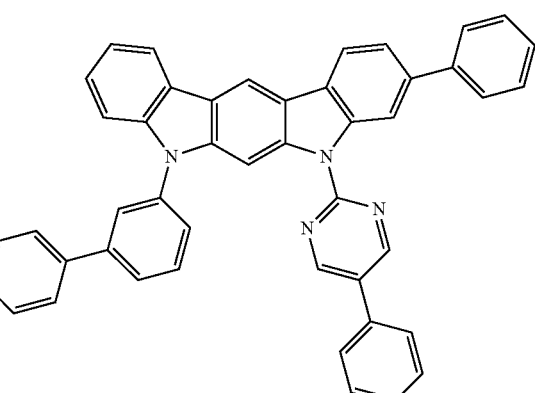
H2-36
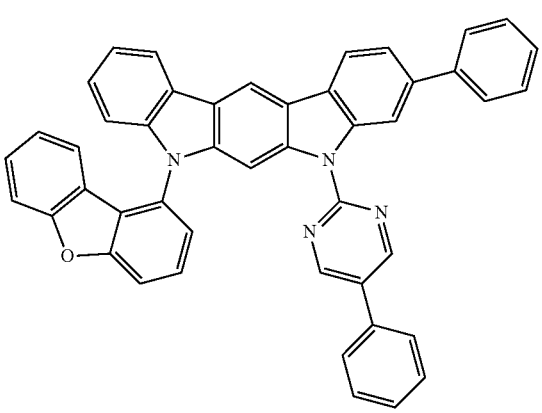
H2-37
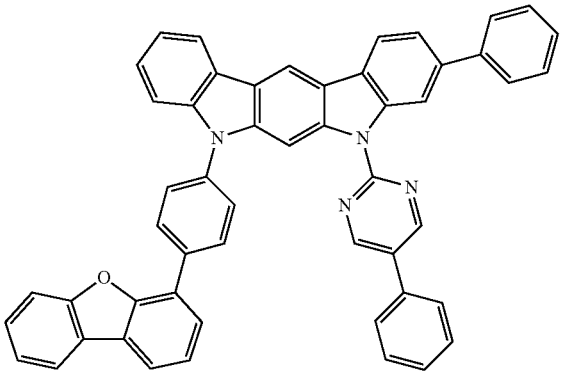
H2-38
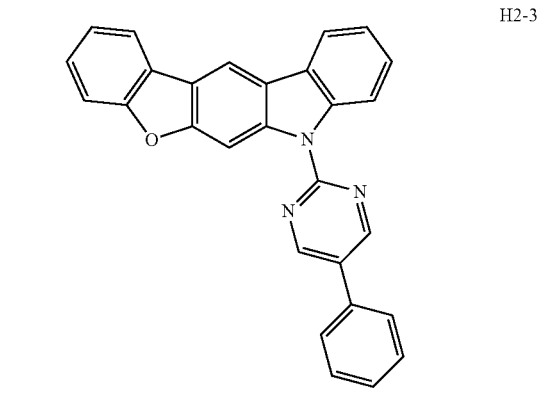
H2-39
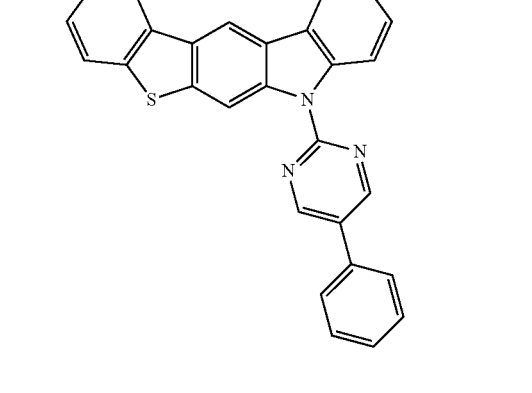
H2-40
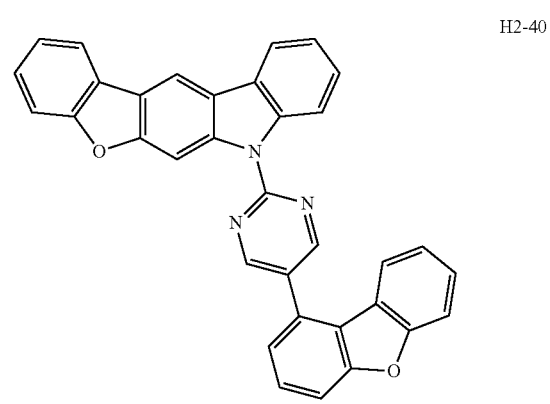

H2-41
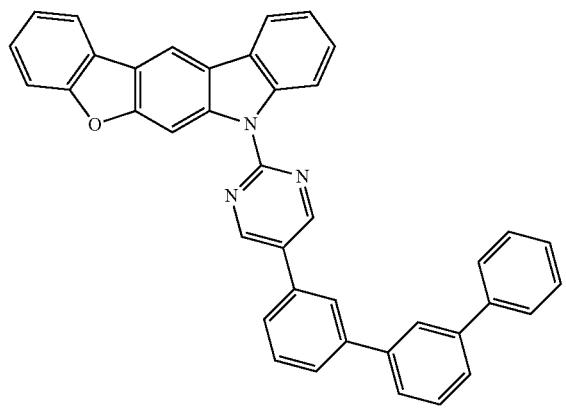
H2-42
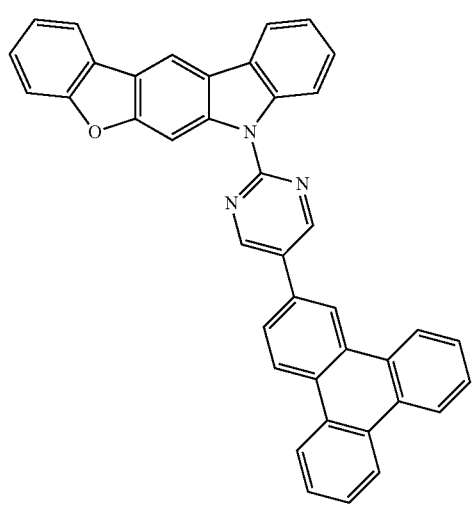
H2-43
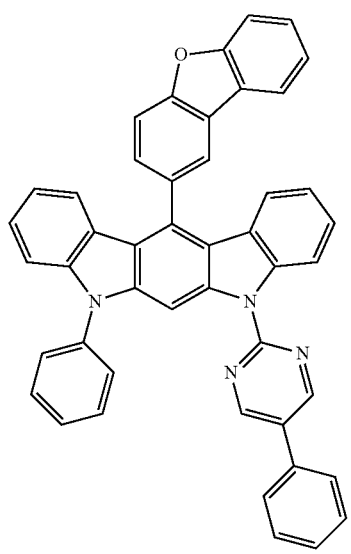
H2-44
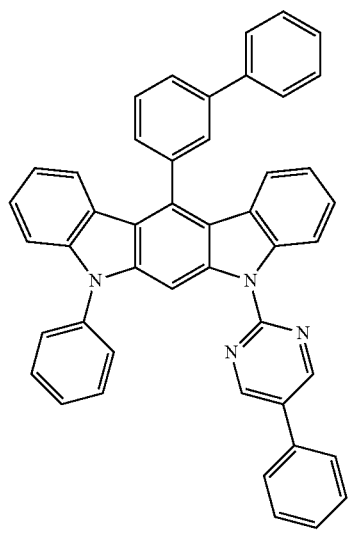
H2-45
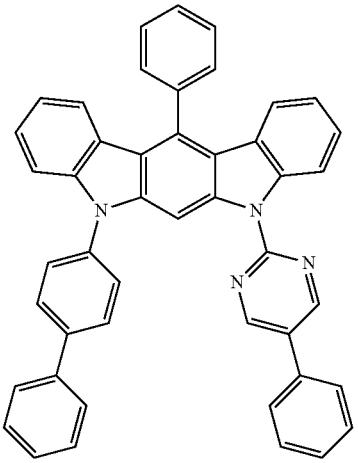
H2-46
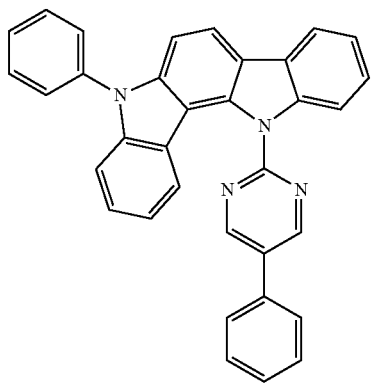

H2-47
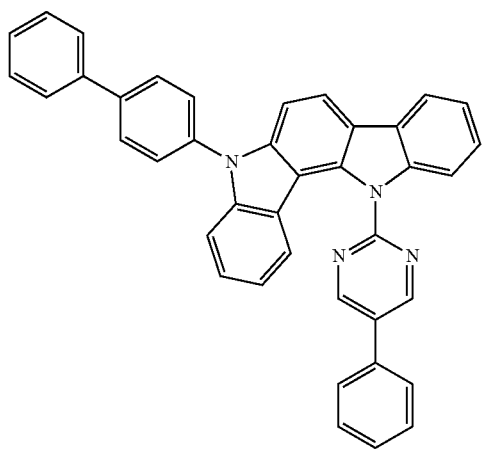
H2-48
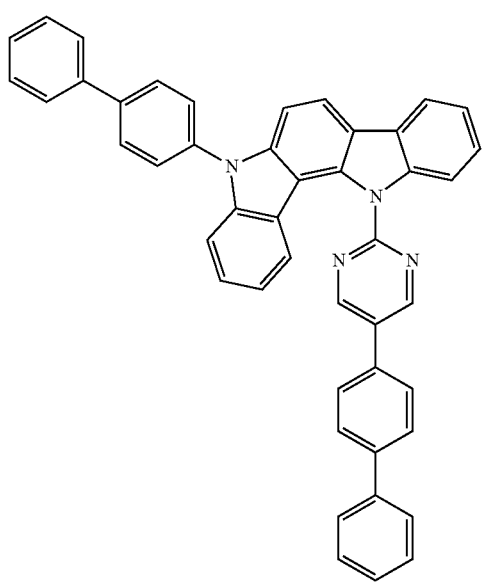
H2-49
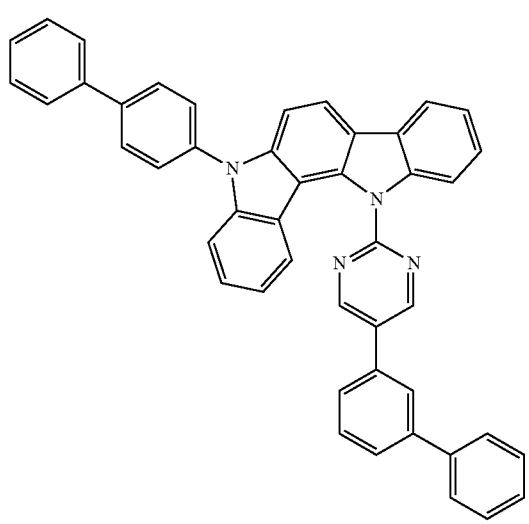
H2-50
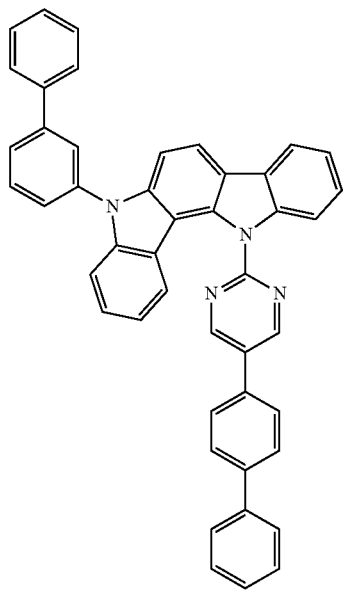
H2-51
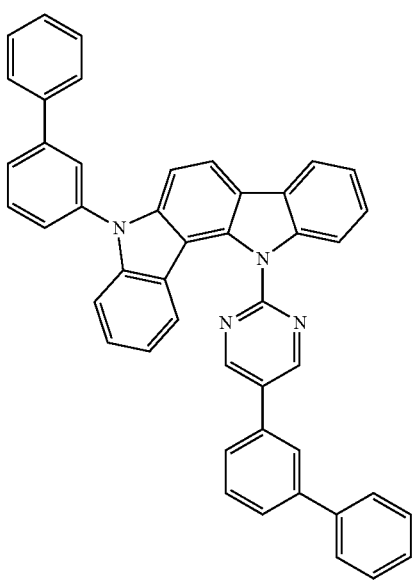

H2-52
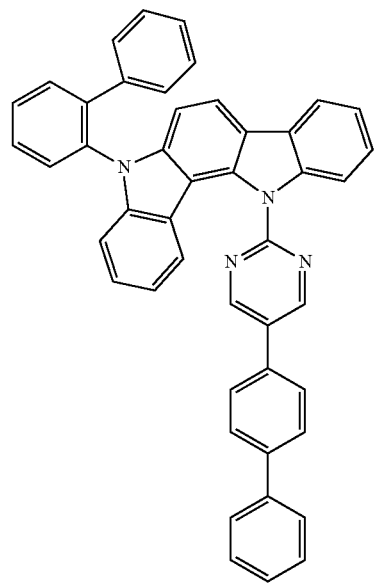
H2-53
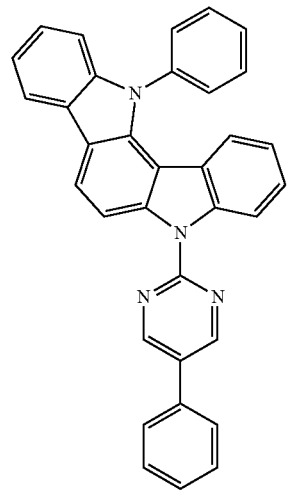
H2-54
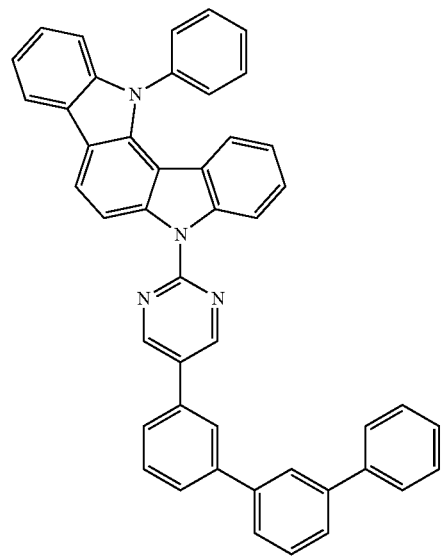
H2-55
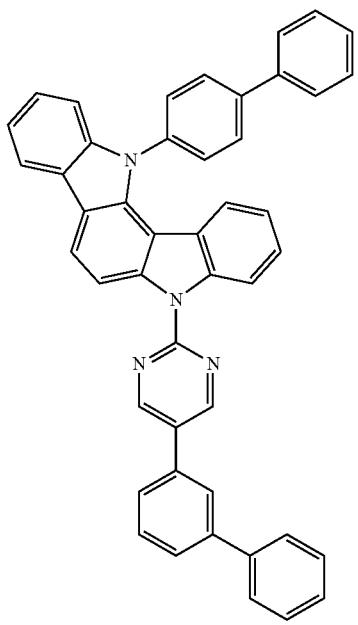
H2-56
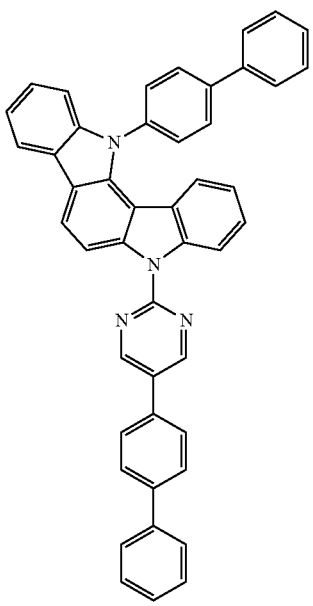

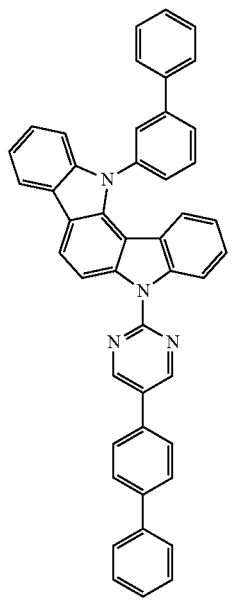
H2-57
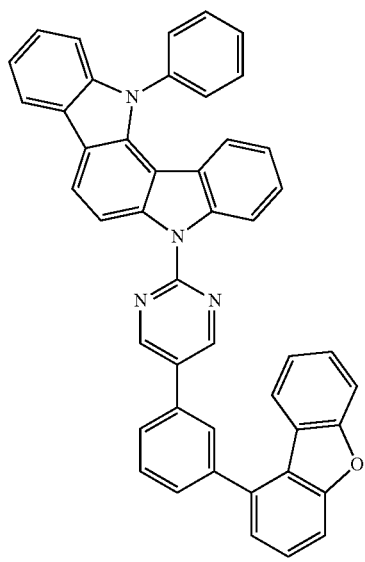
H2-59
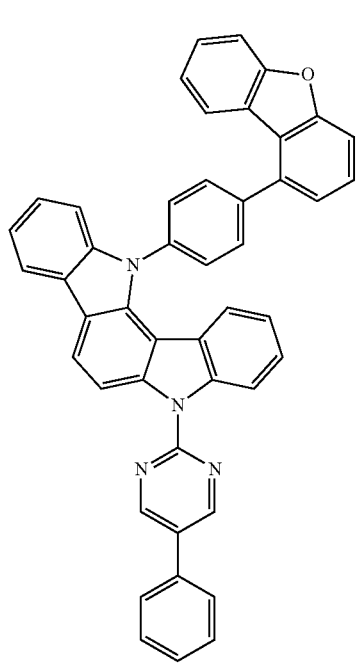
H2-58
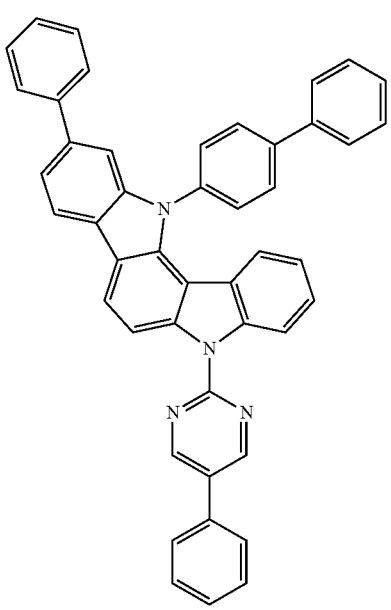
H2-60

H2-61
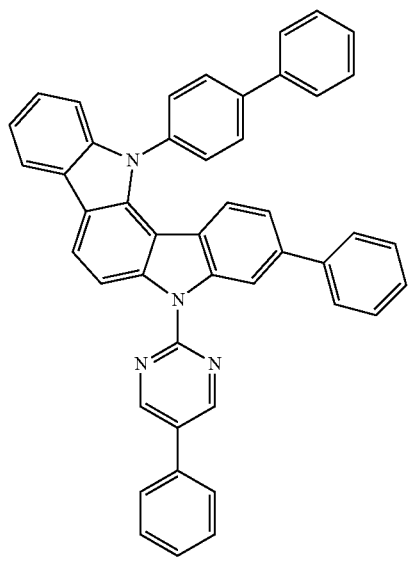
H2-62
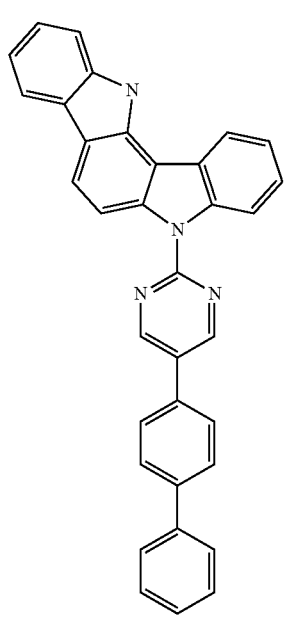
H2-63
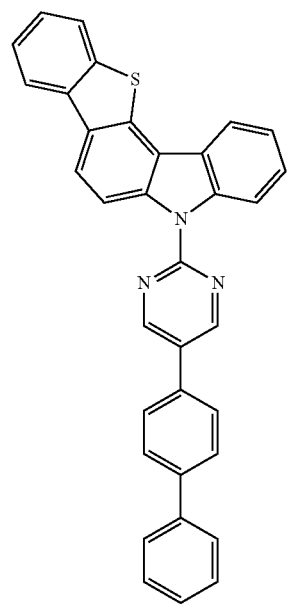
H2-64
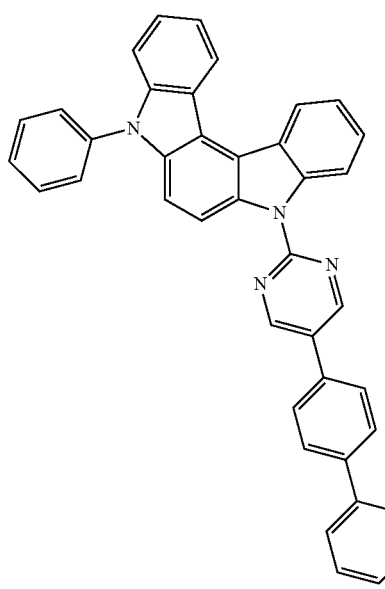
H2-65

H2-66
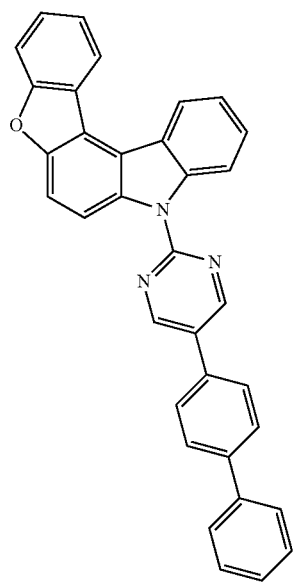
H2-67
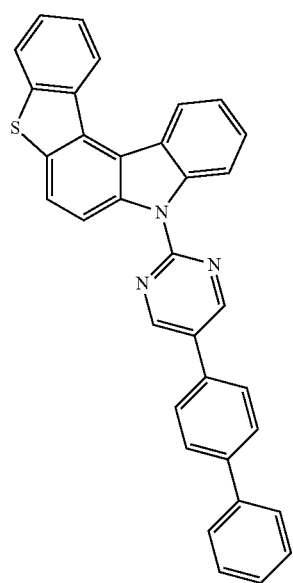
H2-68
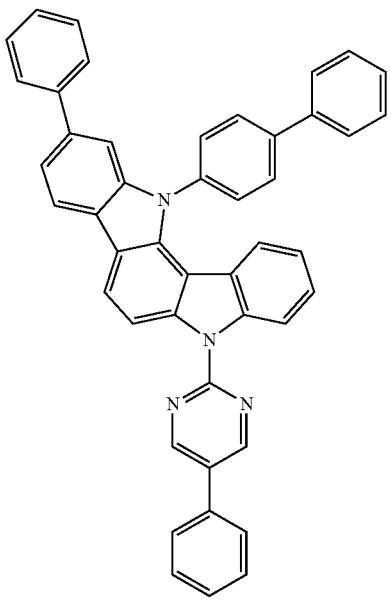
H2-69
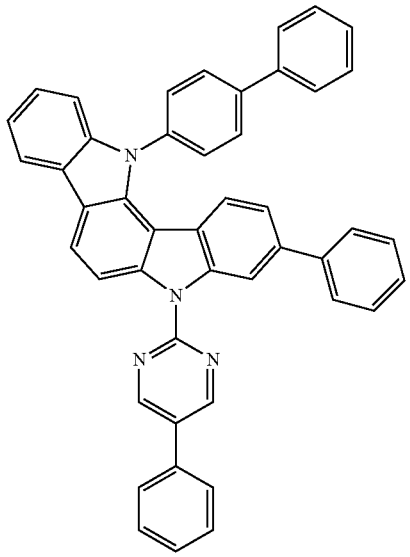

H2-70
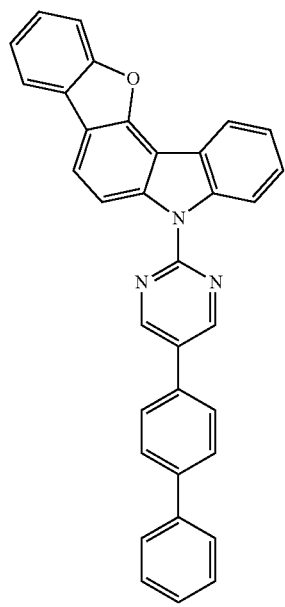
H2-71
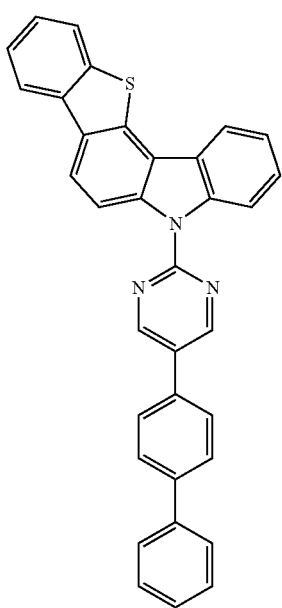
H2-72
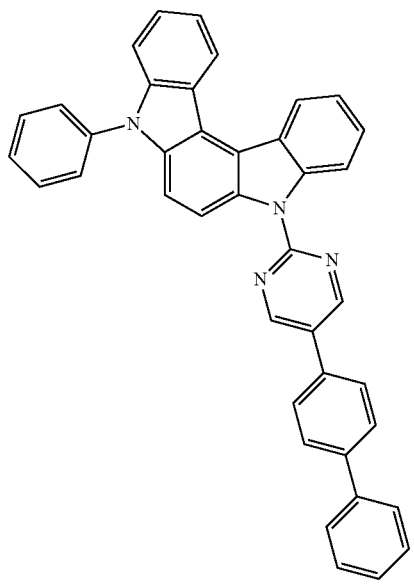
H2-73
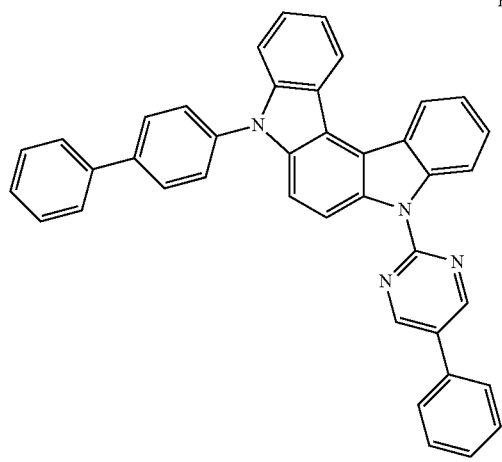
H2-74
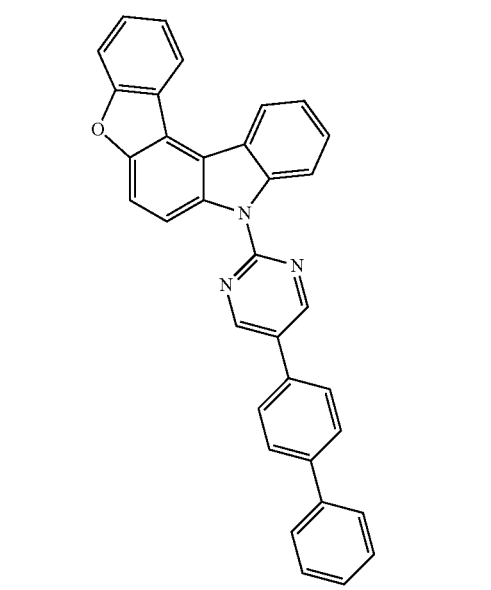

H2-75

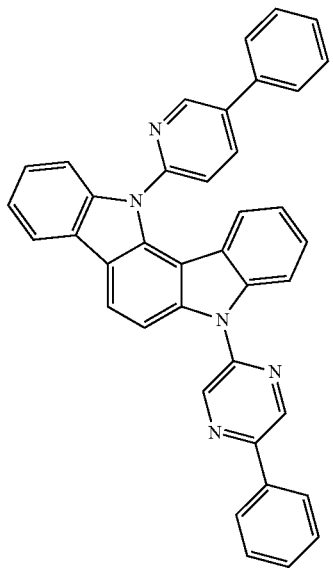

H2-76

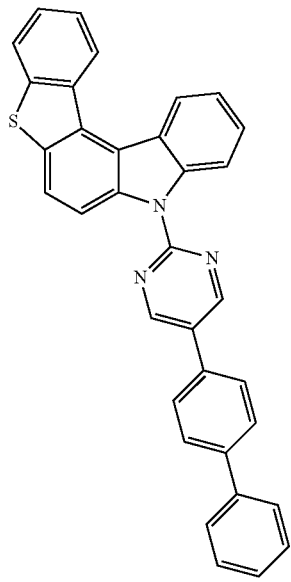

H2-77

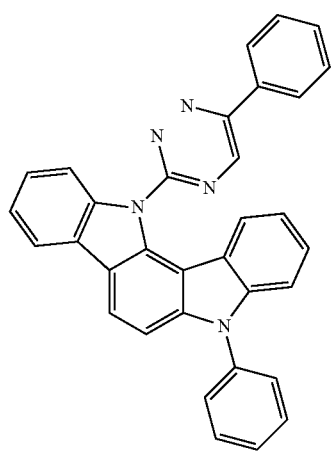

H2-78

At least one of compounds H1-1 to H1-57 and at least one of compounds H2-1 to H2-78 may be combined and used in an organic electroluminescent device.

The compound represented by formula 1 according to the present disclosure may be produced by a synthetic method known to one skilled in the art, and for example, according to the following reaction schemes 1 to 4, but is not limited thereto.

[Reaction Scheme 1]

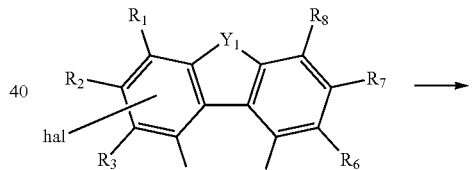

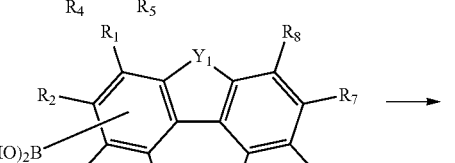

[Reaction Scheme 2]

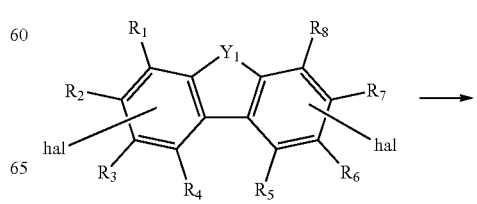

-continued

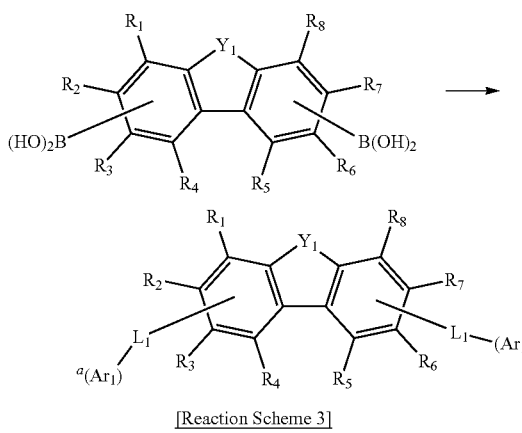

[Reaction Scheme 3]

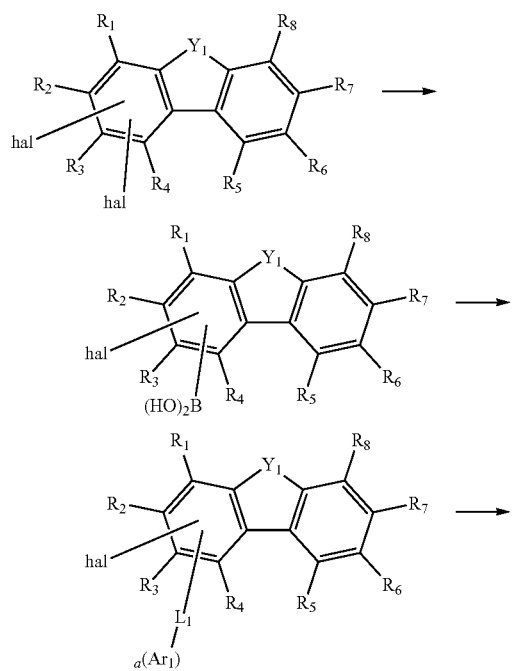

[Reaction Scheme 4]

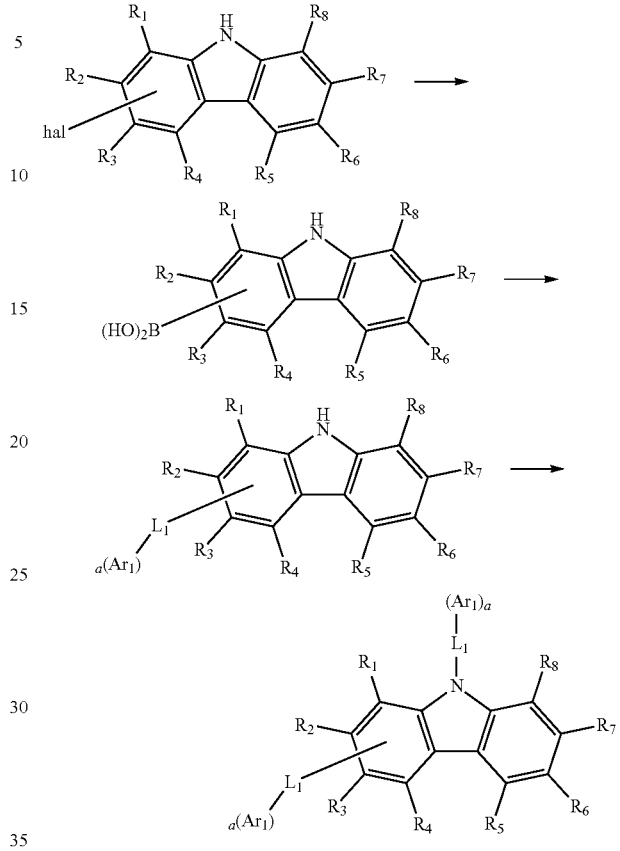

In reaction schemes 1 to 4, $Y_1$, $R_1$ to $R_8$, $L_1$, $Ar_1$, and a are as defined in formula 1, and hal represents halogen.

The compound represented by formula 2 according to the present disclosure may be produced by a synthetic method known to one skilled in the art, and for example, according to the following reaction scheme 5, but is not limited thereto.

[Reaction Scheme 5]

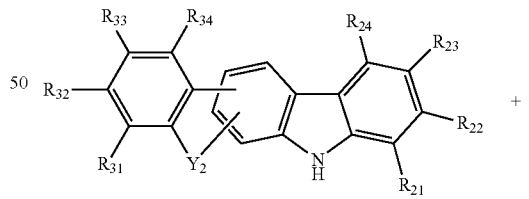

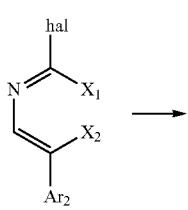

-continued

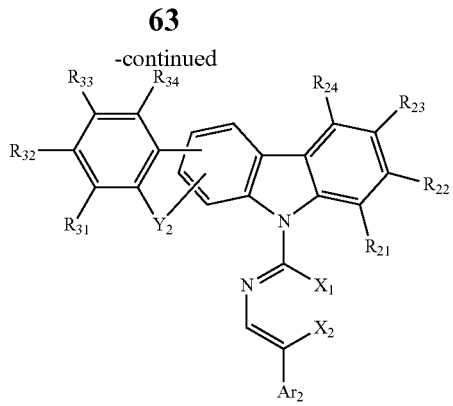

In reaction scheme 5, $Ar_2$, $X_1$, $X_2$, $R_{21}$ to $R_{24}$, $R_{31}$ to $R_{34}$, and $Y_2$ are as defined in formula 2, and hal represents halogen.

The organic electroluminescent device of the present disclosure may comprise a first electrode, a second electrode, and at least one organic layer between the first and second electrodes.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. The second electrode may be a transflective electrode or a reflective electrode, and may be a top emission type, a bottom emission type, or both-sides emission type according to the kinds of the material. In addition, the hole injection layer may be further doped with a p-dopant, and the electron injection layer may be further doped with an n-dopant.

The organic electroluminescent device according to the present disclosure may comprise an anode, a cathode, and at least one organic layer between the anode and cathode, in which the organic layer may comprise a plurality of organic electroluminescent materials including the compound represented by formula 1 as the first organic electroluminescent material, and the compound represented by formula 2 as the second organic electroluminescent material. According to one embodiment of the present disclosure, the organic electroluminescent device according to the present disclosure may comprise an anode, a cathode, and at least one light-emitting layer between the anode and cathode, in which the light-emitting layer may comprise the compound represented by formula 1 and the compound represented by formula 2.

The light-emitting layer includes a host and a dopant, in which the host includes a plurality of host materials, and the compound represented by formula 1 may be included as the first host compound of the plurality of host materials, and the compound represented by formula 2 may be included as the second host compound of the plurality of host materials. The weight ratio of the first host compound and the second host compound is about 1:99 to about 99:1, preferably about 10:90 to about 90:10, more preferably about 30:70 to about 70:30, even more preferably about 40:60 to about 60:40, and most preferable at about 50:50.

Herein, the light-emitting layer is a layer from which light is emitted, and may be a single layer or a multi-layer of which two or more layers are stacked. All of the first host material and the second host material may be included in one layer, or the first host material and the second host material may be included in respective different light-emitting layers. According to one embodiment of the present disclosure, the doping concentration of the dopant compound with respect to the host compound in the light-emitting layer may be less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device of the present disclosure may further comprise an amine-based compound besides the plurality of host materials of the present disclosure as at least one of a hole injection material, a hole transport material, a hole auxiliary material, a light-emitting material, a light-emitting auxiliary material, and an electron blocking material. Further, according to one embodiment of the present disclosure, the organic electroluminescent device of the present disclosure may further comprise an azine-based compound besides the plurality of host materials of the present disclosure as at least one of an electron transport material, an electron injection material, an electron buffer material, and a hole blocking material.

The dopant comprised in the organic electroluminescent device of the present disclosure may be at least one phosphorescent or fluorescent dopant, and is preferably at least one phosphorescent dopant. The phosphorescent dopant material applied to the organic electroluminescent device of the present disclosure is not particulary limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

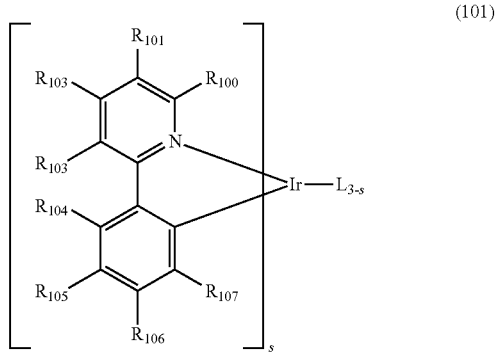

(101)

In formula 101, L is selected from the following structures 1 and 2:

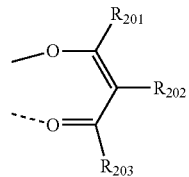

[Structure 1]

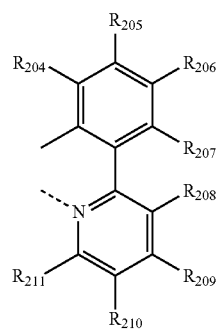

[Structure 2]

$R_{100}$ to $R_{103}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted (3- to 30-membered) heteroaryl, a cyano, or a substituted or unsubstituted (C1-C30)alkoxy; or may be linked to an adjacent substituent to form a ring(s), e.g., a substituted or unsubstituted, naphthyl, fluorene, dibenzothiophene, dibenzofuran, indenopyridine, benzofuropyridine, or benzothienopyridine ring, together with benzene;

$R_{201}$ to $R_{211}$, each independently, represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30)aryl; or may be linked to an adjacent substituent to form a ring(s); and s represents an integer of 1 to 3.

The specific examples of the dopant compound are as follows, but are not limited thereto.

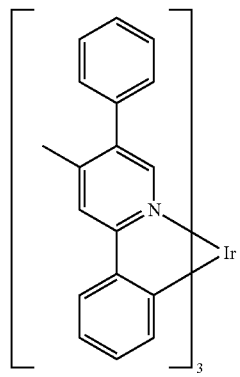

D-1

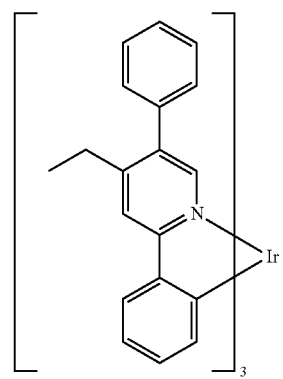

D-2

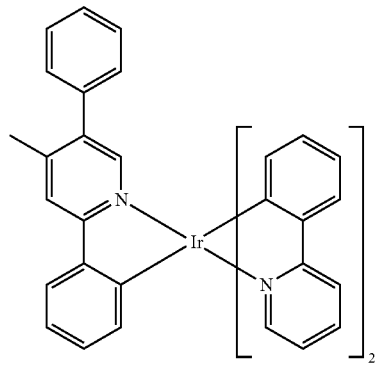

D-3

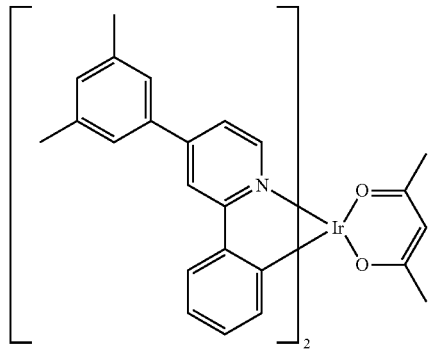

D-4

-continued
D-5
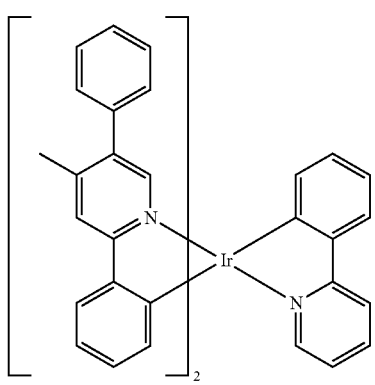
D-6
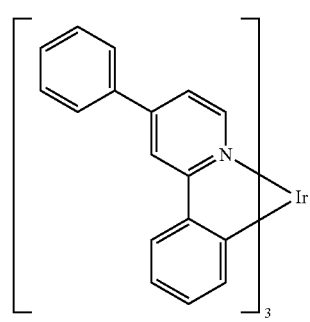
D-7
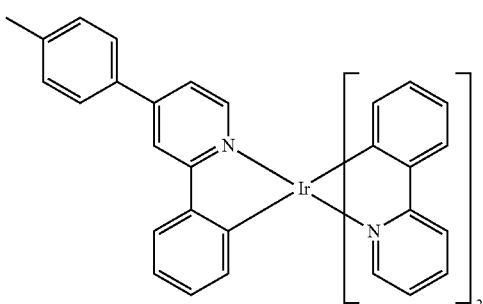
D-8
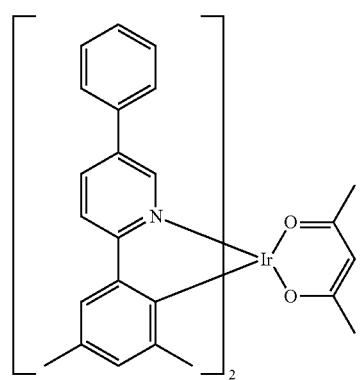
D-9
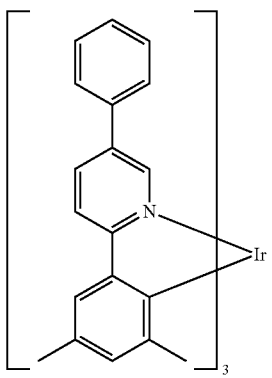
D-10
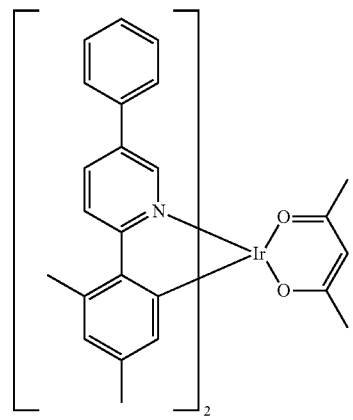
D-11
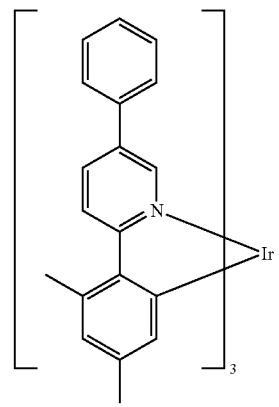
D-12
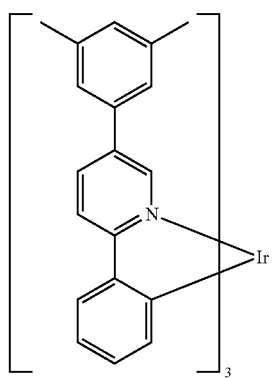

D-13
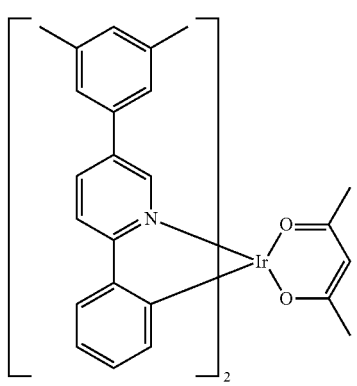
D-14
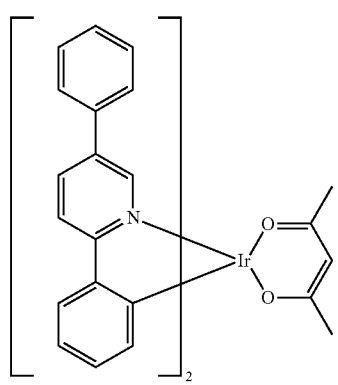
D-15
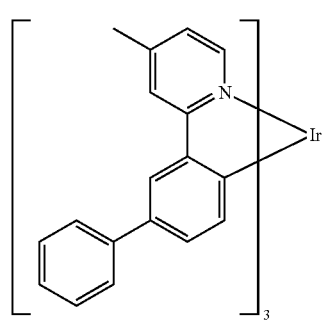
D-16
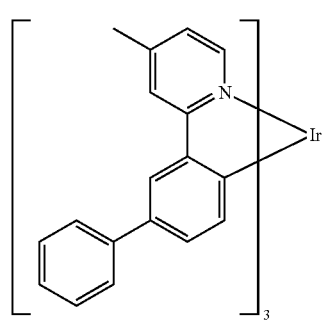
D-17
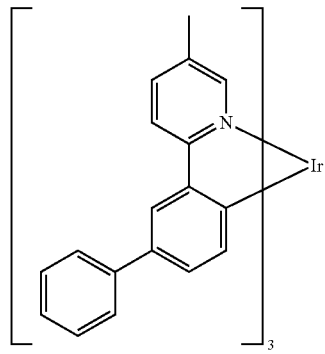
D-18
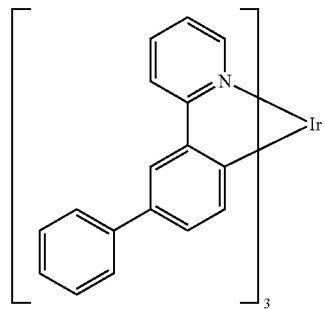
D-19
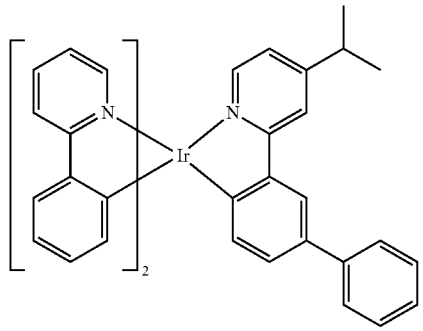
D-20
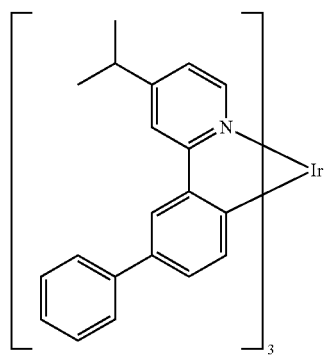

D-21 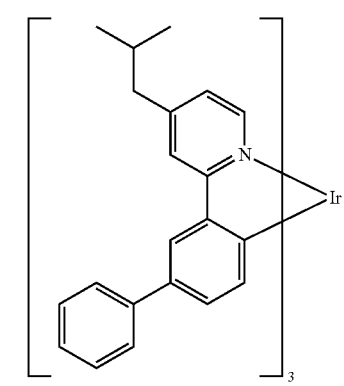
D-22 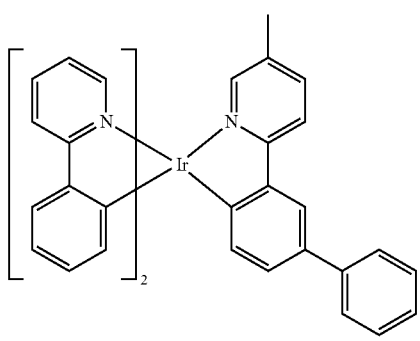
D-23 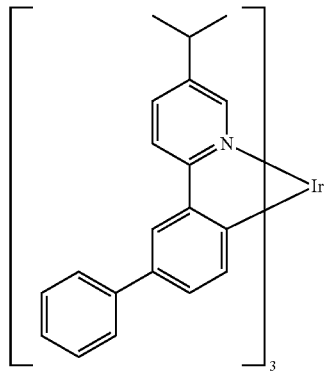
D-24 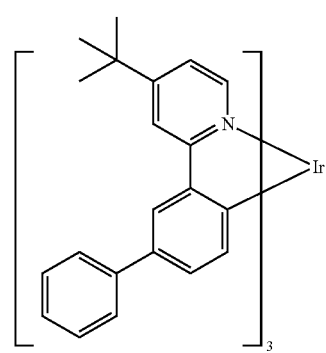
D-25 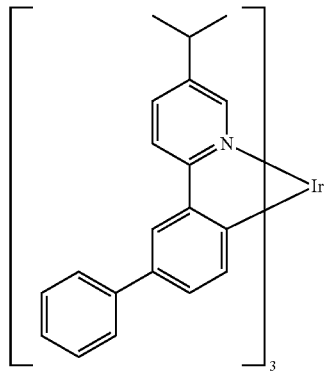
D-26 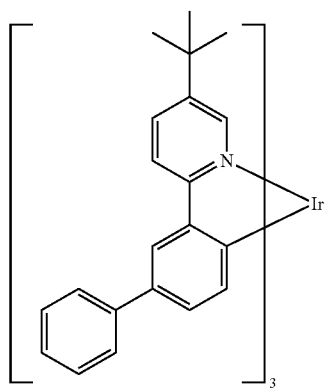
D-27 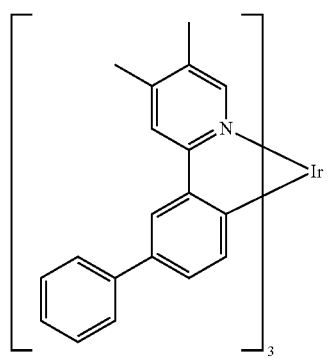
D-28 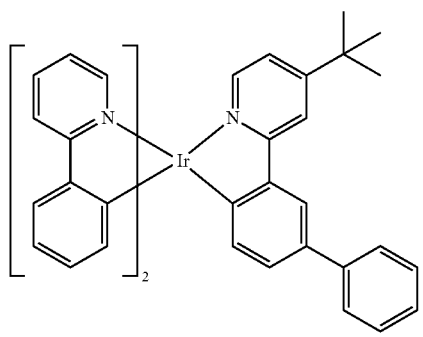

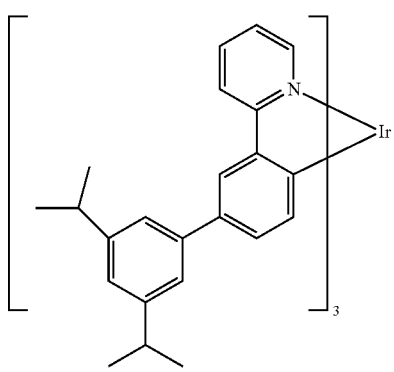
D-29
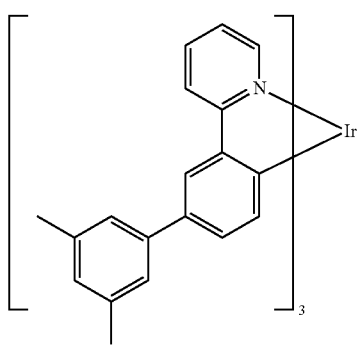
D-30
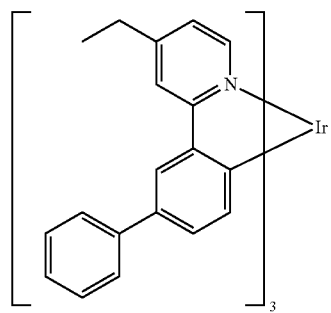
D-31
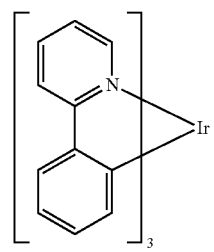
D-32
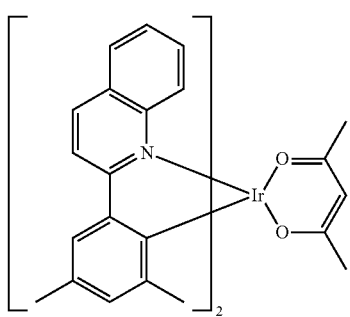
D-33
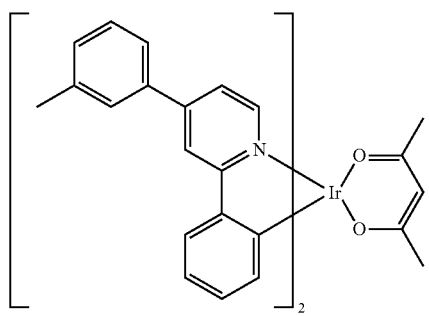
D-34
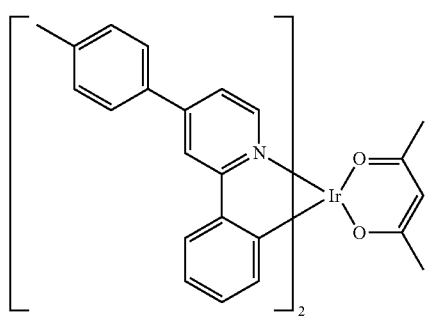
D-35
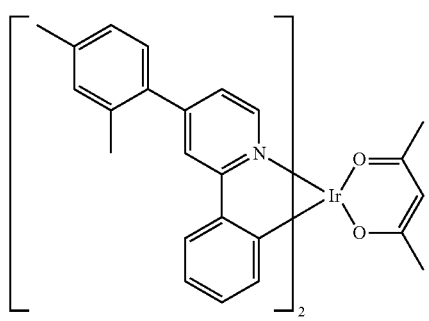
D-36
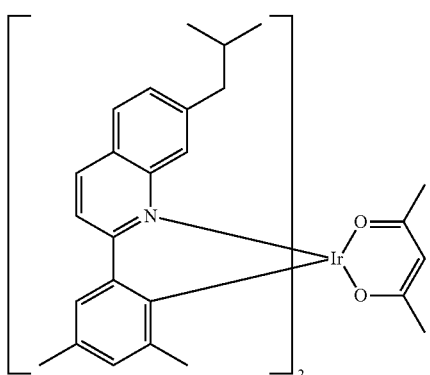
D-37
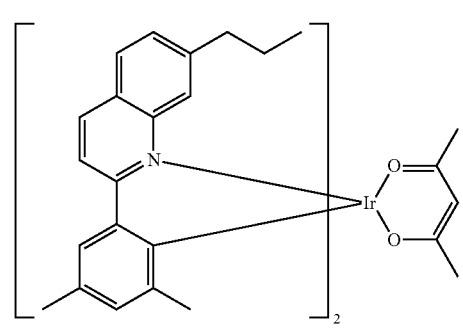
D-38

D-39
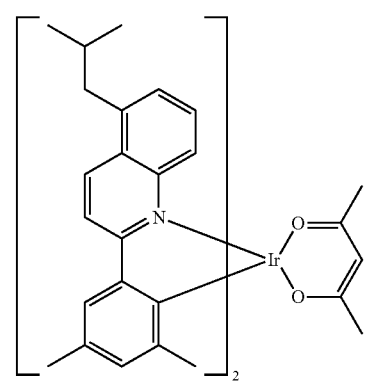
D-40
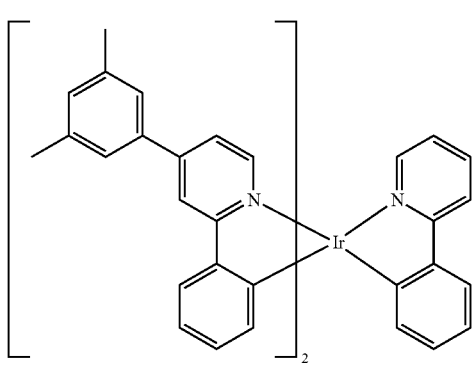
D-41
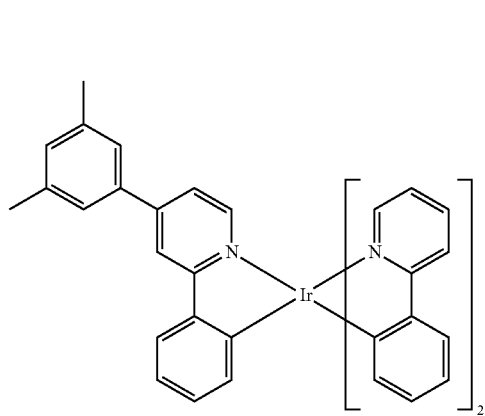
D-42
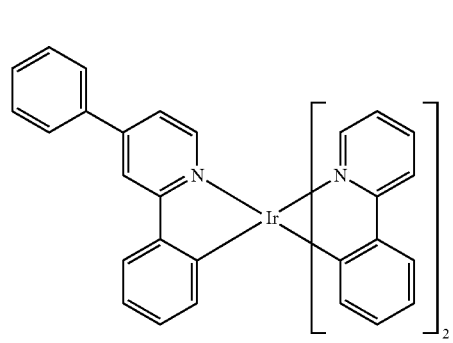
D-43
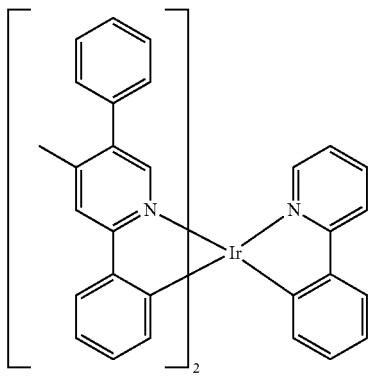
D-44
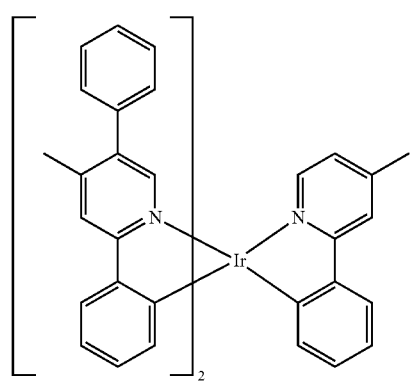
D-45
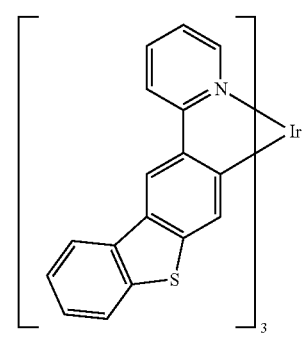
D-46
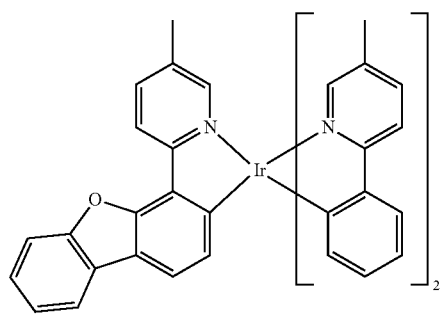

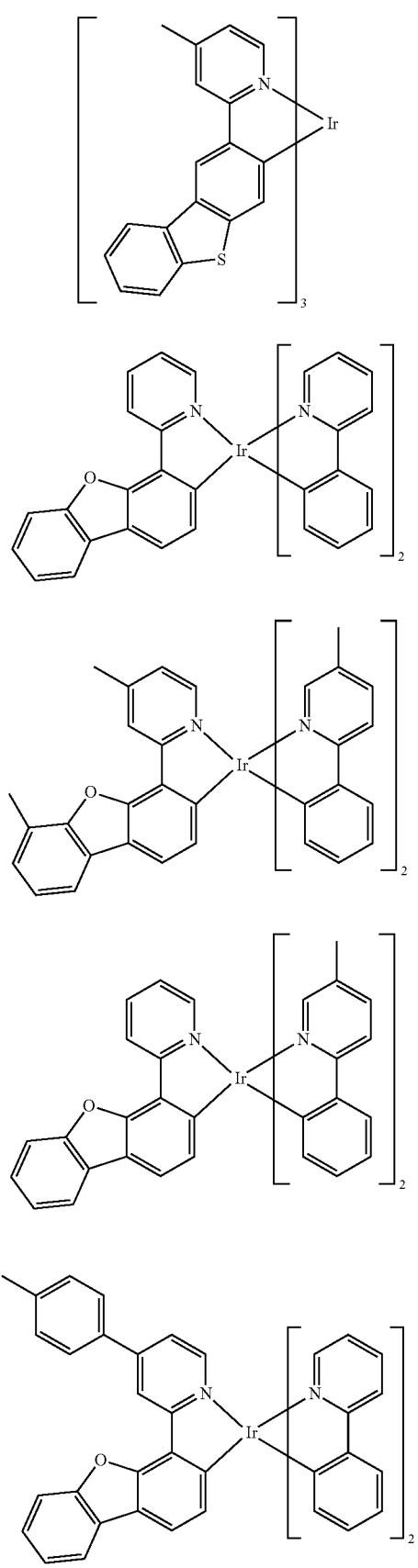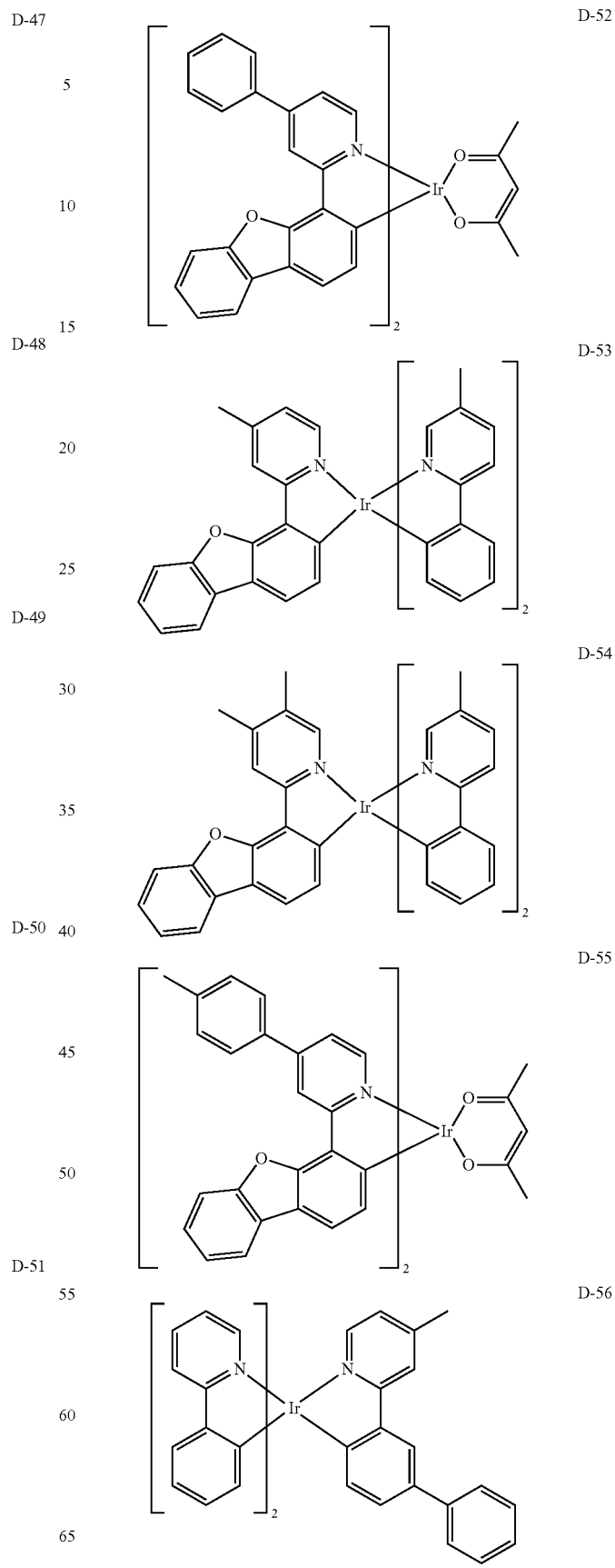

-continued
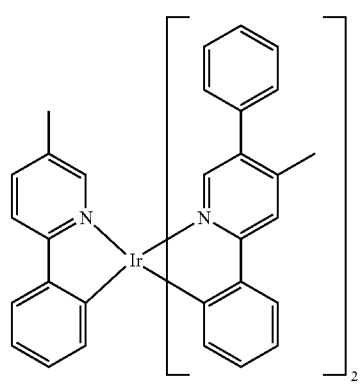
D-57
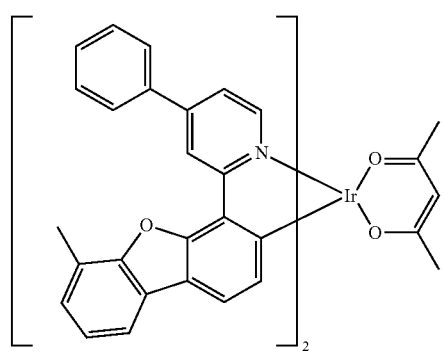
D-58
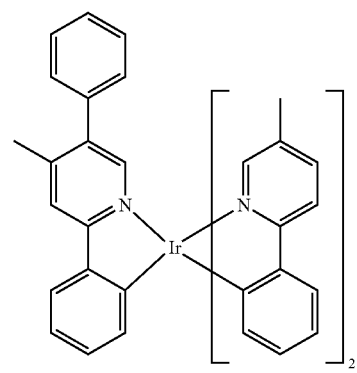
D-59
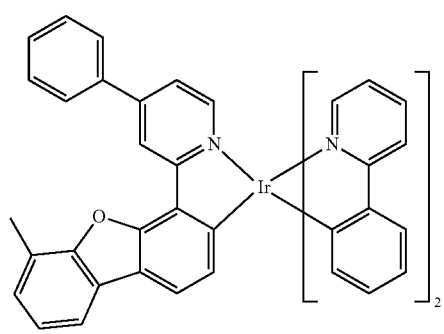
D-60
-continued
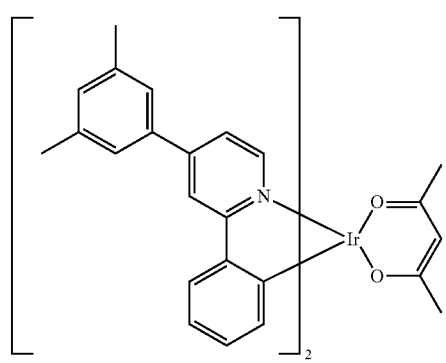
D-61
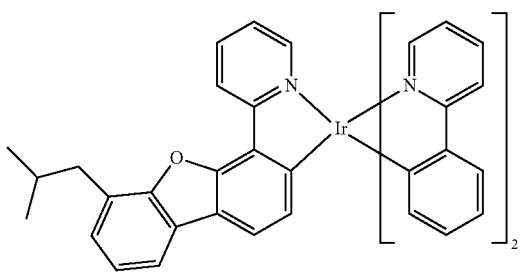
D-62
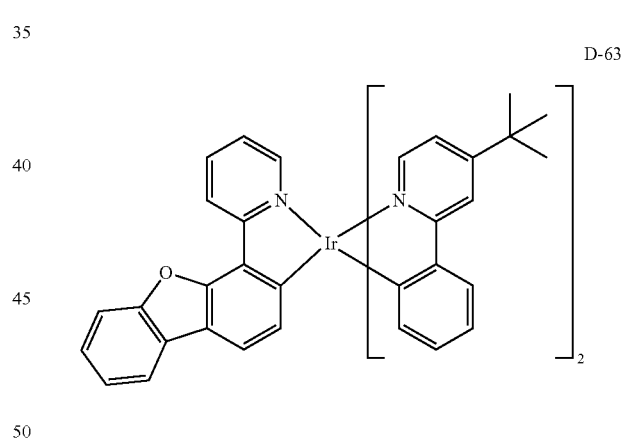
D-63
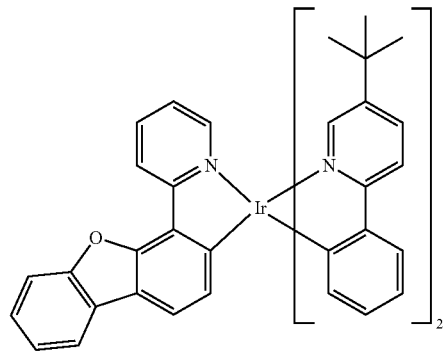
D-64

-continued
D-65
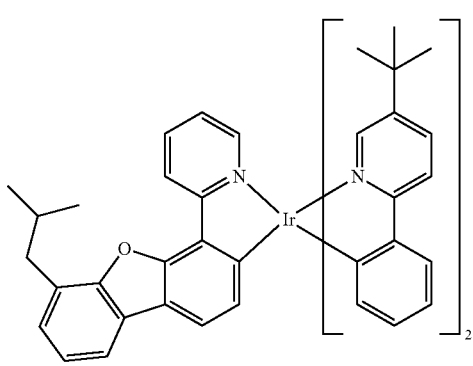
D-66
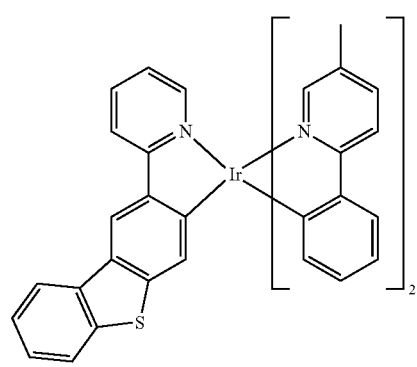
D-67
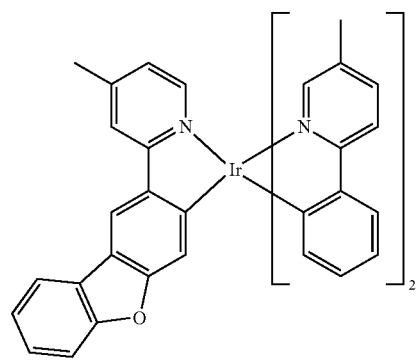
D-68
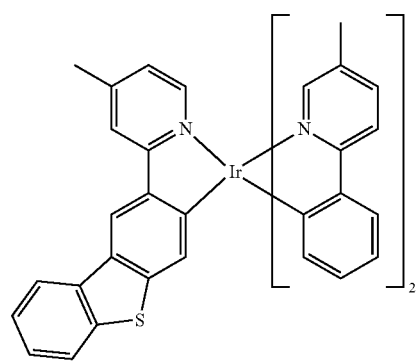
-continued
D-69
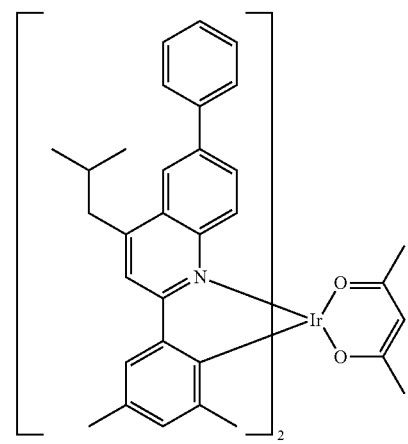
D-70
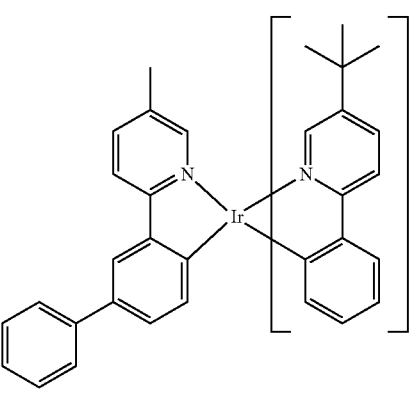
D-71
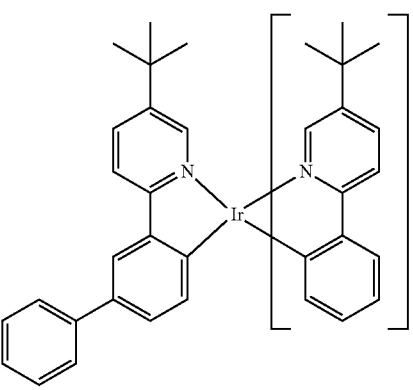
D-72
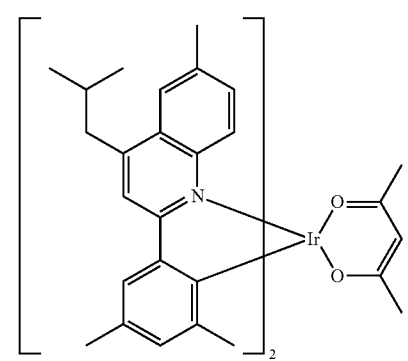

D-73
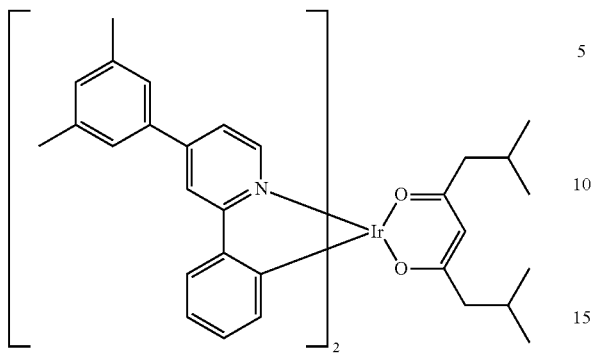
D-77
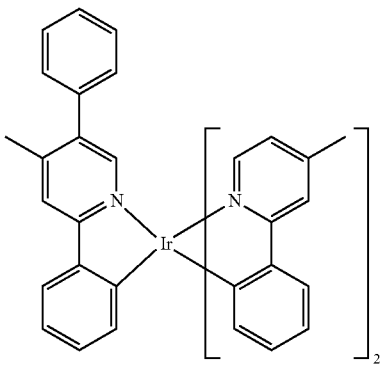
D-74
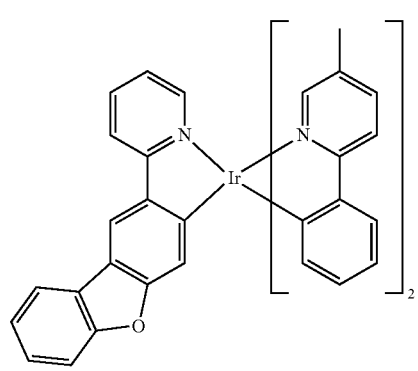
D-78
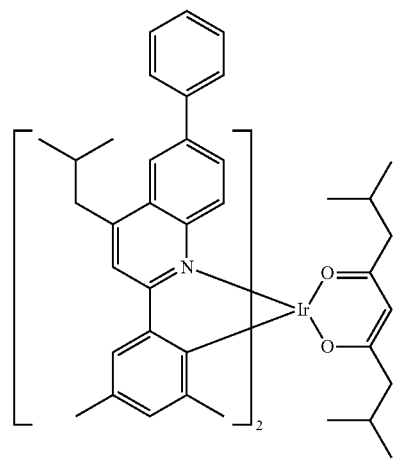
D-75
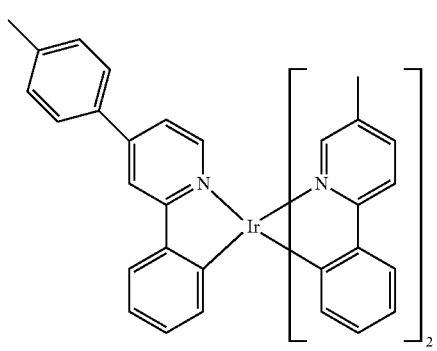
D-79
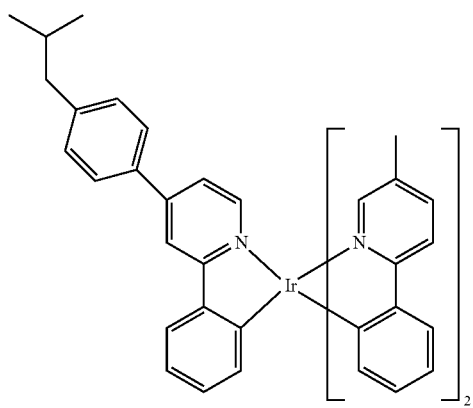
D-76
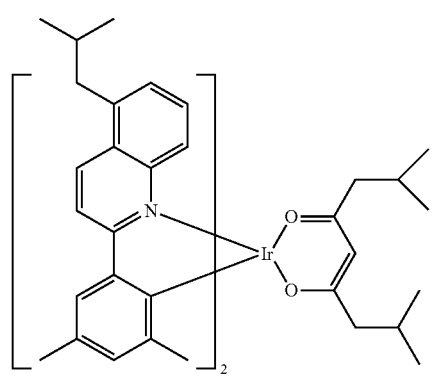
D-80
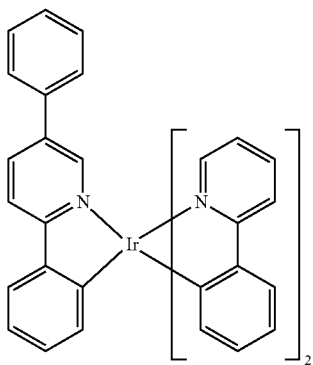

D-81
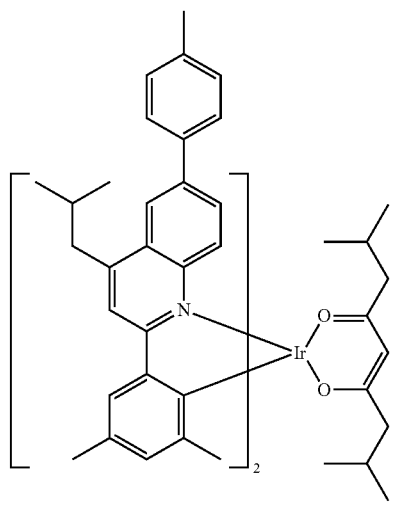
D-82
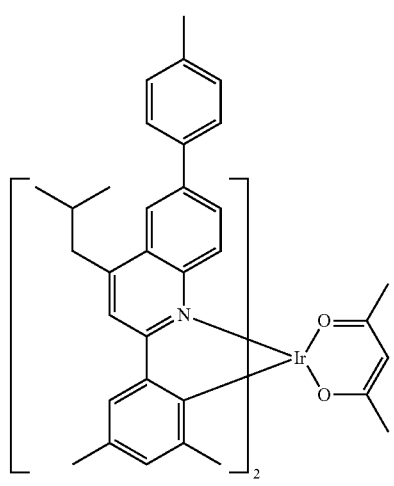
D-83
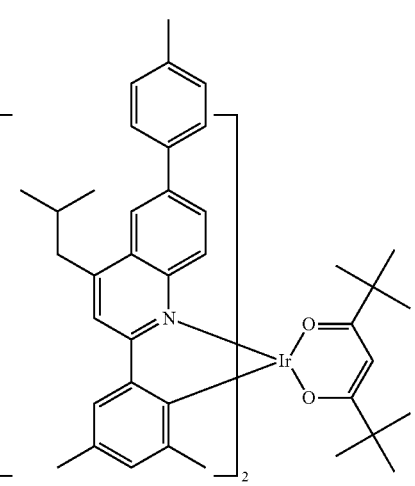
D-84
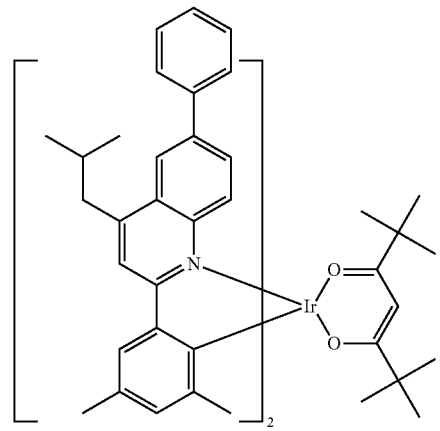
D-85
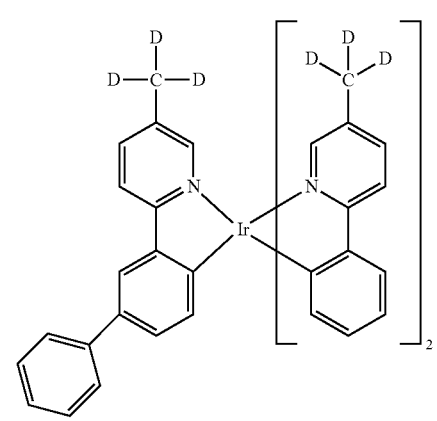
D-86
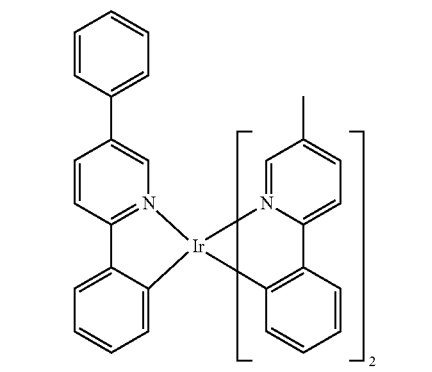
D-87
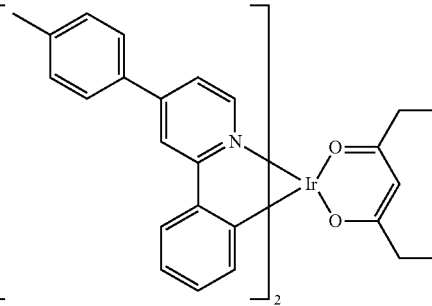

D-88
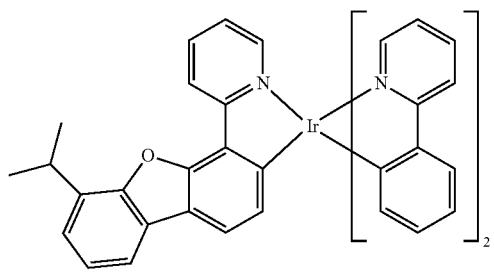
D-89
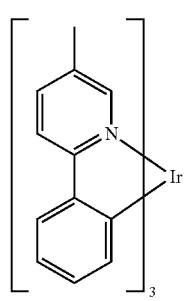
D-90
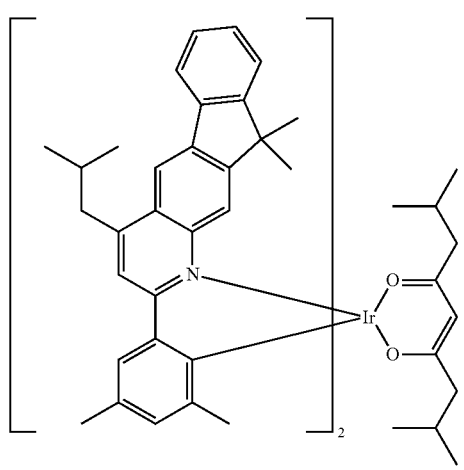
D-91
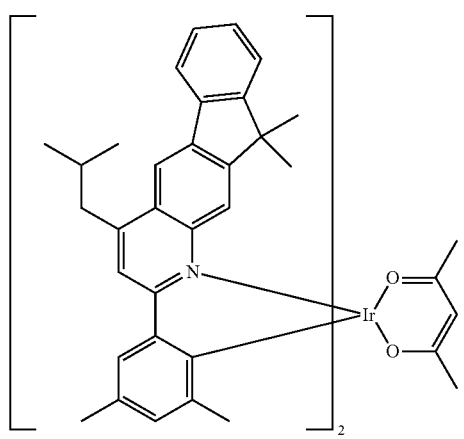
D-92
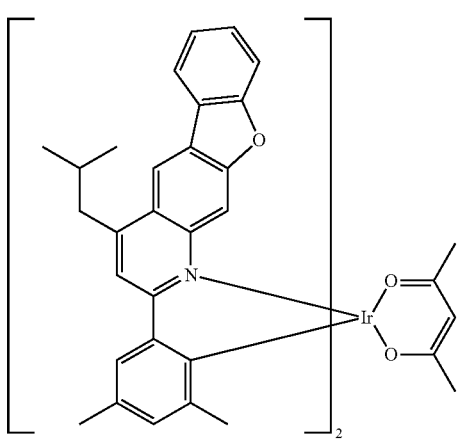
D-93
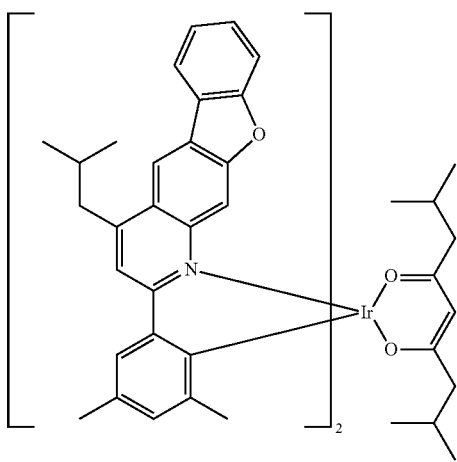
D-94

D-95
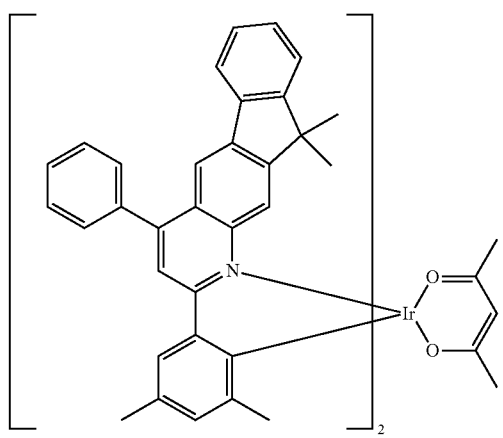
D-96
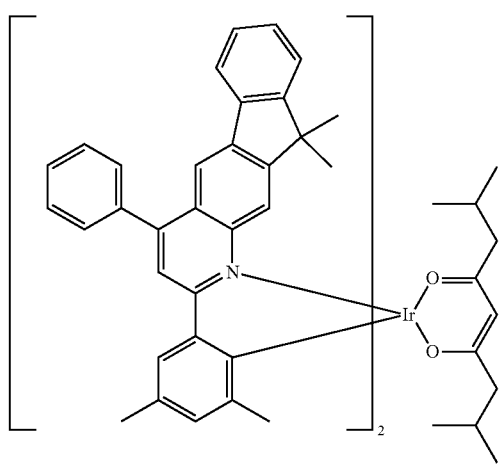
D-97
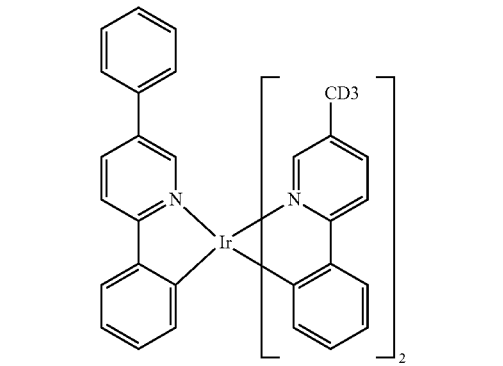
D-98
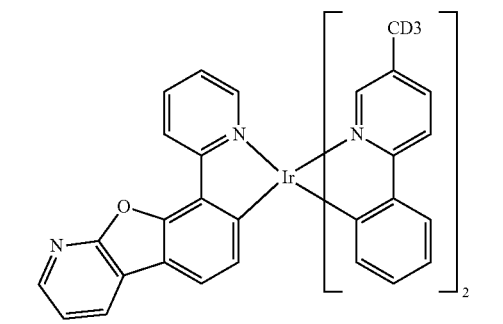
D-99
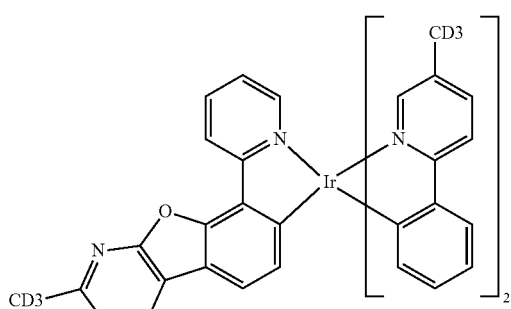
D-100
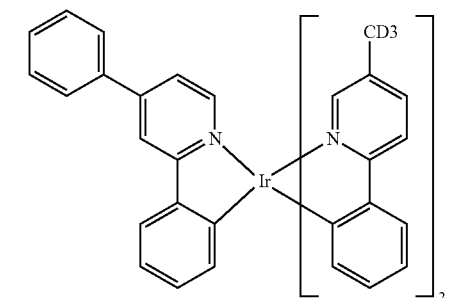
D-101
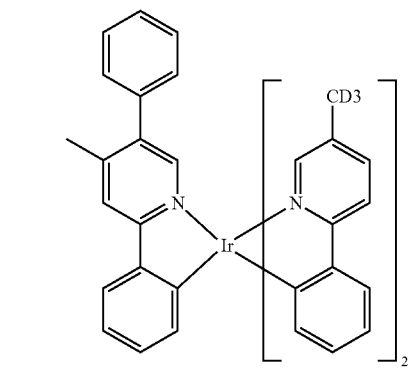
D-102
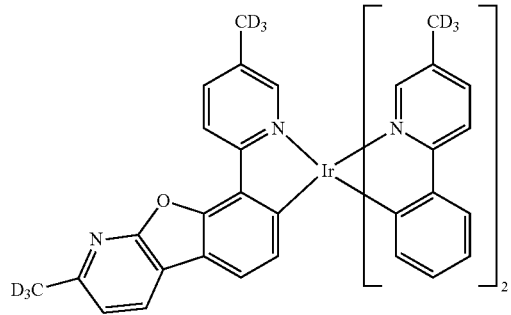

-continued
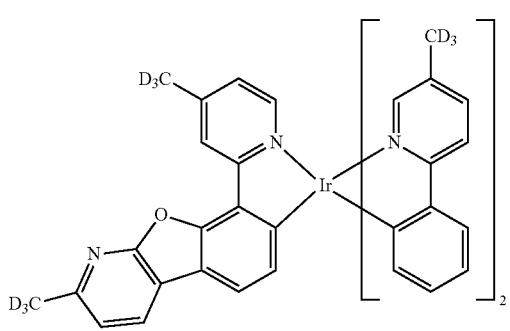
D-103
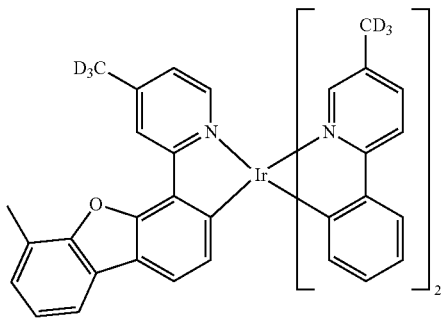
D-107
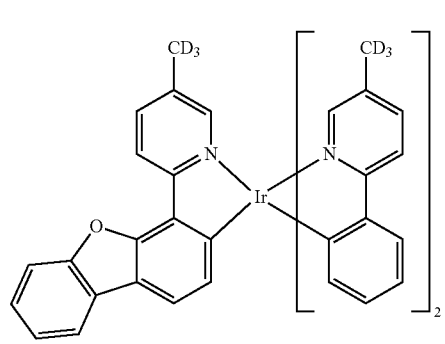
D-104
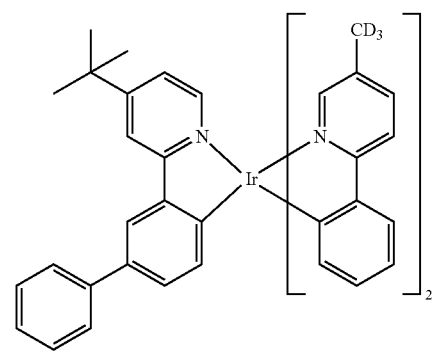
D-108
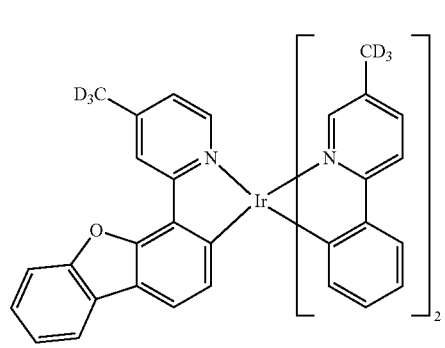
D-105
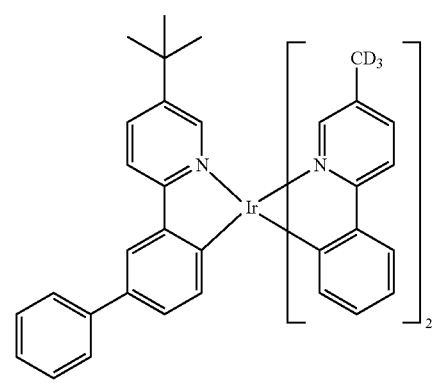
D-109
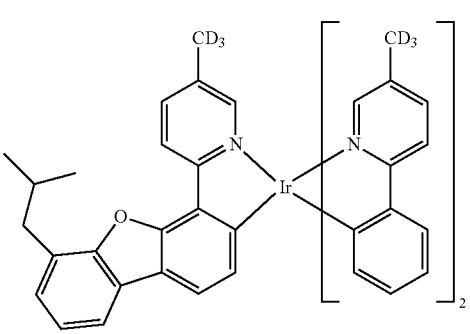
D-106
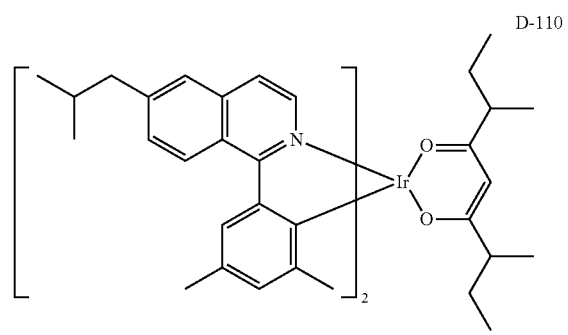
D-110

D-111 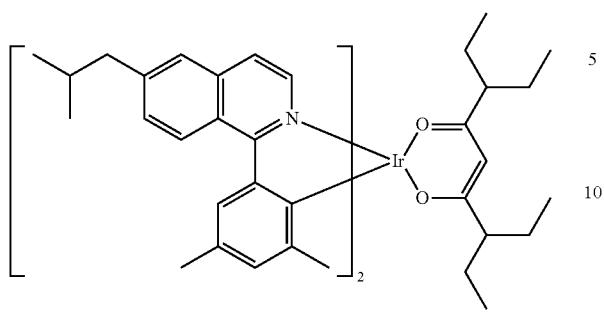

D-112

D-113

D-114

D-115 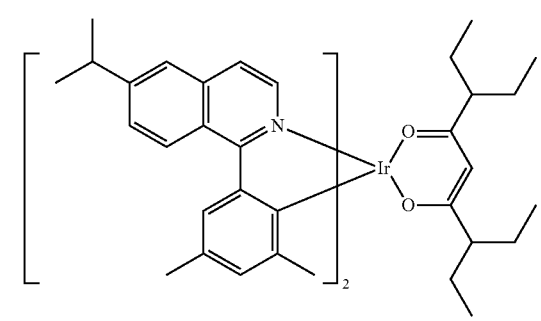

D-116 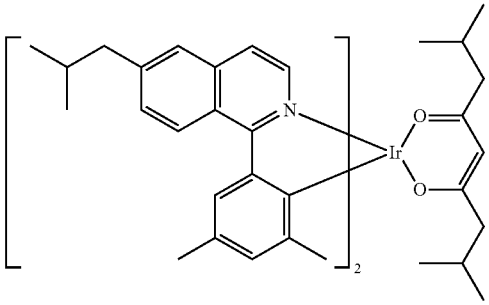

D-117

D-118 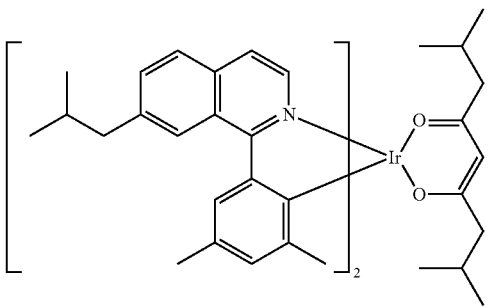

D-119 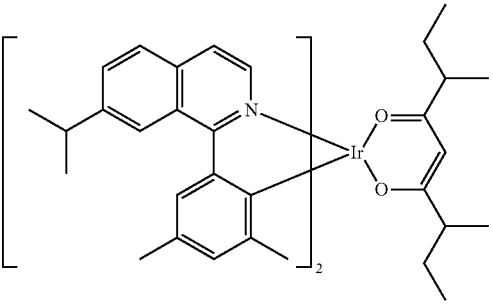

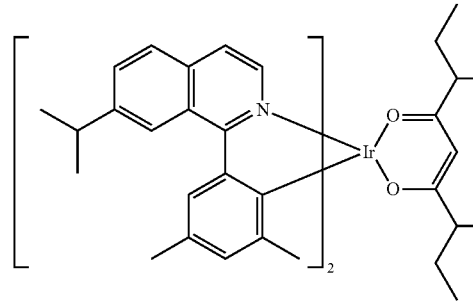

In the organic electroluminescent device of the present disclosure, a hole injection layer, a hole transport layer, an electron blocking layer, or a combination thereof can be used between the anode and the light-emitting layer. The hole injection layer may be multilayered in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayered in order to control the injection of the electron and improve the interfacial properties between the light-emitting layer and the electron injection layer, wherein each of the multilayers may use two compounds simultaneously. The hole blocking layer or the electron transport layer may also be multilayered, wherein each of the layers may use a plurality of compounds.

In addition, the organic electroluminescent compound or the plurality of host materials according to the present disclosure may also be used in an organic electroluminescent device comprising a QD (quantum dot).

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

The first and the second host compounds of the present disclosure may be film-formed by the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to the cell to evaporate the materials. Further, if the first and the second host compounds are present in the same layer or different layers in an organic electroluminescent device, the two host compounds may individually form films. For example, the second host compound may be deposited after depositing the first host compound.

The present disclosure may provide a display device by using the plurality of host materials including the compound represented by formula 1 and the compound represented by formula 2. That is, by using the plurality of host materials of the present disclosure, it is possible to manufacture a display system or a lighting system. Specifically, by using the plurality of host materials of the present disclosure, a display system, for example, for white organic light emitting devices, smart phones, tablets, notebooks, PCs, TVs, or cars; or a lighting system, for example an outdoor or indoor lighting system, can be produced.

Hereinafter, the preparation method for the compound of the present disclosure and the properties thereof, and the properties of an organic electroluminescent device comprising the plurality of host materials of the present disclosure, will be explained in detail with reference to the representative compounds of the present disclosure. However, the present disclosure is not limited by the following examples.

Example 1: Preparation of Compound H2-1

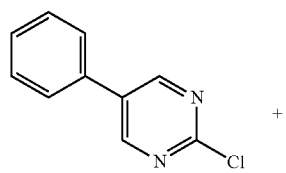

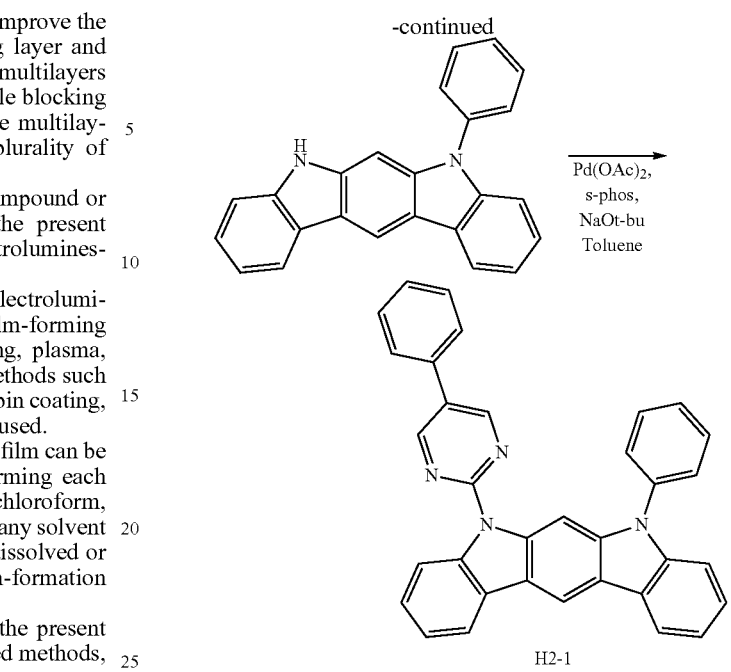

In a flask, 2-chloro-5-phenylpyrimidine (2.7 g, 14.2 mmol) and 5-phenyl-5,7-dihydroindolo[2,3-b]carbazole (3.5 g, 10.9 mmol) were introduced into palladium(II) acetate (Pd(OAc)$_2$) (0.11 g, 0.5 mmol), a ligand (2-dicyclohexylphosphino-2', 6'-dimethoxybiphenyl) (0.45 g, 1.1 mmol), NaOt-bu (2.8 g, 27.3 mmol), and toluene (200 mL), and the mixture was refluxed at 140° C. for 4 hours. After completion of the reaction, distilled water was added to the reaction mixture, and an organic layer was extracted with dichloromethane. The remaining moisture of the organic layer was removed using magnesium sulfate, and the residue was dried. The residue was separated by column chromatography to obtain 3.2 g of compound H2-1 (yield: 60.3%) (m.p.: 231° C.).

Device Example 1: Producing an OLED Comprising the Plurality of Host Materials According to the Present Disclosure An OLED according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into a cell of the vacuum vapor deposition apparatus and was evaporated by applying an electric current to the cell, thereby forming a first hole transport layer having a thickness of 10 nm on the second hole injection layer. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layers and the hole transport layers, a light-emitting layer was formed thereon as follows: Compound H1-1 and compound H2-1 were introduced into two cells of the vacuum vapor depositing apparatus as hosts, and compound D-50 was introduced into another cell as a dopant. The two host materials were evaporated at a rate of 2:1 and the dopant material was simultaneously evaporated at a different rate, and the dopant was deposited in a doping amount of 10 wt % based on the total amount of the host and the dopant to form a light-emitting layer having a thickness of 40 nm on the second hole transport layer. Compound ET-1 and compound EI-1 were introduced into two cells and evaporated at a rate of 4:6 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at 104 torr.

HI-1

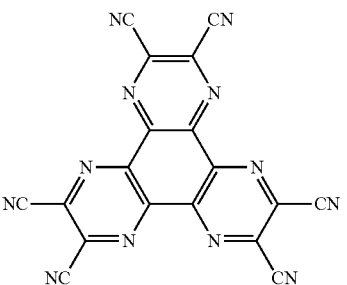

HI-2

HT-1

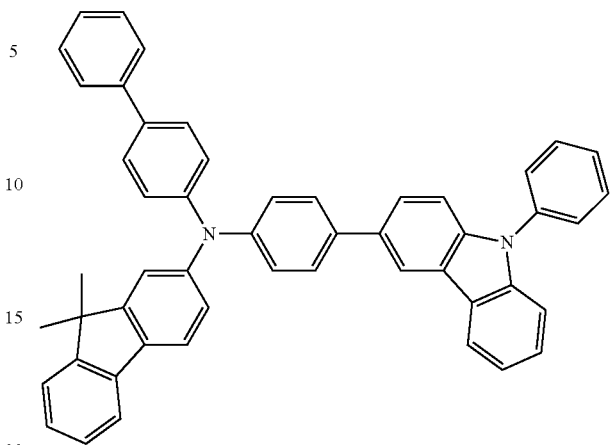

HT-2

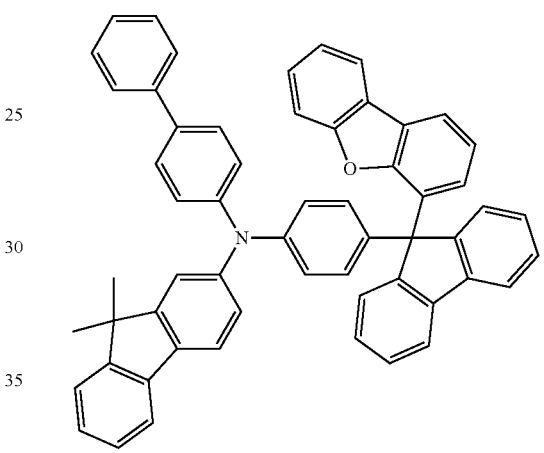

ET-1

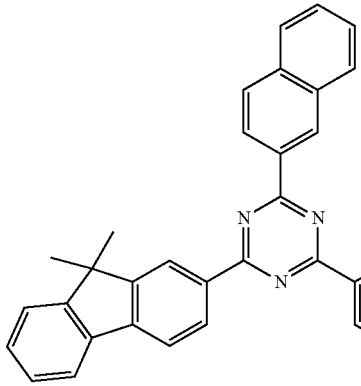

EI-1

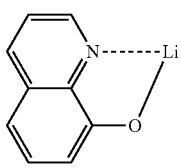

Device Example 2: Producing an OLED
Comprising the Plurality of Host Materials
According to the Present Disclosure An OLED was produced in the same manner as in Device Example 1, except that compound H1-33 and compound H2-1 were used as the first and second hosts, respectively.

Device Example 3: Producing an OLED
Comprising the Plurality of Host Materials
According to the Present Disclosure An OLED was produced in the same manner as in Device Example 1. except that compound H1-3 and compound H2-1 were used as the first and second hosts, respectively.

Device Example 4: Producing an OLED
Comprising the Plurality of Host Materials
According to the Present Disclosure An OLED was produced in the same manner as in Device Example 1, except that compound H1-31 and compound H2-1 were used as the first and second hosts, respectively.

Device Example 5: Producing an OLED
Comprising the Plurality of Host Materials
According to the Present Disclosure An OLED was produced in the same manner as in Device Example 1, except that compound H1-46 and compound H2-1 were used as the first and second hosts, respectively.

Device Example 6: Producing an OLED
Comprising the Plurality of Host Materials
According to the Present Disclosure An OLED was produced in the same manner as in Device Example 1, except that compound H1-47 and compound H2-1 were used as the first and second hosts, respectively.

Comparative Example 1: Producing an OLED not
According to the Present Disclosure An OLED was produced in the same manner as in Device Example 1, except that compound H1 and compound H2 were used as the first and second hosts, respectively.

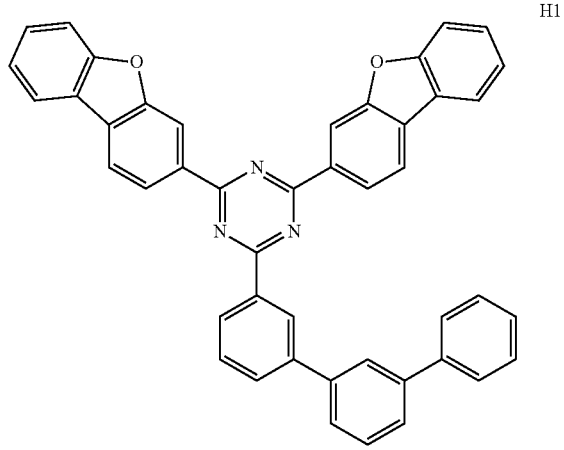

H1

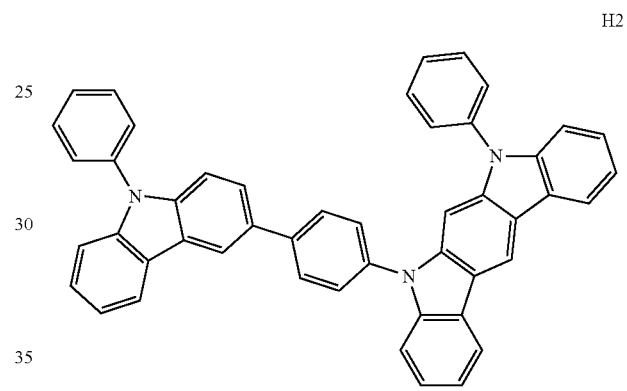

H2

The driving voltage, luminous efficiency, and CIE color coordinates at a luminance of 1,000 nit, and the time taken for luminance to decrease from 100% to 95% at a constant current in a luminance of 20,000 nit (lifespan; T95) of the OLEDs produced in Device Examples 1 to 6 and Comparative Example 1 are provided in Table 1 below.

TABLE 1

|  | Host | Voltage [V] | Luminous Efficiency [cd/A] | CIE color coordinates (x, y) | T95 Lifespan [hr] |
| --- | --- | --- | --- | --- | --- |
| Device Example 1 | H1-1:H2-1 | 2.9 | 88.1 | 0.352, 0.615 | 87.1 |
| Device Example 2 | H1-33:H2-1 | 2.9 | 87.5 | 0.352, 0.615 | 49.2 |
| Device Example 3 | H1-3:H2-1 | 2.8 | 86.7 | 0.355, 0.613 | 103.6 |
| Device Example 4 | H1-31:H2-1 | 2.9 | 84.9 | 0.352, 0.615 | 87.1 |
| Device Example 5 | H1-46:H2-1 | 3.0 | 81.8 | 0.342, 0.622 | 77.5 |
| Device Example 6 | H1-47:H2-1 | 3.0 | 79.7 | 0.343, 0.621 | 58.3 |
| Comparative Example 1 | H1:H2 | 2.7 | 77.8 | 0.351, 0.616 | 40.0 |

From Table 1 above, it can be seen that the OLEDs comprising the plurality of host materials comprising a specific combination of compounds according to the present disclosure have remarkably improved luminous efficiency and lifespan property, compared to the conventional OLEDs. Further, due to low voltage and high luminous efficiency, the power efficiency can also be improved.

Without intending to be limited by theory, the second host according to formula 2 of the present disclosure has a very high hole mobility due to high HOMO value and low electron mobility due to moieties of indolocarbazole, etc., and pyrimidine, etc. Due to such unbalance of the holes and electrons, the luminous efficiency and lifespan property may be insufficient.

Meanwhile, when the host of formula 1 is combined with the host of formula 2, since the electron mobility of the host of formula 1 is high, it seems that the unbalanced transport of holes and electrons of the host of formula 2 may be improved. As a result, due to the increase of the formation of excitons in the light-emitting layer, the luminous efficiency and lifespan property may be improved.

The invention claimed is:

1. A plurality of host materials comprising a first host material comprising a compound represented by the following formula 1, and a second host material comprising a compound represented by the following formula 2:

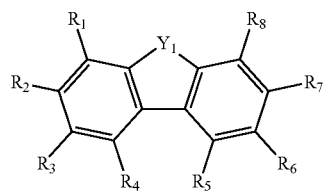
(1)

wherein $Y_1$ represents O, S, $CR_{11}R_{12}$, or $NR_{13}$;

$R_{11}$ and $R_{12}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or $R_{11}$ and $R_{12}$ may be linked to each other to form a spiro ring;

$R_1$ to $R_8$, and $R_{13}$ each independently represent -$L_1$-$(Ar_1)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl, with a proviso that one or more of $R_1$ to $R_8$, and $R_{13}$ is -$L_1$-$(Ar_1)_a$;

$L_1$ represents a single bond, a substituted or unsubstituted (C6-C30)arylene, or a substituted or unsubstituted (3- to 30-membered)heteroarylene;

$Ar_1$ each independently represents a substituted or unsubstituted nitrogen-containing (3- to 30-membered)heteroaryl, where if a plurality of $Ar_1$'s are present, each of $Ar_1$ may be the same or different;

a represents an integer of 1 to 4, where if a plurality of a's are present, each of a may be the same or different, and where if a is an integer of 2 or more, each of $Ar_1$ may be the same or different;

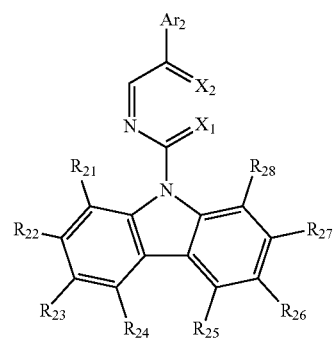
(2)

wherein $Ar_2$ represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, or a substituted or unsubstituted (3-to 30-membered)heteroaryl;

$X_1$ and $X_2$ each independently represent N or CH, with a proviso that one or more of $X_1$ and $X_2$ is N;

at least one of $R_{21}$ and $R_{22}$, $R_{22}$ and $R_{23}$, $R_{23}$ and $R_{24}$, $R_{25}$ and $R_{26}$, $R_{26}$ and $R_{27}$, and $R_{27}$ and $R_{28}$ are fused in each two * positions of the following formula to form a ring of the following formula;

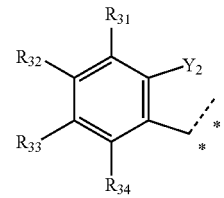

the remainders of $R_{21}$ to $R_{28}$ which do not form a ring and $R_{31}$ to $R_{34}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, or a substituted or unsubstituted (3- to 30-membered)heteroaryl, where if a plurality of $R_{31}$'s to $R_{34}$'s are present, each of $R_{31}$, each of $R_{32}$, each of $R_{33}$, and each of $R_{34}$ may be the same or different;

$Y_2$ represents O, S, $CR_{14}R_{15}$, or $NR_{16}$, where if a plurality of $Y_2$'s are present, each of $Y_2$ may be the same or different;

$R_{14}$ and $R_{15}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or $R_{14}$ and $R_{15}$ may be linked to each other to form a spiro ring; and $R_{16}$ represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, or a substituted or unsubstituted (3- to 30-membered)heteroaryl.

2. The plurality of host materials according to claim 1, wherein formula 1 is represented by at least one of the following formulas 1-1 to 1-5:

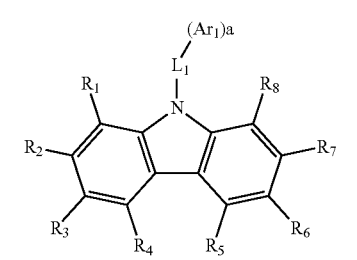
(1-1)

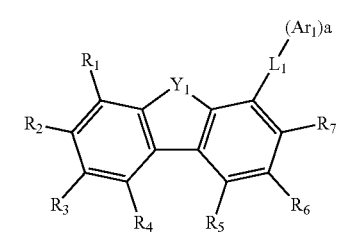
(1-2)

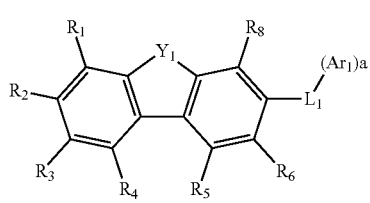
(1-3)

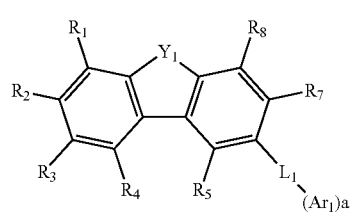
(1-4)

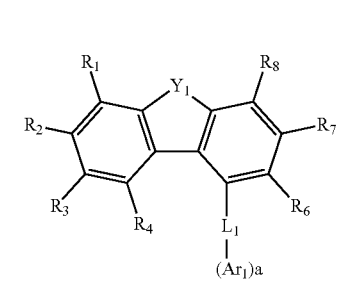
(1-5)

wherein $Y_1$ represents O, S, C $R_{11}$ $R_{12}$, or $NR_{13}$;

$R_1$ to $R_8$, and $R_{13}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3-to 7-membered) heterocycloalkyl, a substituted or unsubstituted (C6-C30)aryl, or a substituted or unsubstituted (3- to 30-membered)heteroaryl; and $L_1$, $Ar_1$, a, $R_{11}$, and $R_{12}$ are as defined in claim 1.

3. The plurality of host materials according to claim 1, wherein formula 2 is represented by at least one of the following formulas 2-1 to 2-6:

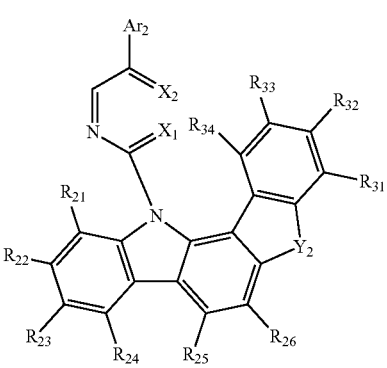
(2-1)

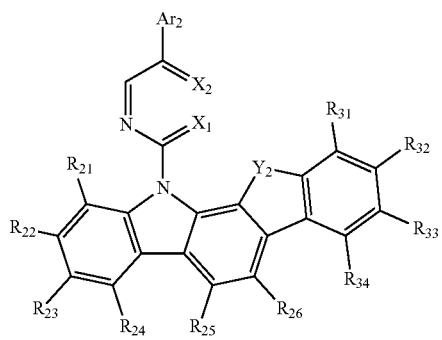
(2-2)

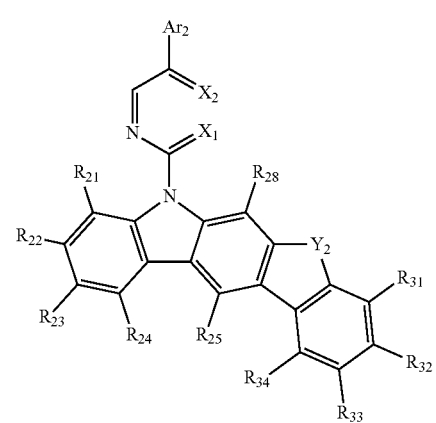
(2-3)

(2-4)

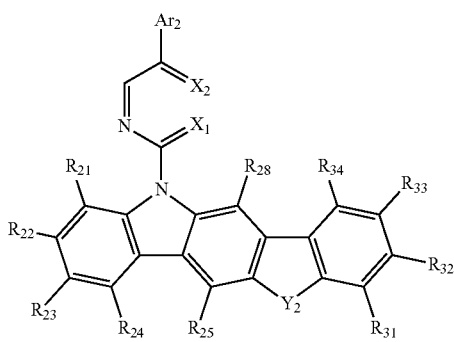

(2-5)

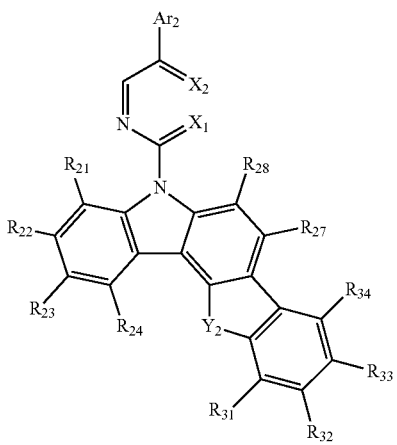

(2-6)

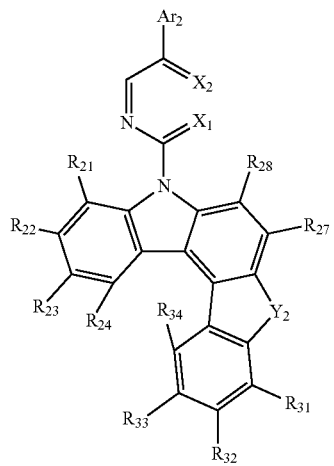

wherein $R_{21}$ to $R_{28}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; and $Y_2$, $X_1$, $X_2$, $Ar_2$, and $R_{31}$ to $R_{34}$ are as defined in claim 1.

4. The plurality of host materials according to claim 1, wherein the substituents of the substituted alkyl, the substituted cycloalkyl, the substituted cycloalkenyl, the substituted heterocycloalkyl, the substituted aryl(ene), and the substituted heteroaryl(ene) in $R_1$ to $R_8$, $R_{11}$ to $R_{16}$, $R_{21}$ to $R_{28}$, $R_{31}$ to $R_{34}$, $L_1$, $Ar_1$, and $Ar_2$ each independently are at least one selected from the group consisting of deuterium; a halogen; a cyano; a carboxyl; a nitro; a hydroxyl; a (C1-C30)alkyl; a halo(C1-C30)alkyl;

a (C2-C30)alkenyl; a (C2-C30)alkynyl; a (C1-C30) alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30) aryl unsubstituted or substituted with at least one of a (C1-C30)alkyl(s), a (3-to 30-membered)heteroaryl(s), and a tri(C6-C30)arylsilyl(s); a tri(C1-C30)alkylsilyl; a tri(C6-C30)arylsilyl; a di(C1-C30)alkyl (C6-C30)arylsilyl; a (C1-C30)alkyldi(C6-C30)arylsilyl; an amino; a mono- or di-(C1-C30)alkylamino; a mono-or di-(C6-C30)arylamino; a (C1-C30) alkyl (C6-C30)arylamino;

a (C1-C30)alkylcarbonyl; a (C1-C30)alkoxycarbonyl; a (C6-C30)arylcarbonyl; a di(C6-C30)arylboronyl; a di(C1-C30alkylboronyl; a (C1-C30)alkyl (C6-C30arylboronyl; a (C6-C30)aryl(C1-C30)alkyl; and a (C1-C30)alkyl (C6-C30) aryl.

5. The plurality of host materials according to claim 1, wherein in formula 1, $Ar_1$ each independently represents a substituted or unsubstituted pyridyl, a substituted or unsubstituted pyrazinyl, a substituted or unsubstituted pyrimidinyl, a substituted or unsubstituted pyridazinyl, a substituted or unsubstituted triazinyl, a substituted or unsubstituted quinolyl, a substituted or unsubstituted isoquinolyl, a substituted or unsubstituted cinnolinyl, a substituted or unsubstituted quinazolinyl, a substituted or unsubstituted quinoxalinyl, or a substituted or unsubstituted naphthyridinyl.

6. The plurality of host materials according to claim 1, wherein in formula 2, $Ar_2$ each independently represents a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted triphenylenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl, a substituted or unsubstituted fluorenyl, a substituted or unsubstituted benzofluorenyl, a substituted or unsubstituted diphenylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyldibenzofuranylamino.

7. The plurality of host materials according to claim 1, wherein the compound represented by formula 1 is at least one selected from the following compounds:
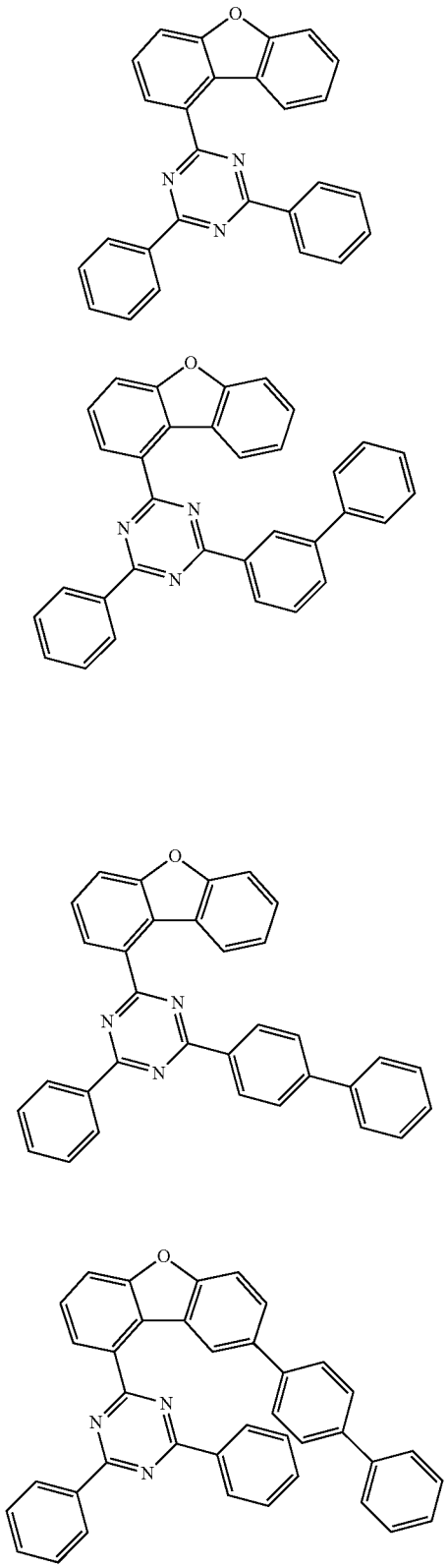
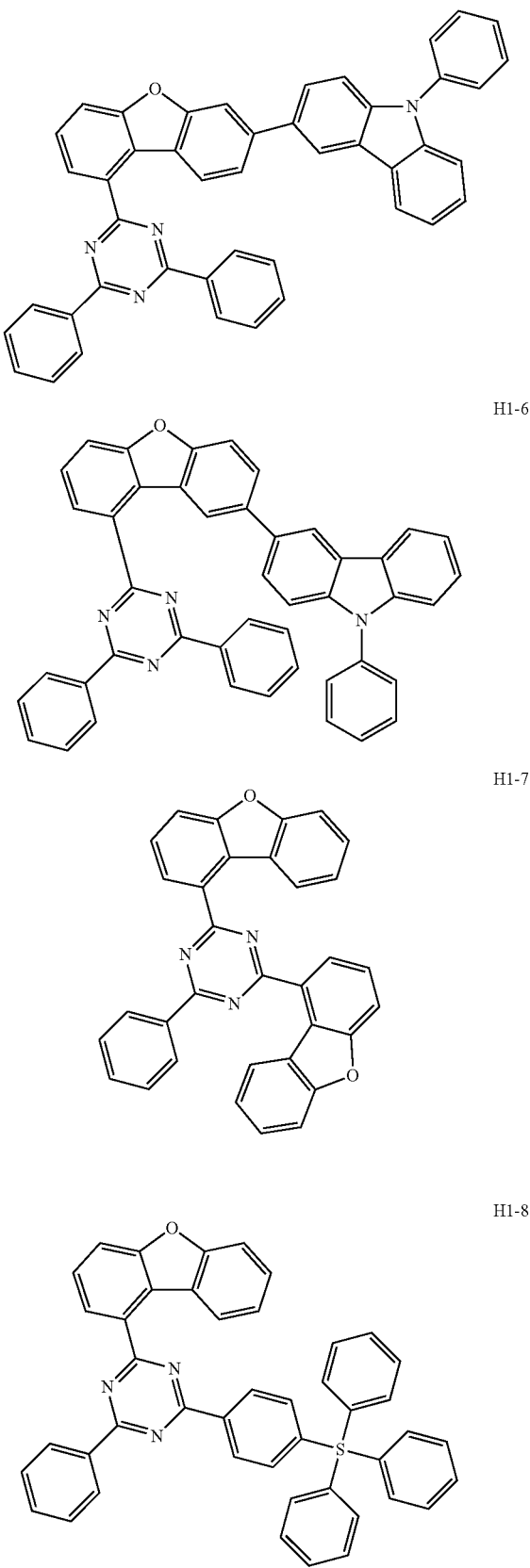

H1-9
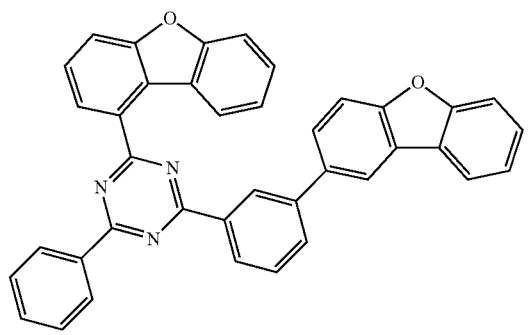
H1-10
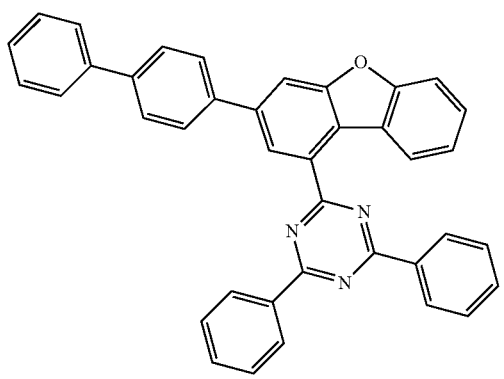
H1-11
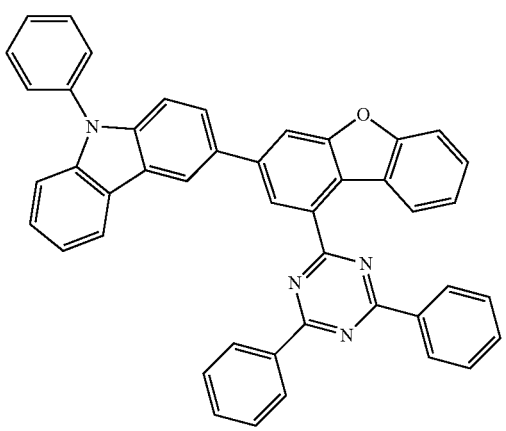
H1-12
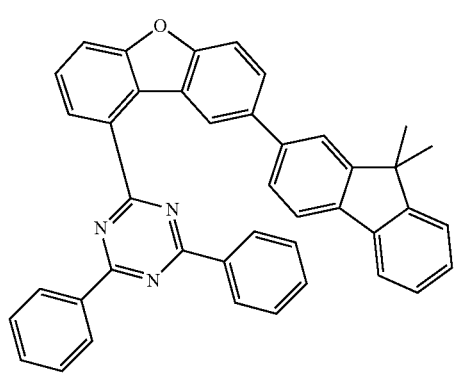
H1-13
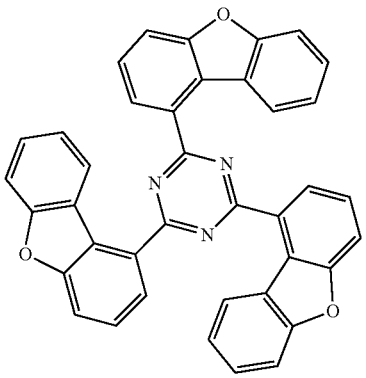
H1-14
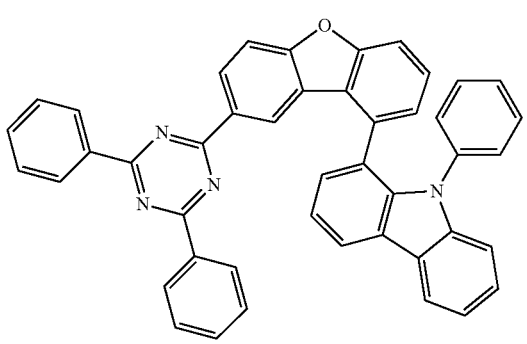
H1-15
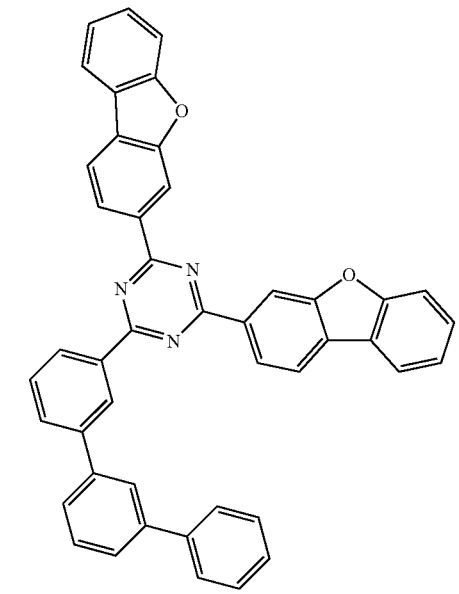

-continued
H1-16
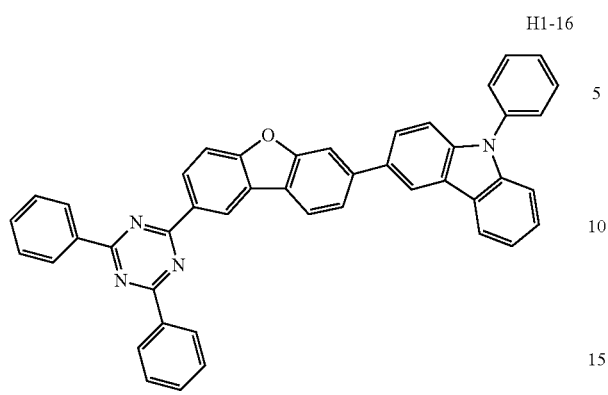
H1-19
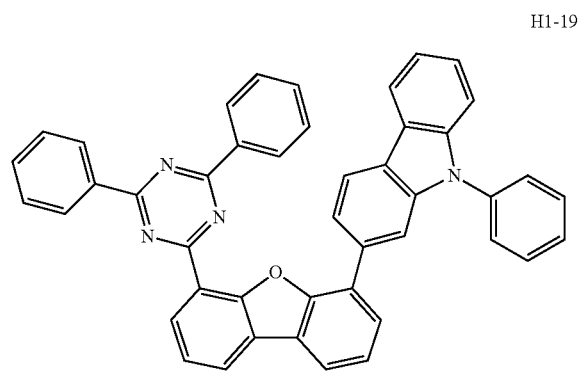
H1-17
H1-20
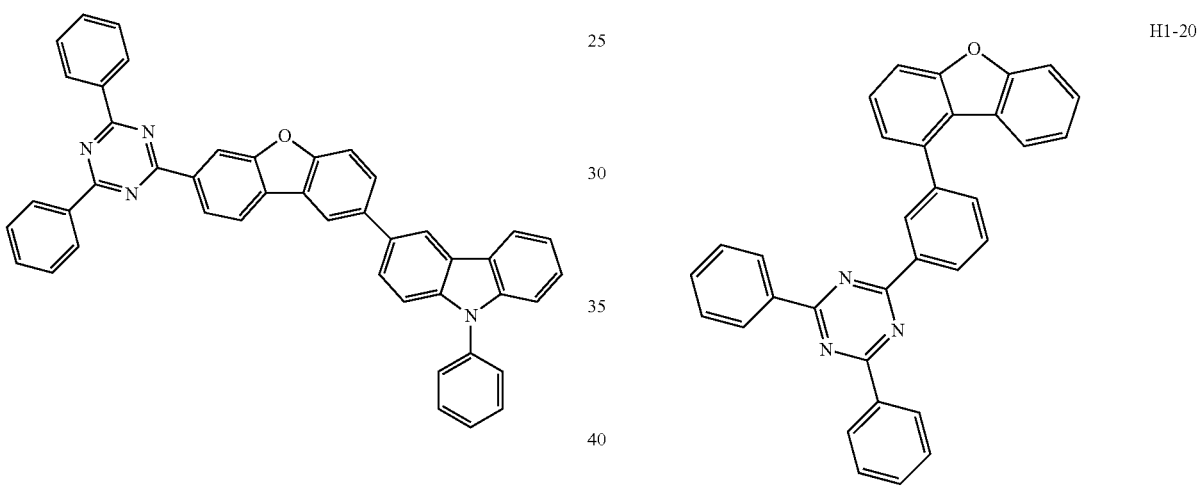
H1-18
H1-21
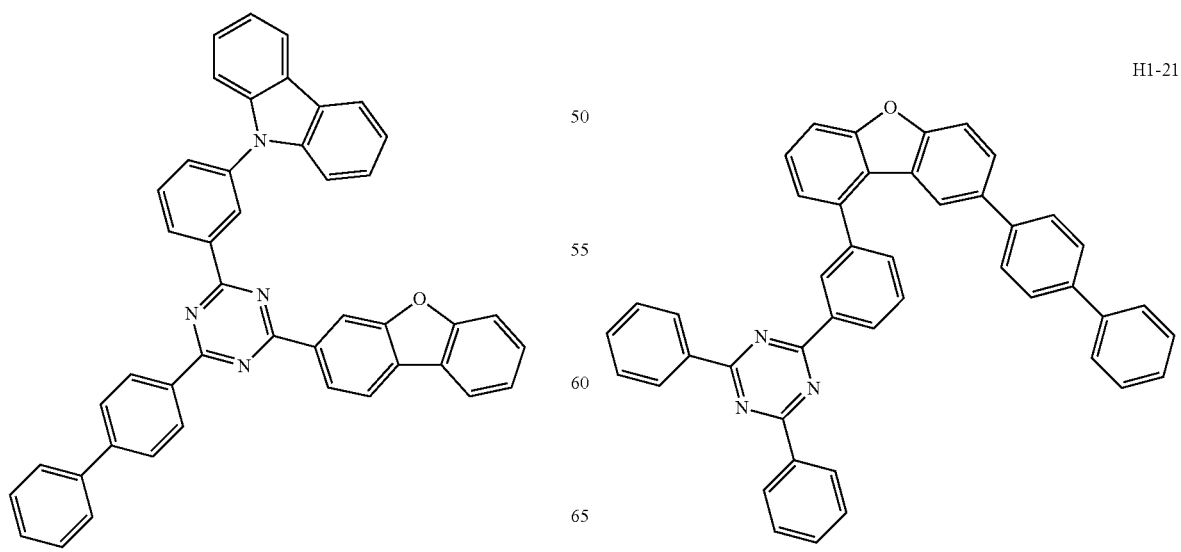

H1-22
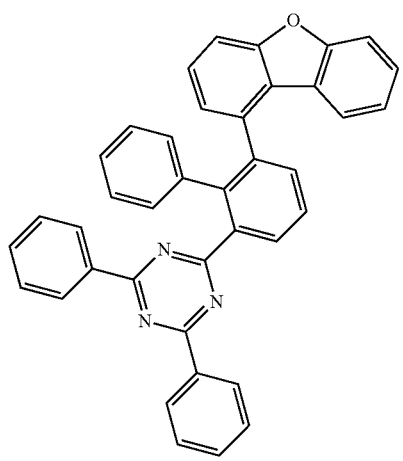
H1-23
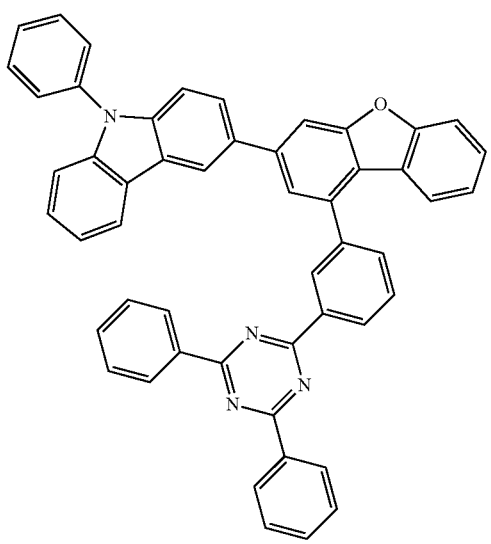
H1-24
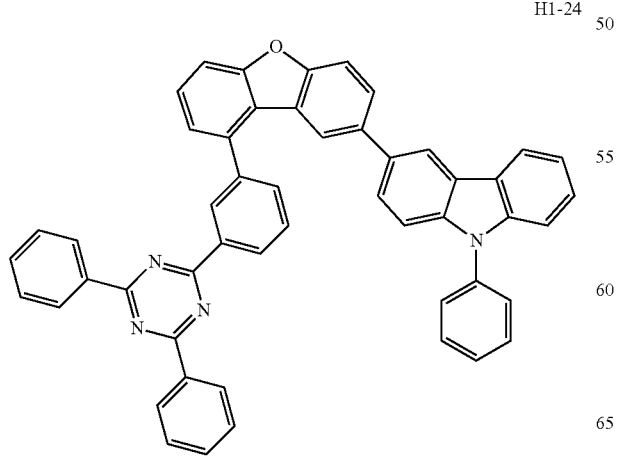
H1-25
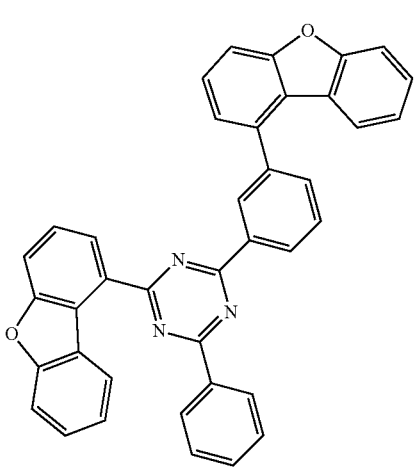
H1-26
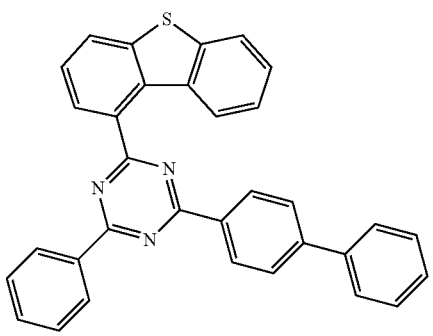
H1-27
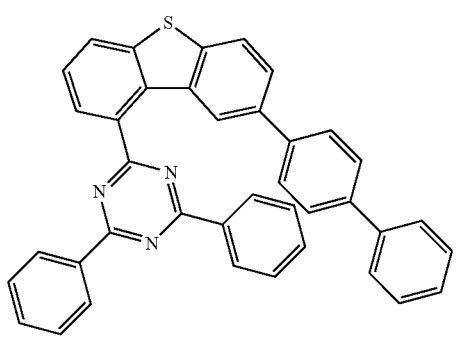

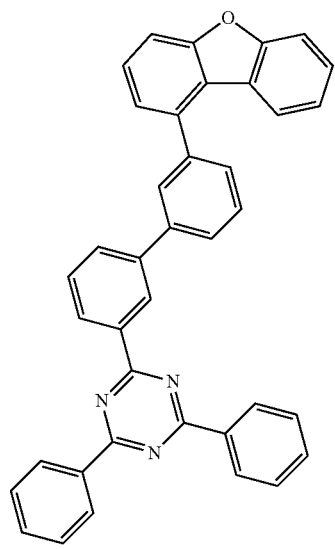
H1-28
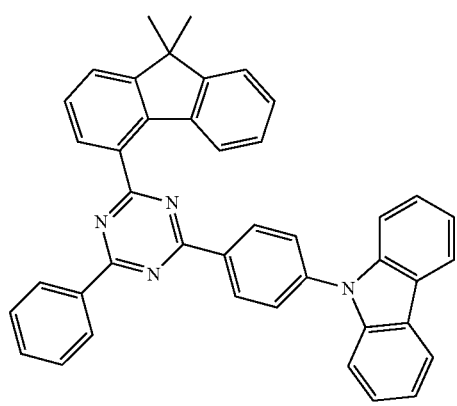
H1-29
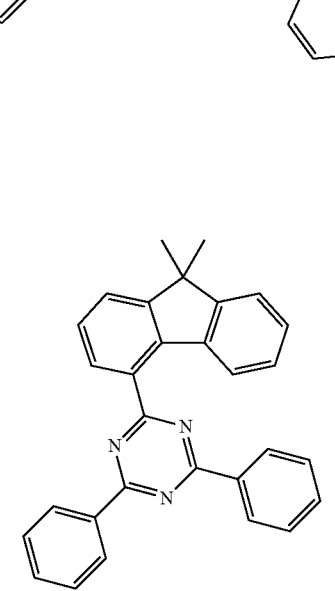
H1-30
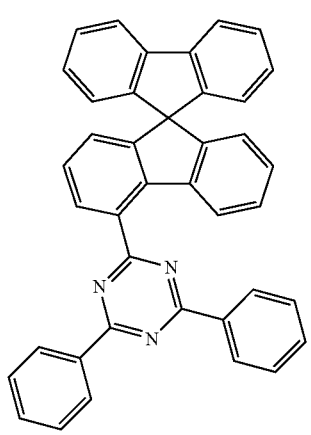
H1-31
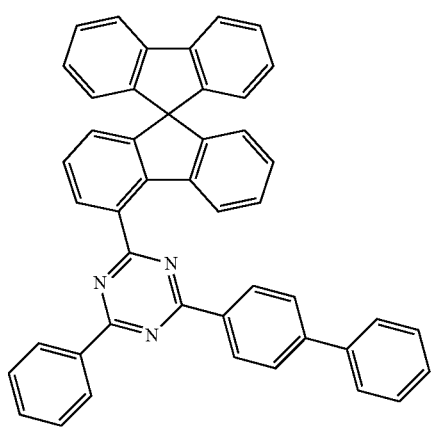
H1-32
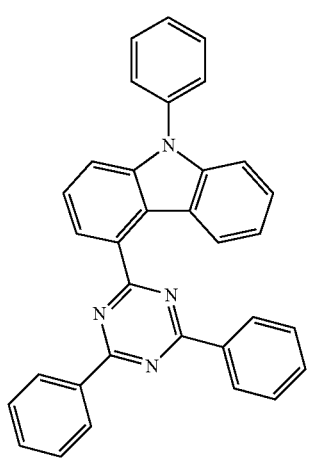
H1-33

H1-34
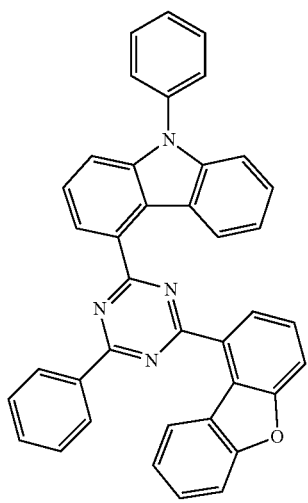
H1-35
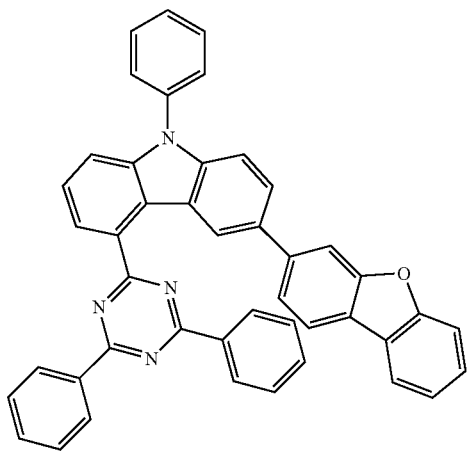
H1-36
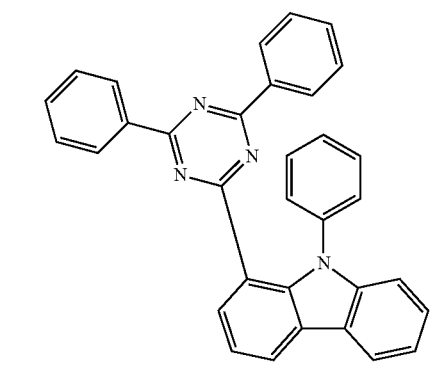
H1-37
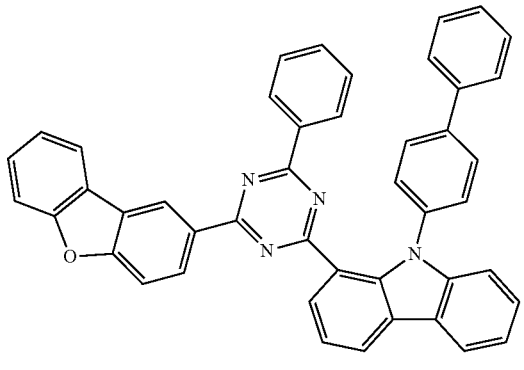
H1-38
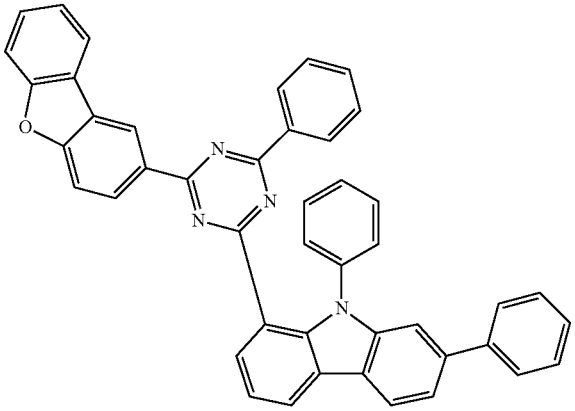
H1-39
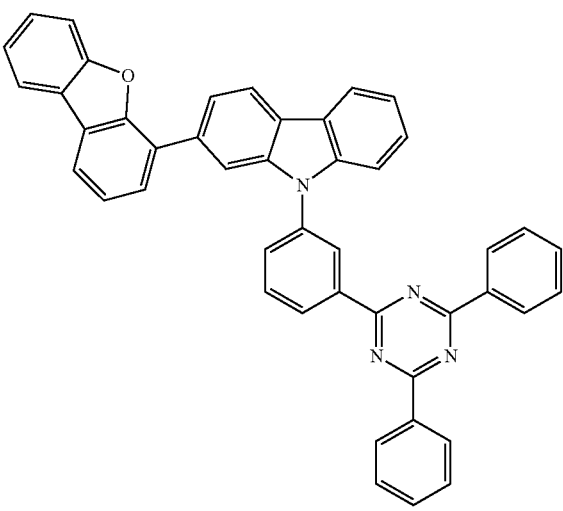

H1-40
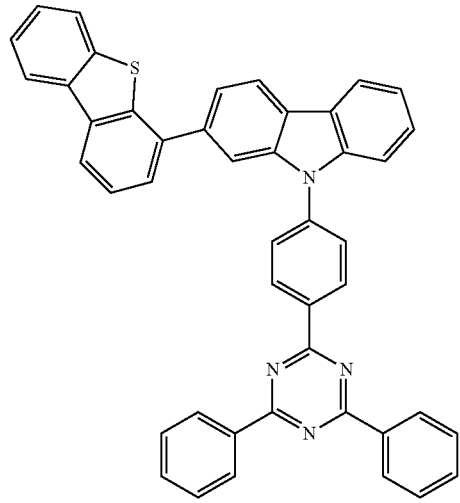
H1-41
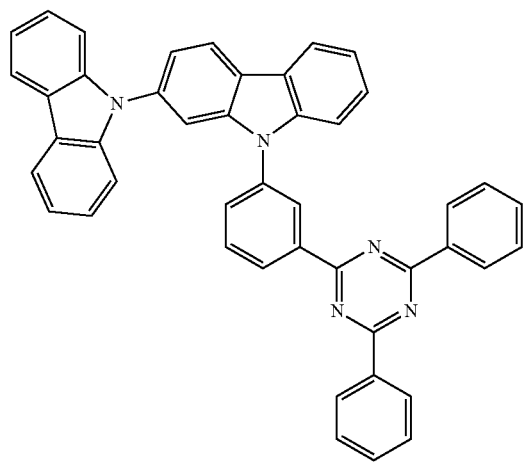
H1-42
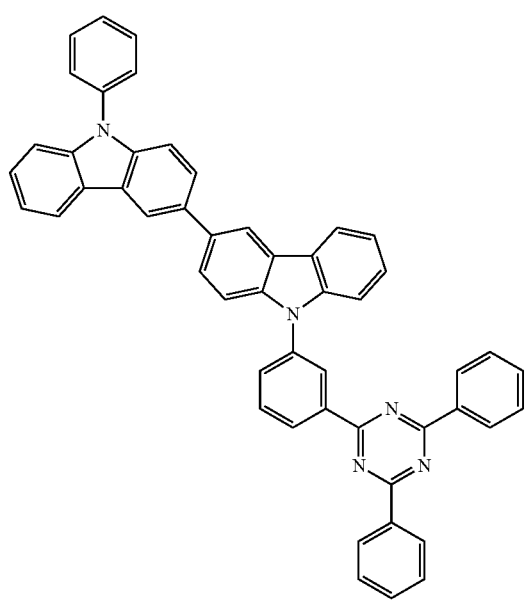
H1-43
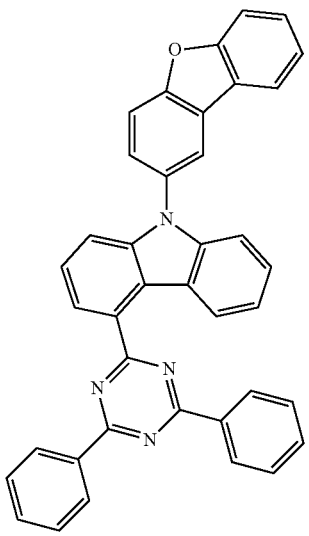
H1-44
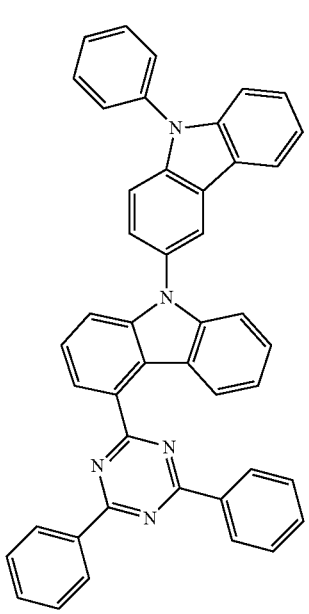
H1-45
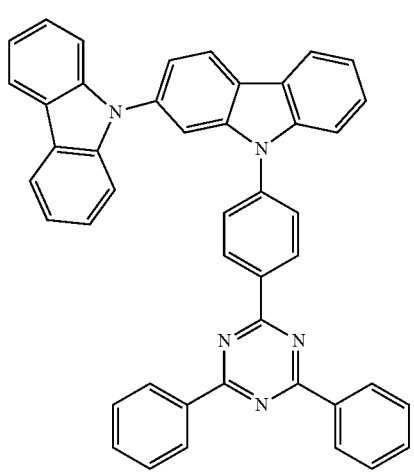

H1-46
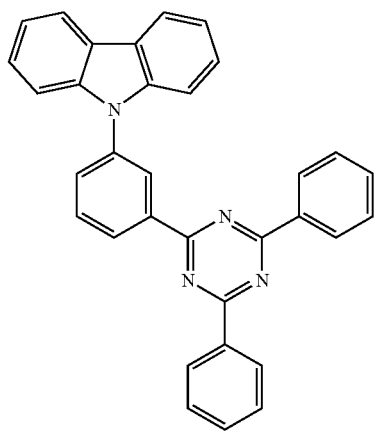
H1-47
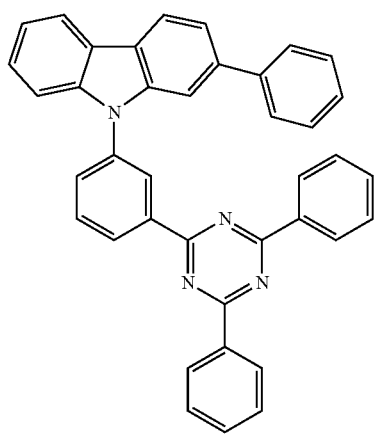
H1-48
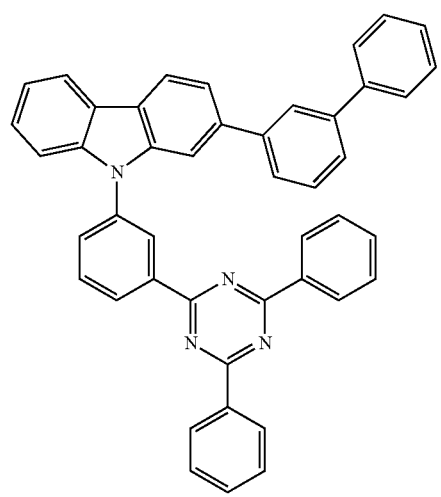
H1-49
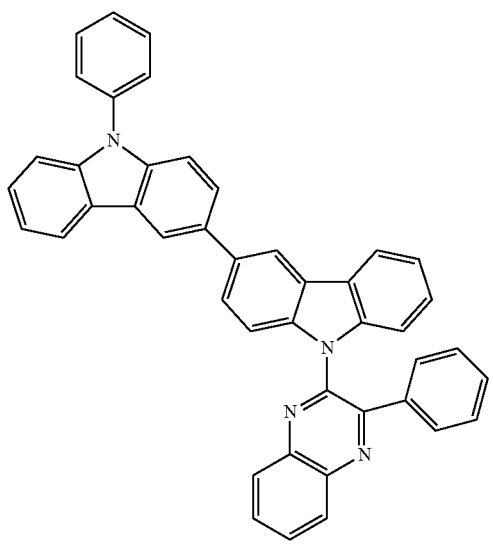
H1-50
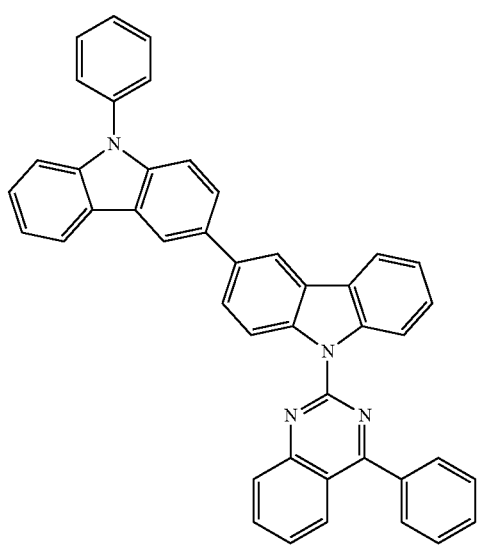
H1-51
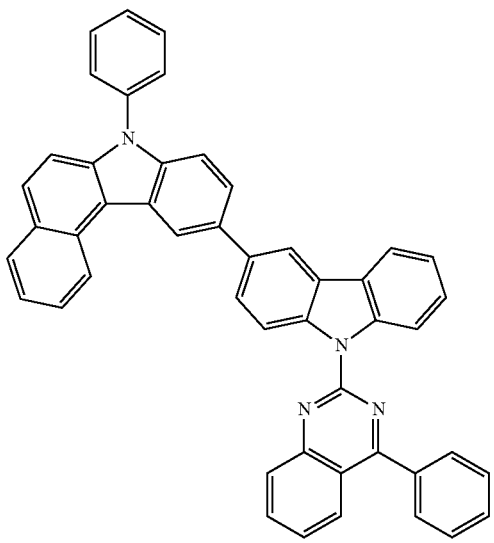

H1-52
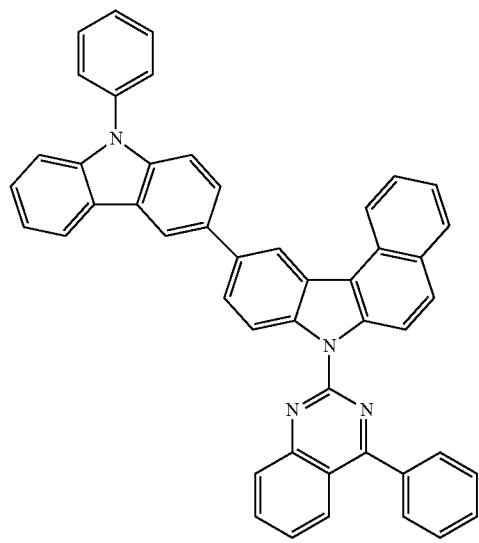
H1-55
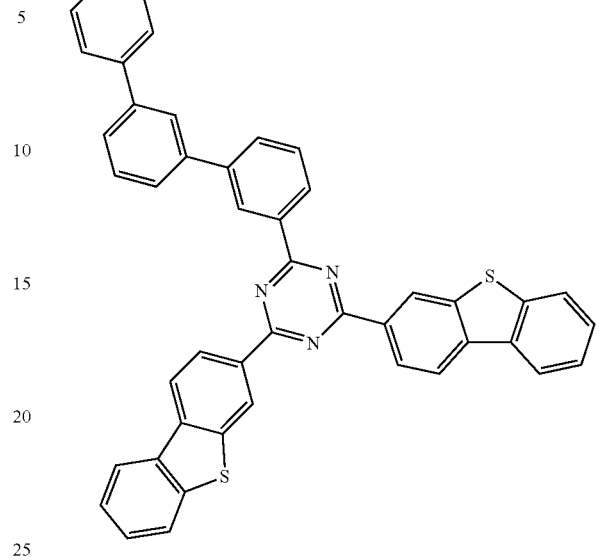
H1-53
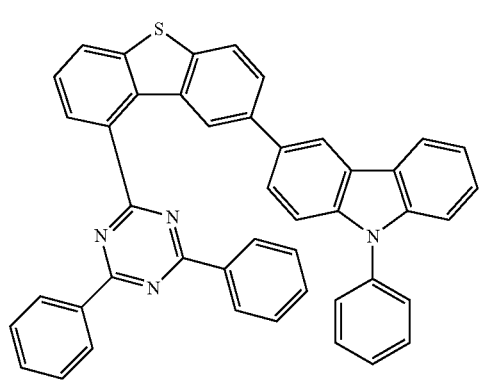
H1-56
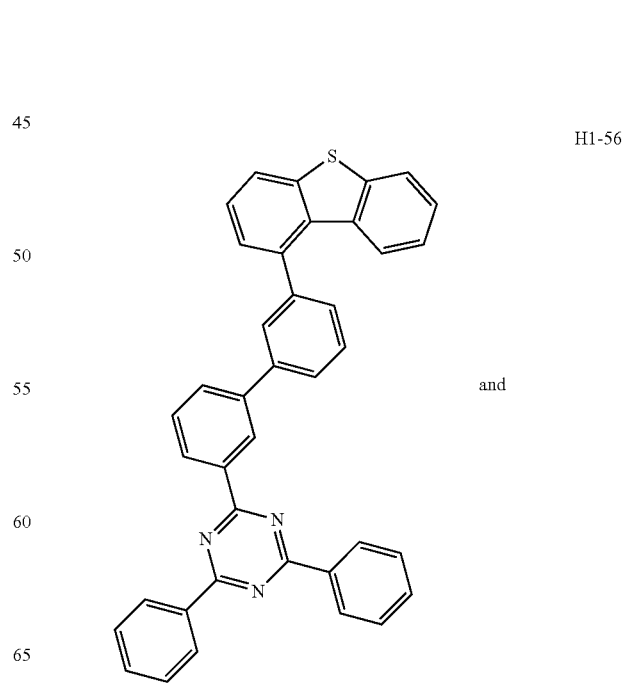
and
H1-54
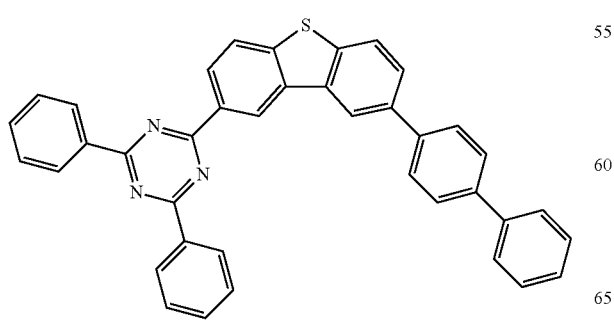

H1-57
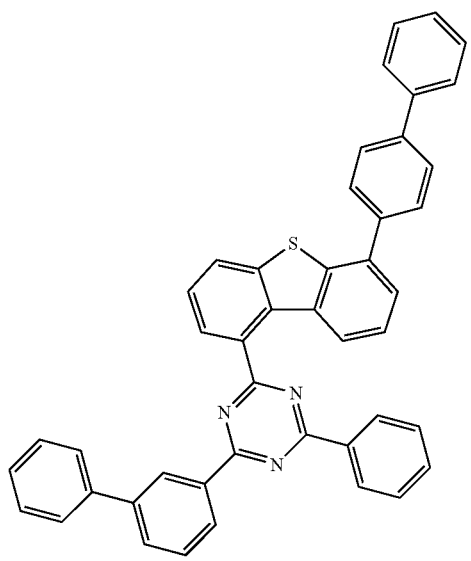
H2-3
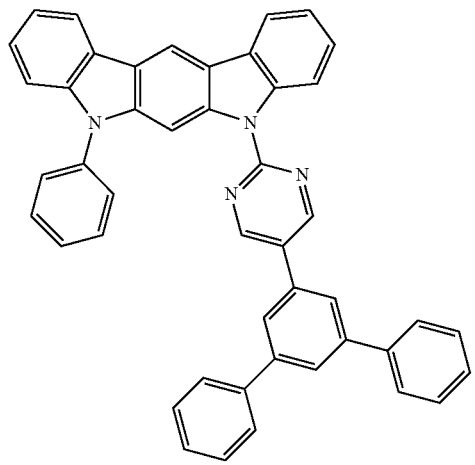
8. The plurality of host materials according to claim 1, wherein the compound represented by formula 2 is at least one selected from the following compounds:
H2-1
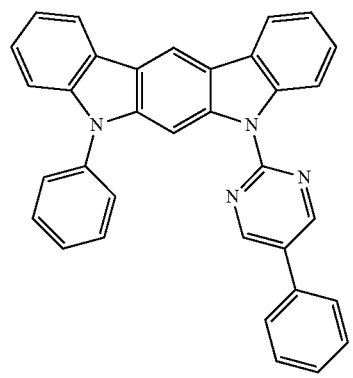
H2-4
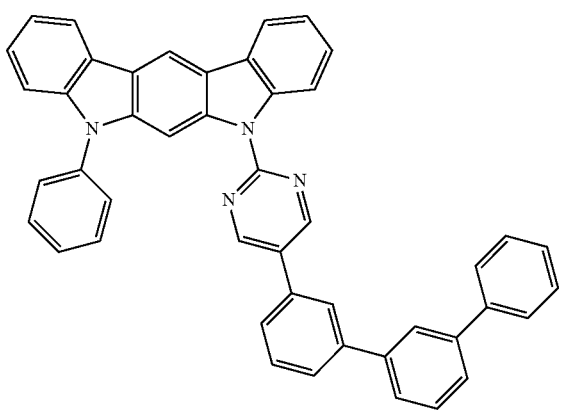
H2-2
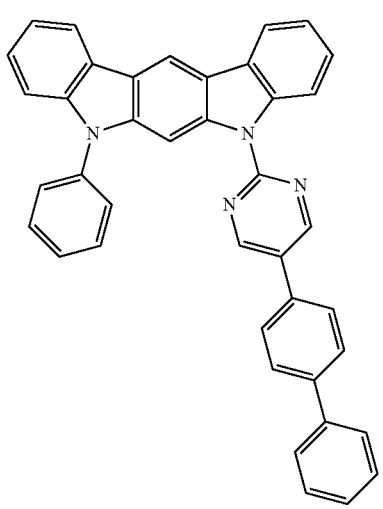
H2-5
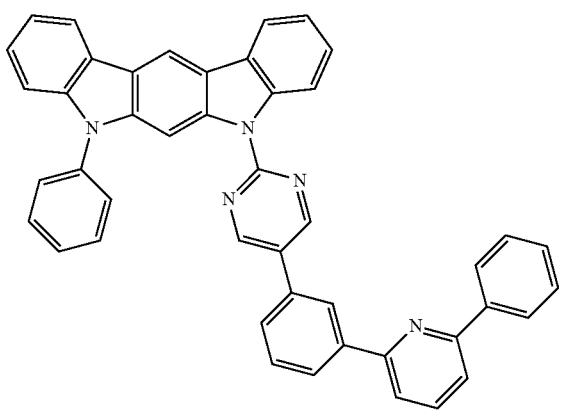

-continued
H2-6
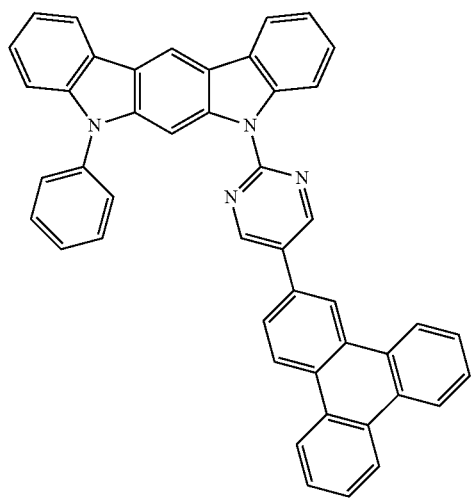
H2-9
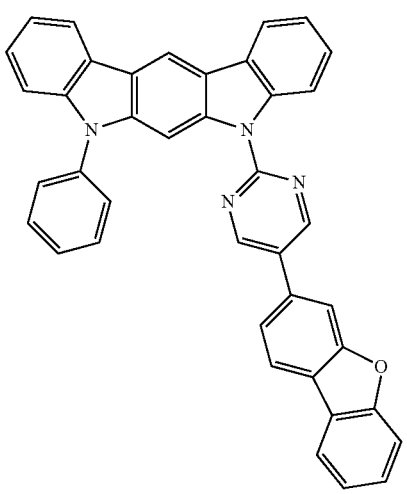
H2-7
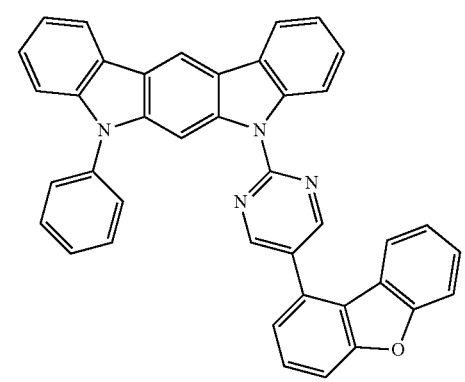
H2-10
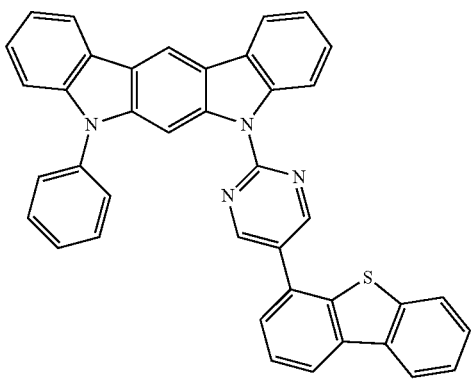
H2-8
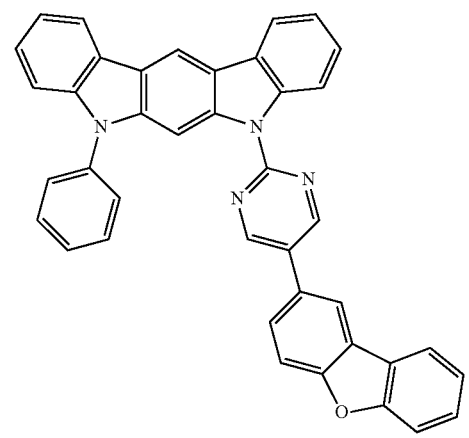
H2-11
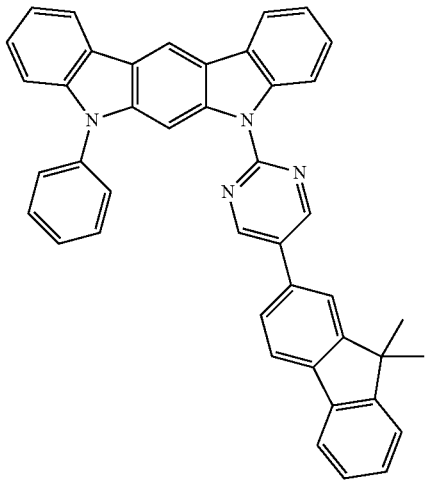

-continued
H2-12
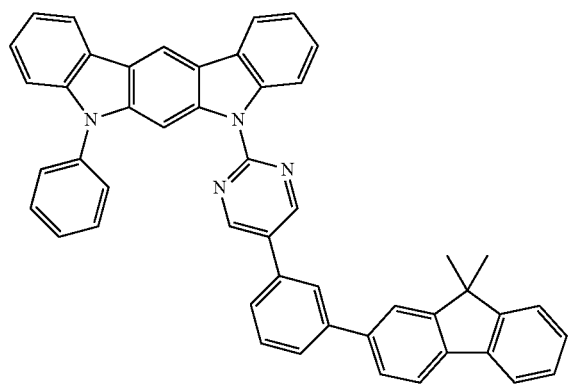
H2-13
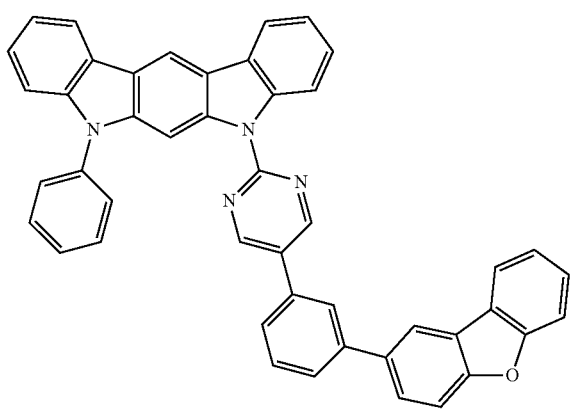
H2-14
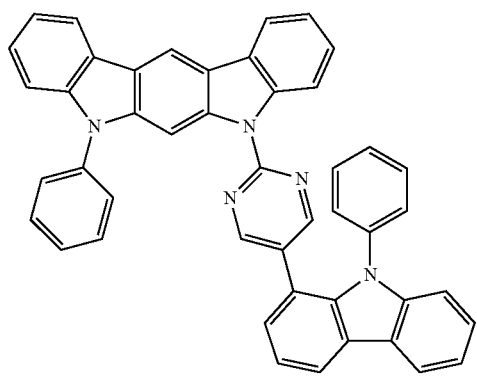
-continued
H2-15
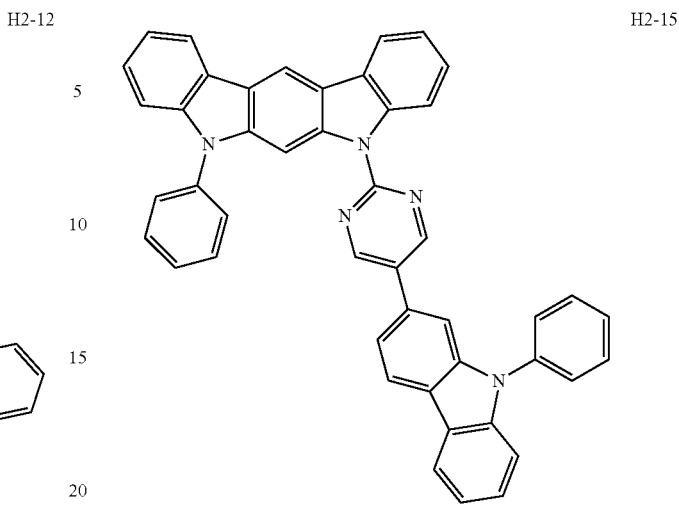
H2-16
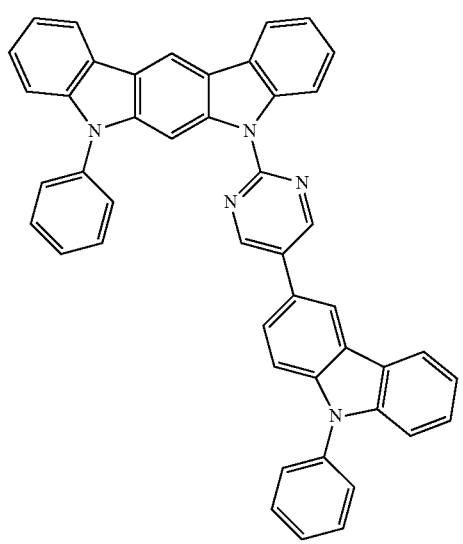
H2-17
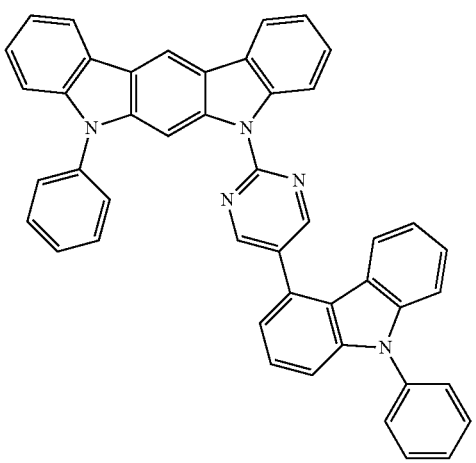

-continued
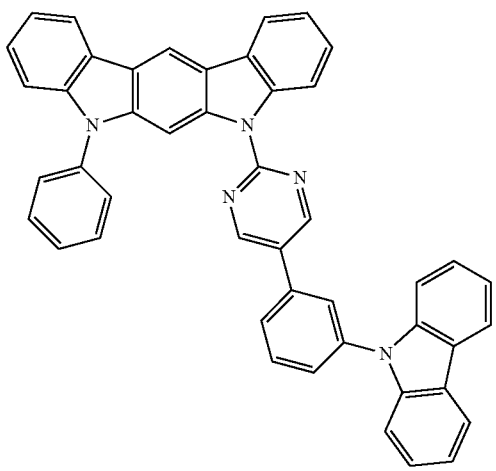
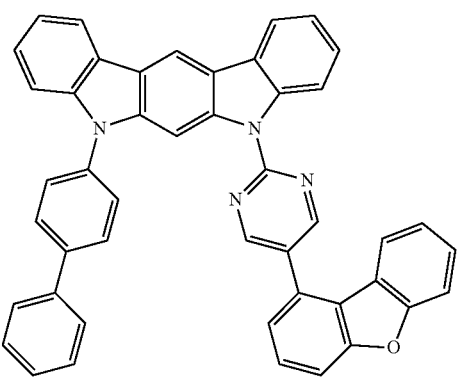

H2-26
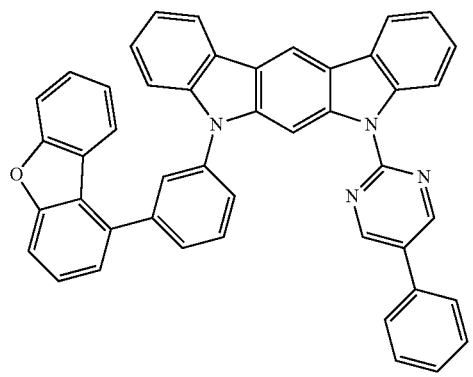
H2-27
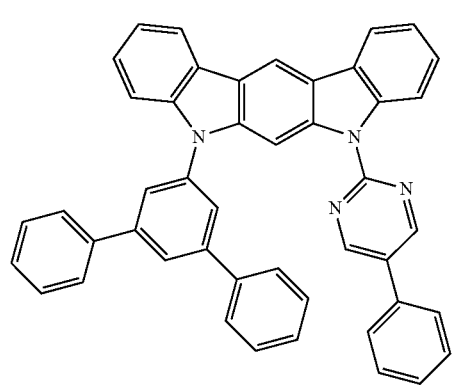
H2-28
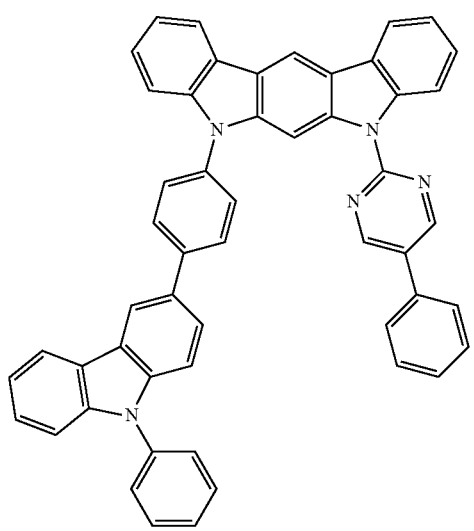
H2-29
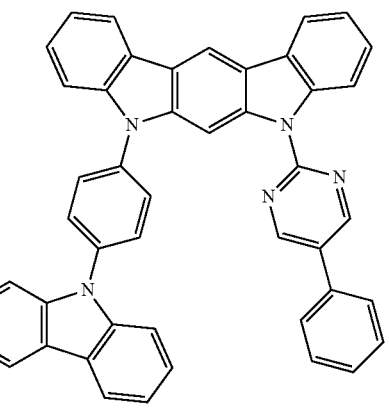
H2-30
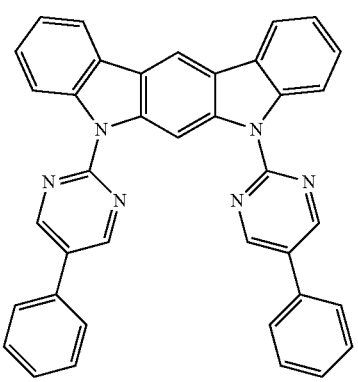
H2-31
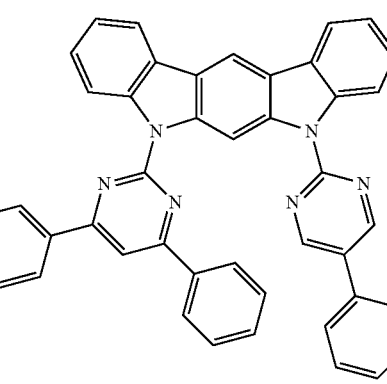
H2-32
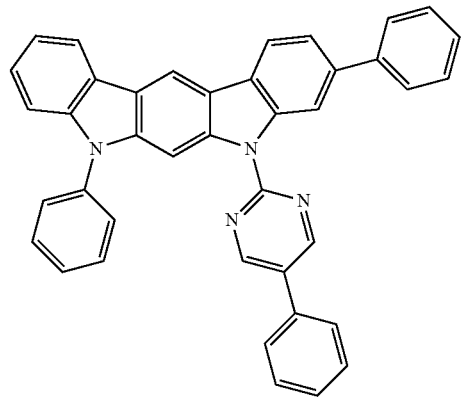

H2-33
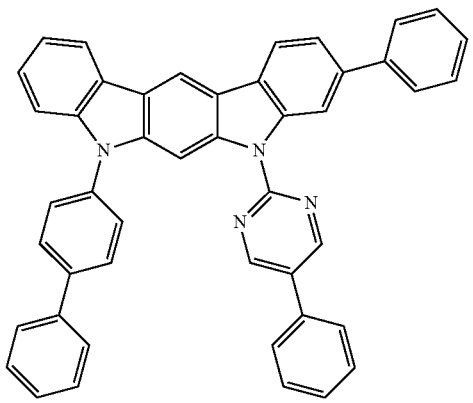
H2-34
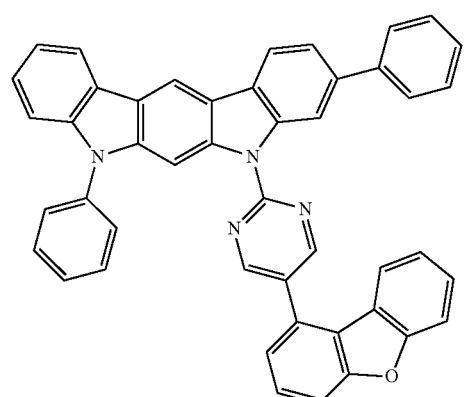
H2-35
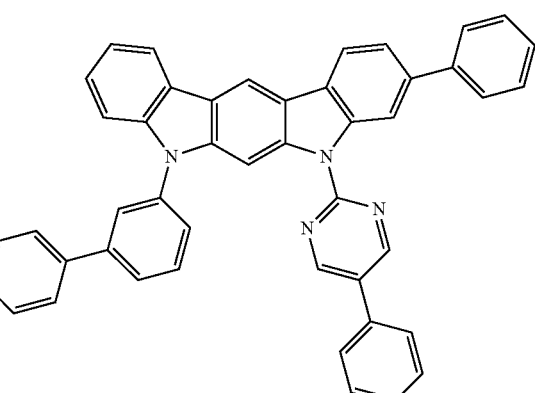
H2-36
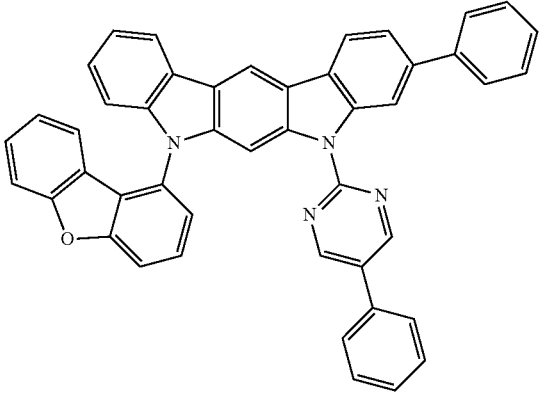
H2-37
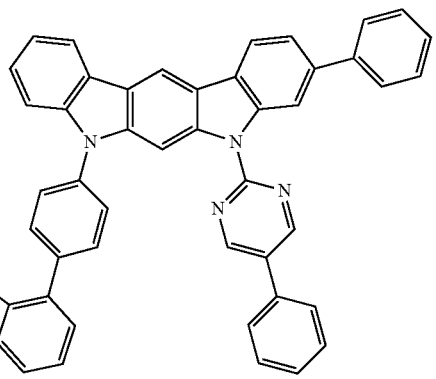
H2-38
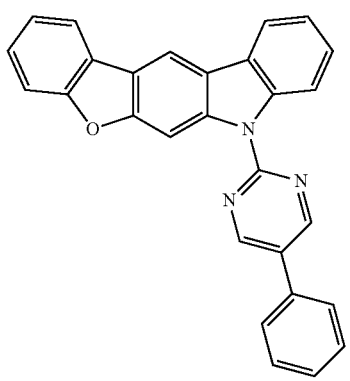
H2-39
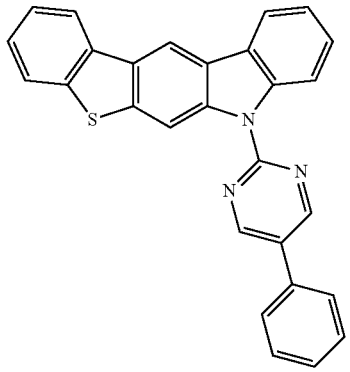
H2-40
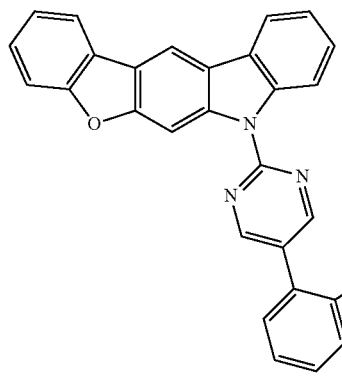

H2-41
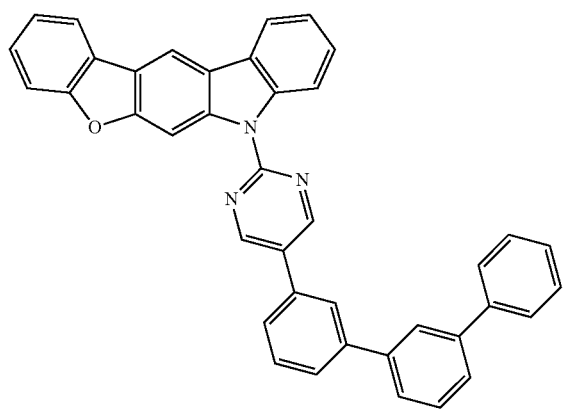
H2-42
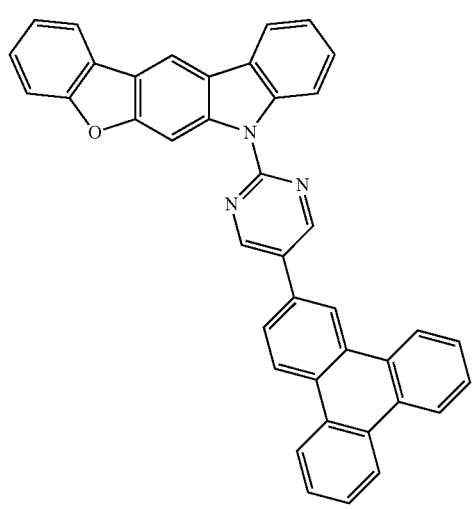
H2-43
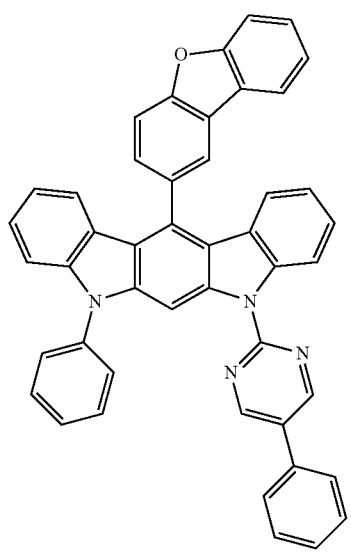
H2-44
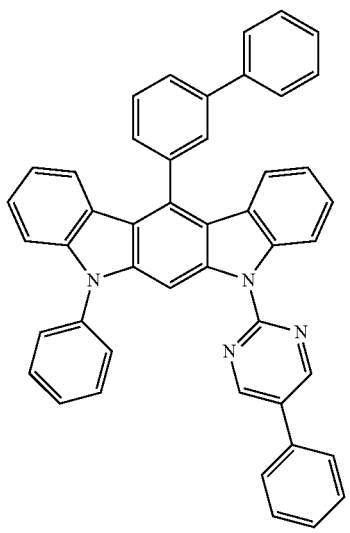
H2-45
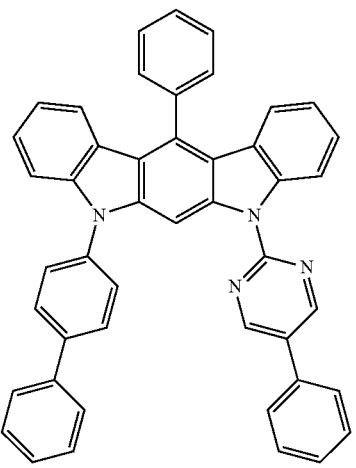
H2-46
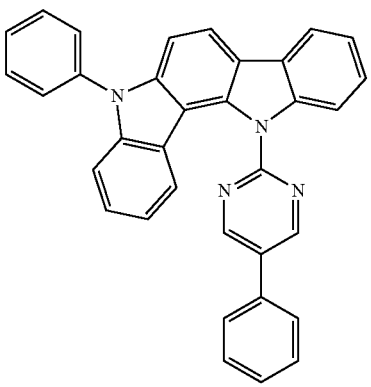

H2-47
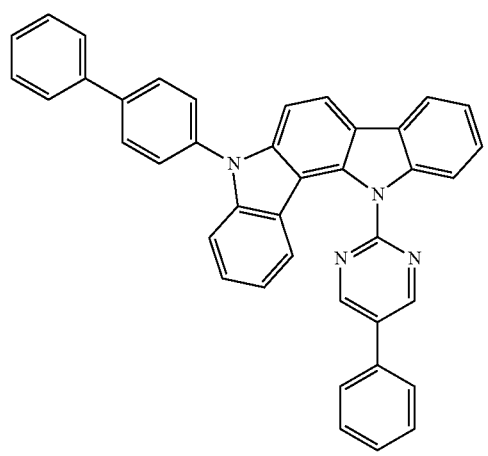
H2-48
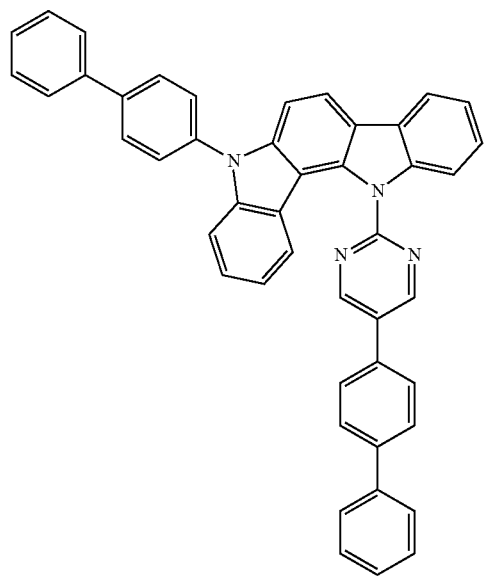
H2-49
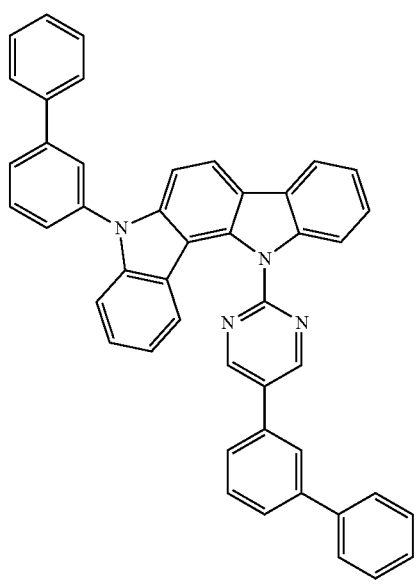
H2-50
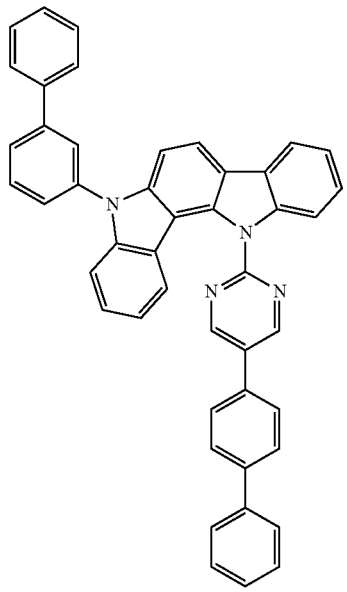
H2-51
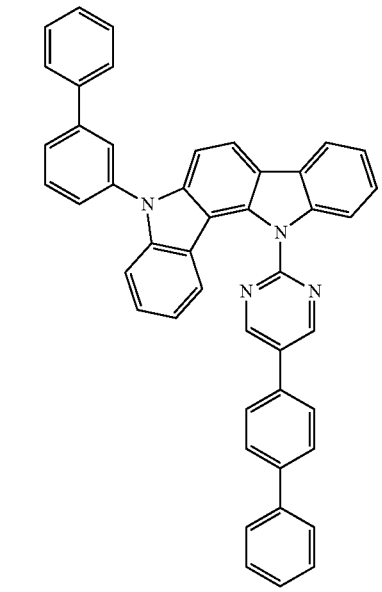

H2-52
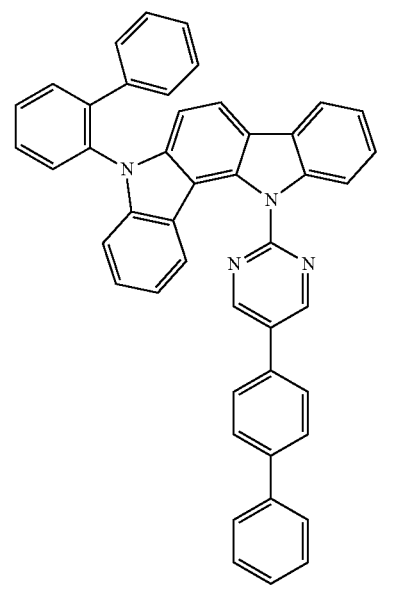
H2-53
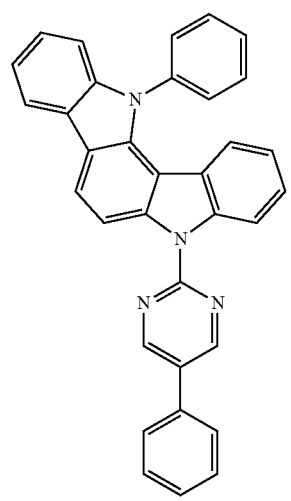
H2-54
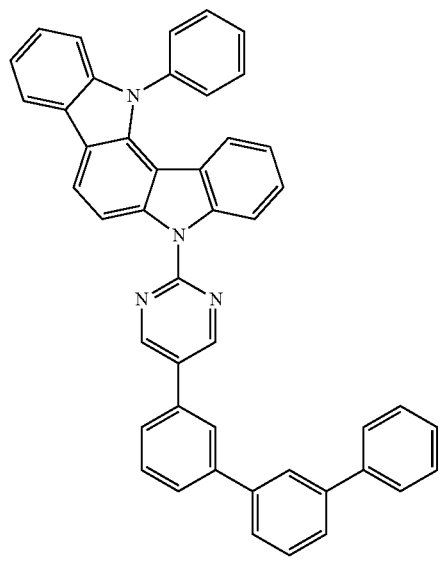
H2-55
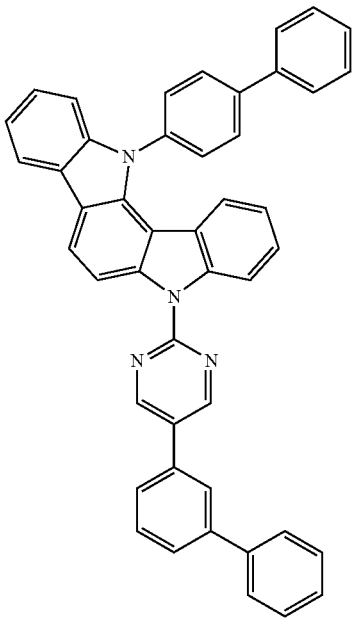
H2-56
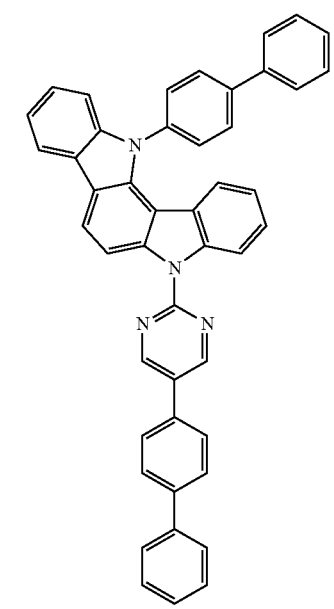

H2-57
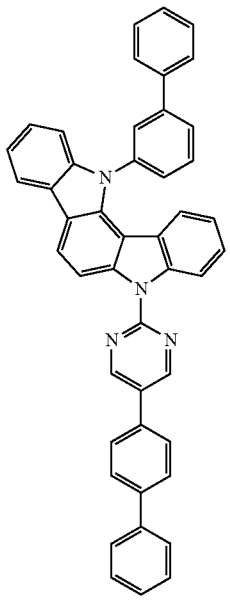
H2-58
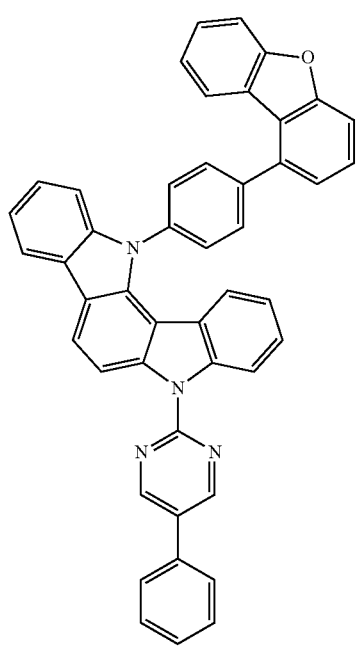
H2-59
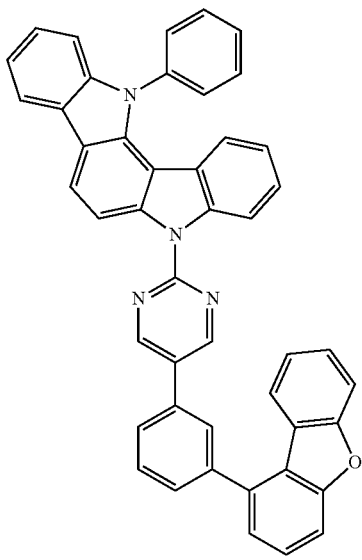
H2-60

H2-61
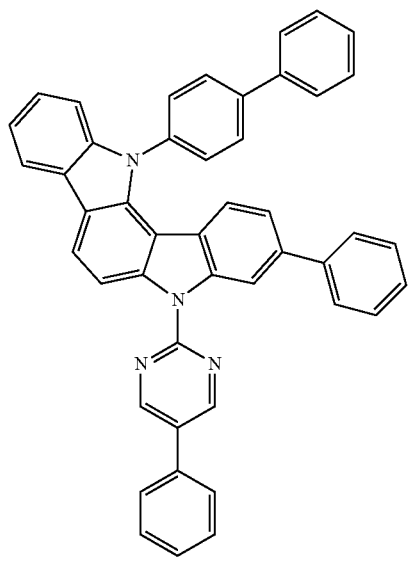
H2-62
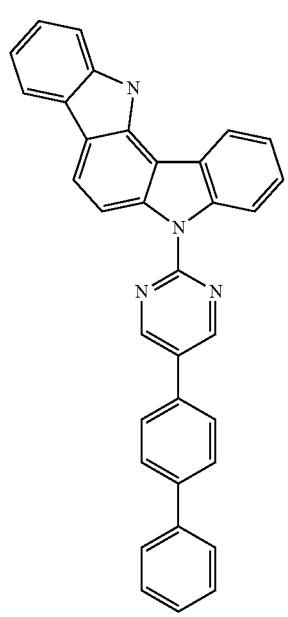
H2-63
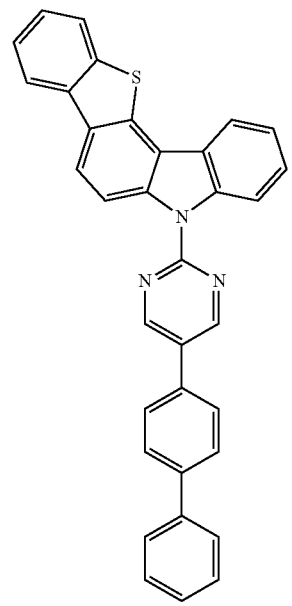
H2-64
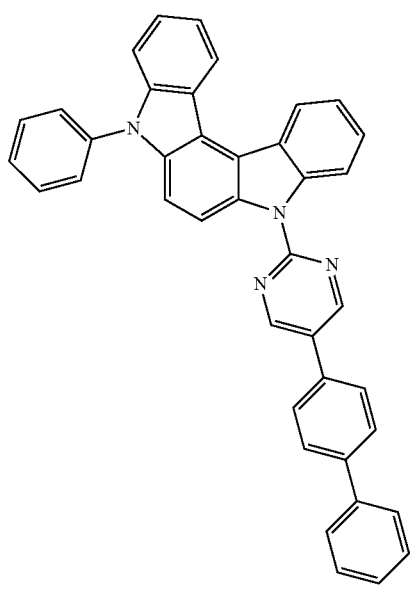
H2-65
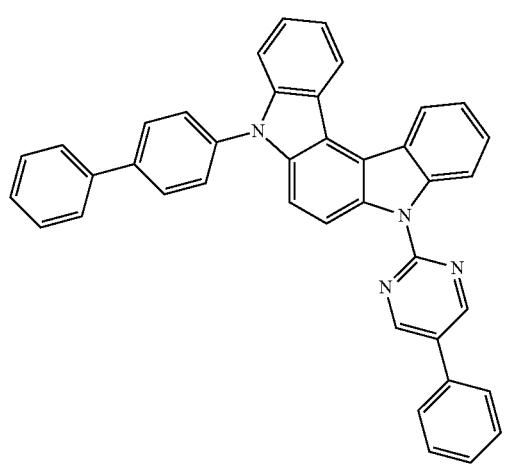

-continued
H2-66
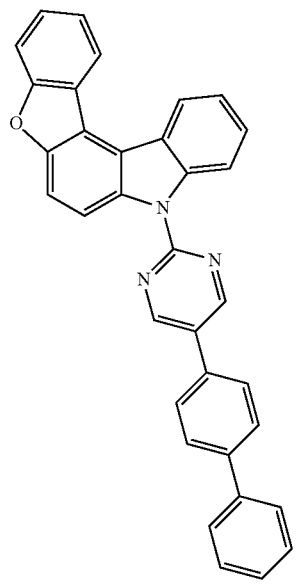
H2-68
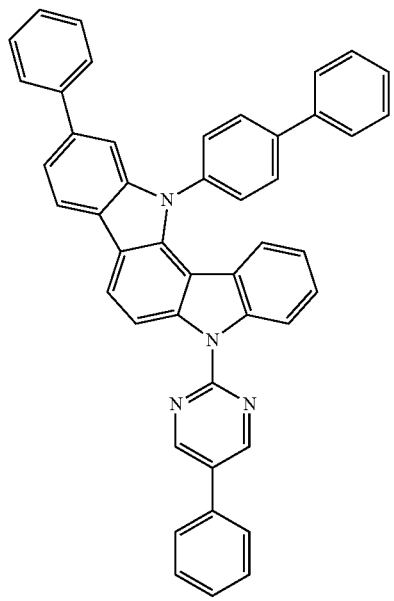
H2-67
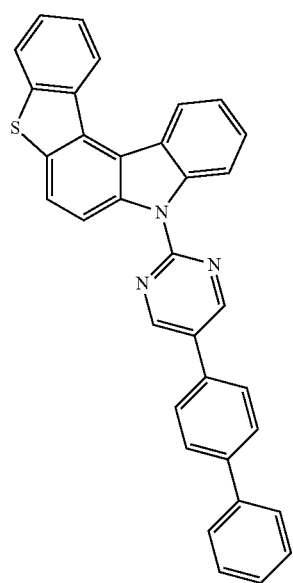
H2-69
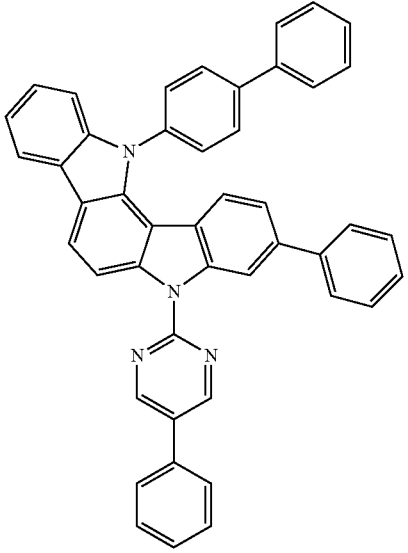

H2-70
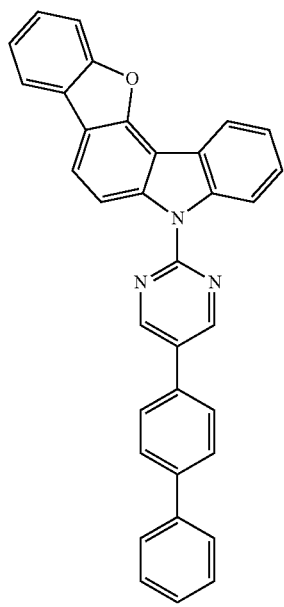
H2-71
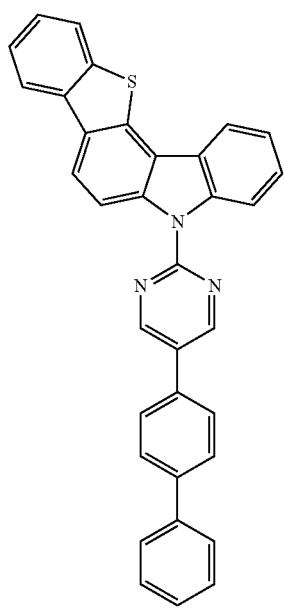
H2-72
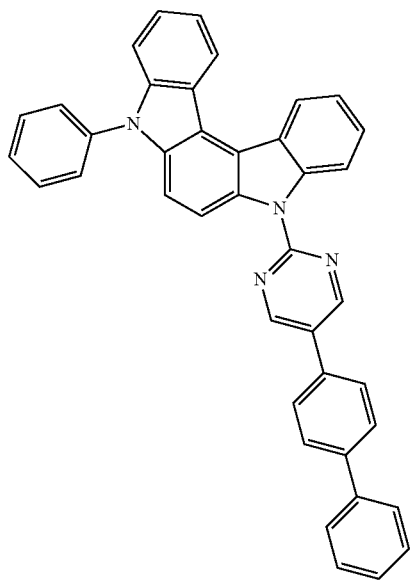
H2-73
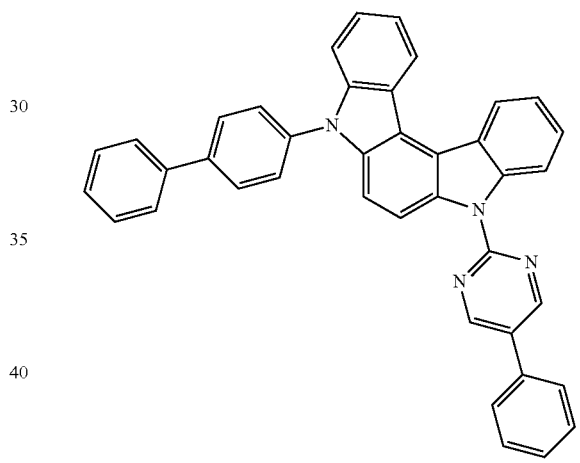
H2-74
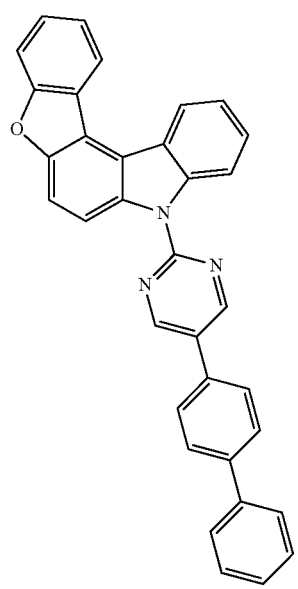

H2-75
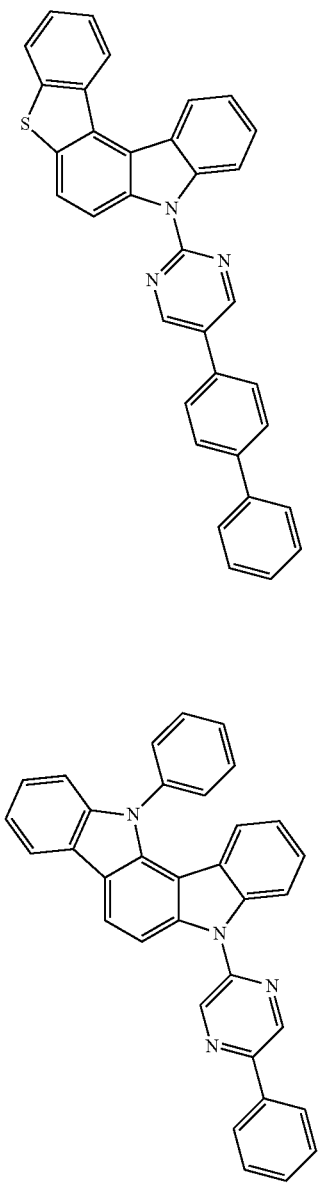
H2-76
H2-77
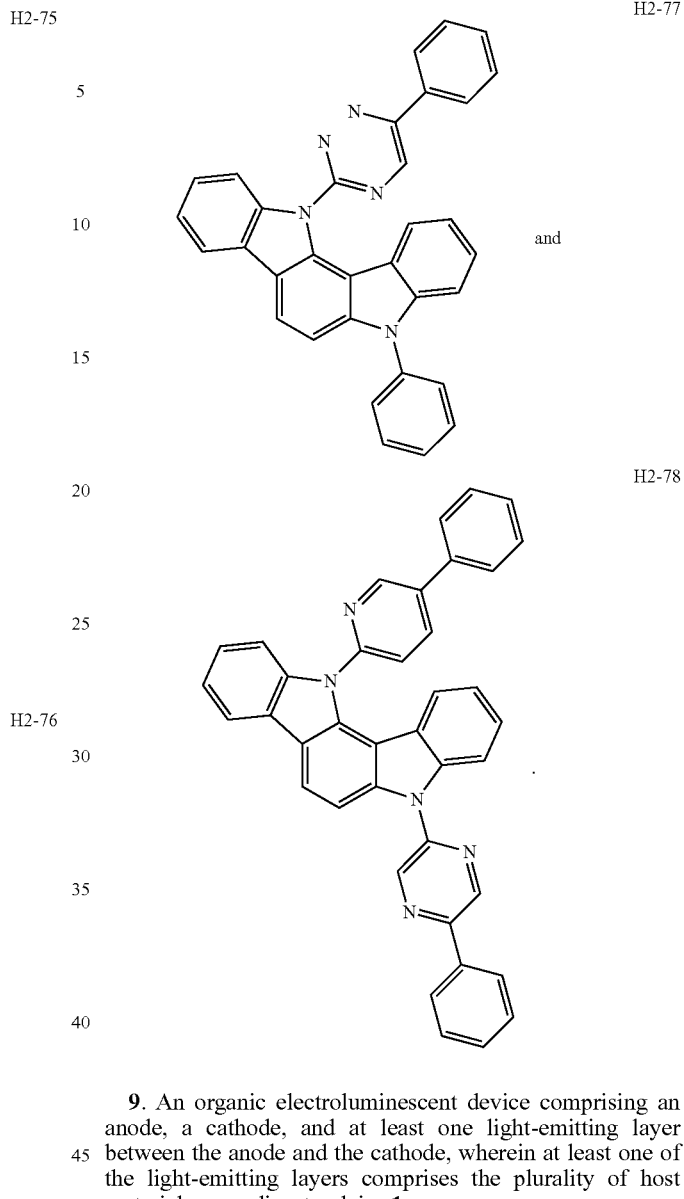
and
H2-78
9. An organic electroluminescent device comprising an anode, a cathode, and at least one light-emitting layer between the anode and the cathode, wherein at least one of the light-emitting layers comprises the plurality of host materials according to claim 1.
* * * * *